(12) United States Patent
Cheng et al.

(10) Patent No.: US 11,692,162 B2
(45) Date of Patent: Jul. 4, 2023

(54) METHODS, DEVICES, AND APPARATUS FOR WASHING SAMPLES ON ARRAY PLATES

(71) Applicant: CURIOX BIOSYSTEMS PTE LTD., Singapore (SG)

(72) Inventors: Kong Leong Cheng, Singapore (SG); Namyong Kim, Boston, MA (US)

(73) Assignee: CURIOX BIOSYSTEMS PTE LTD., Singapore (SG)

( * ) Notice: Subject to any disclaimer, the term of this patent is extended or adjusted under 35 U.S.C. 154(b) by 287 days.

(21) Appl. No.: 16/590,187

(22) Filed: Oct. 1, 2019

(65) Prior Publication Data
US 2020/0032189 A1    Jan. 30, 2020

Related U.S. Application Data

(63) Continuation of application No. PCT/IB2018/000436, filed on Apr. 5, 2018.
(Continued)

(51) Int. Cl.
*B01L 3/02* (2006.01)
*G01N 35/10* (2006.01)
(Continued)

(52) U.S. Cl.
CPC .......... *C12M 33/04* (2013.01); *B01L 3/0293* (2013.01); *B01L 13/02* (2019.08); *C12M 29/00* (2013.01); *G01N 35/1016* (2013.01); *B01L 2200/0605* (2013.01); *B01L 2200/0642* (2013.01); *B01L 2300/0832* (2013.01); *B01L 2300/165* (2013.01); *G01N 2035/00524* (2013.01); *G01N 2035/103* (2013.01); *G01N 2035/1034* (2013.01)

(58) Field of Classification Search
None
See application file for complete search history.

(56) References Cited

U.S. PATENT DOCUMENTS 3,426,108 A    2/1969  Britten
3,754,872 A    8/1973  Zauft
(Continued)

FOREIGN PATENT DOCUMENTS

CN    1460723 A    12/2003
CN    1858593 A    11/2006
(Continued)

OTHER PUBLICATIONS

Curiox Biosystems, PTE Ltd., International Search Report and Written Opinion, PCT/US2020/033251, dated Aug. 4, 2020, 10 pgs.
(Continued)

*Primary Examiner* — Brian R Gordon
(74) *Attorney, Agent, or Firm* — Morgan, Lewis & Bockius LLP

(57) ABSTRACT

An apparatus for washing an array plate includes one or more dispensers and one or more aspirators that are distinct from the one or more dispensers. A respective dispenser of the one or more dispensers is configured to dispense a first liquid on the array plate, and a respective aspirator of the one or more aspirators is configured to aspirate liquid on the array plate. A method for washing particles is also disclosed.

20 Claims, 43 Drawing Sheets

Related U.S. Application Data

(60) Provisional application No. 62/517,166, filed on Jun. 9, 2017, provisional application No. 62/517,788, filed on Jun. 9, 2017, provisional application No. 62/482,140, filed on Apr. 5, 2017.

(51) Int. Cl.
  *C12M 1/26* (2006.01)
  *C12M 1/00* (2006.01)
  *G01N 35/00* (2006.01)

(56) References Cited

U.S. PATENT DOCUMENTS

| | | | |
|---|---|---|---|
| 4,133,211 A * | 1/1979 | Sarstedt | B01L 3/0231 73/864.18 |
| 4,333,356 A | 6/1982 | Bartels et al. | |
| 5,041,266 A | 8/1991 | Fox | |
| 5,219,528 A | 6/1993 | Clark | |
| 5,229,163 A | 7/1993 | Fox | |
| 5,506,121 A | 4/1996 | Skerra et al. | |
| 5,560,811 A | 10/1996 | Briggs et al. | |
| 5,691,147 A | 11/1997 | Draetta et al. | |
| RE35,894 E | 9/1998 | Ellison et al. | |
| 5,817,510 A | 10/1998 | Pandey et al. | |
| 6,048,908 A | 4/2000 | Kitagawa | |
| 6,086,825 A | 7/2000 | Sundberg et al. | |
| 6,103,493 A | 8/2000 | Skerra et al. | |
| 6,130,098 A | 10/2000 | Handique et al. | |
| 6,238,626 B1 | 5/2001 | Higuchi et al. | |
| 6,331,441 B1 | 12/2001 | Balch et al. | |
| 6,534,014 B1 | 3/2003 | Mainquist et al. | |
| 6,565,813 B1 | 5/2003 | Garyantes | |
| 6,578,952 B1 | 6/2003 | Sugiyama et al. | |
| 6,593,146 B1 * | 7/2003 | Lang | G01N 35/1002 73/863.25 |
| 6,664,044 B1 | 12/2003 | Sato | |
| 6,699,437 B1 | 3/2004 | Astle | |
| 6,716,629 B2 | 4/2004 | Hess et al. | |
| 6,767,733 B1 | 7/2004 | Green | |
| 6,902,705 B1 | 6/2005 | Caillat et al. | |
| 7,163,823 B2 | 1/2007 | Patno et al. | |
| 7,344,877 B1 | 3/2008 | Camacho et al. | |
| 7,439,056 B2 | 10/2008 | Duffy et al. | |
| 7,666,362 B2 | 2/2010 | Shanler | |
| 7,794,799 B1 | 9/2010 | Kim | |
| 7,854,343 B2 | 12/2010 | Ellson et al. | |
| 7,858,044 B2 | 12/2010 | Coassin et al. | |
| 8,221,697 B2 | 7/2012 | Nichols et al. | |
| 8,337,778 B2 | 12/2012 | Stone et al. | |
| 8,987,174 B2 | 3/2015 | Routenberg | |
| 2001/0036424 A1 | 11/2001 | Takahashi | |
| 2002/0016009 A1 | 2/2002 | Ogura | |
| 2002/0064482 A1 | 5/2002 | Tisone et al. | |
| 2002/0094533 A1 | 7/2002 | Hess | |
| 2002/0159919 A1 | 10/2002 | Churchill et al. | |
| 2003/0032046 A1 | 2/2003 | Duffy et al. | |
| 2003/0083474 A1 | 5/2003 | Schmidt | |
| 2003/0113813 A1 | 6/2003 | Heidaran et al. | |
| 2003/0124599 A1 | 7/2003 | Chen | |
| 2003/0148401 A1 | 8/2003 | Agrawal et al. | |
| 2003/0209560 A1 | 11/2003 | Hui et al. | |
| 2004/0106156 A1 | 6/2004 | Perez | |
| 2004/0106191 A1 | 6/2004 | Muser | |
| 2004/0136876 A1 | 7/2004 | Fouillet et al. | |
| 2004/0142460 A1 | 7/2004 | Cima | |
| 2004/0208792 A1 | 10/2004 | Linton et al. | |
| 2004/0234966 A1 | 11/2004 | Bryning | |
| 2005/0045539 A1 | 3/2005 | Yu et al. | |
| 2005/0058577 A1 | 3/2005 | Micklash, II et al. | |
| 2005/0079105 A1 | 4/2005 | Hunter et al. | |
| 2005/0084423 A1 | 4/2005 | Zarowitz | |
| 2005/0186579 A1 | 8/2005 | Dellinger | |
| 2006/0013031 A1 | 1/2006 | Ravkin et al. | |
| 2006/0051249 A1 | 3/2006 | Knebel et al. | |
| 2006/0078893 A1 | 4/2006 | Griffiths | |
| 2006/0105453 A1 | 5/2006 | Brenan et al. | |
| 2006/0105462 A1 | 5/2006 | Sellek-Prince | |
| 2006/0142468 A1 | 6/2006 | Downing, Jr. et al. | |
| 2006/0211132 A1 * | 9/2006 | Miledi | B01J 19/0046 436/180 |
| 2007/0003448 A1 | 1/2007 | Kanigan et al. | |
| 2007/0005169 A1 | 1/2007 | Rohnert et al. | |
| 2007/0077651 A1 | 4/2007 | Guarino | |
| 2007/0099208 A1 | 5/2007 | Drmanac | |
| 2007/0117765 A1 | 5/2007 | Sauve et al. | |
| 2008/0003671 A1 | 1/2008 | Martin | |
| 2008/0173544 A1 | 7/2008 | Seul | |
| 2009/0032064 A1 | 2/2009 | Gifford et al. | |
| 2009/0090173 A1 | 4/2009 | Fukuda et al. | |
| 2009/0142564 A1 | 6/2009 | Plissonnier et al. | |
| 2009/0148348 A1 | 6/2009 | Pettigrew et al. | |
| 2009/0227474 A1 | 9/2009 | Gordon et al. | |
| 2009/0286317 A1 | 11/2009 | Demmler et al. | |
| 2010/0000304 A1 | 1/2010 | Kim et al. | |
| 2010/0167950 A1 | 7/2010 | Juang et al. | |
| 2010/0297767 A1 | 11/2010 | Hattori et al. | |
| 2011/0171087 A1 * | 7/2011 | Delmotte | B01F 25/451 422/514 |
| 2012/0198928 A1 | 8/2012 | Streit et al. | |
| 2012/0220497 A1 | 8/2012 | Jacobson et al. | |
| 2015/0018248 A1 | 1/2015 | Kim | |
| 2016/0169867 A1 | 6/2016 | Khine et al. | |
| 2016/0176191 A1 * | 6/2016 | Kuramochi | B41J 2/04596 347/70 |
| 2016/0332155 A1 | 11/2016 | Schoeneck et al. | |
| 2016/0361006 A1 * | 12/2016 | Bullington | B01L 3/0217 |
| 2017/0153165 A1 * | 6/2017 | Nwadigo | B01L 3/0231 |
| 2018/0128718 A1 * | 5/2018 | Crum | A61B 10/0096 |
| 2018/0220945 A1 * | 8/2018 | Sink | A61B 5/150503 |

FOREIGN PATENT DOCUMENTS

| | | |
|---|---|---|
| CN | 101031363 A | 9/2007 |
| DE | 10043042 | 3/2002 |
| EP | 0812693 A1 | 12/1997 |
| EP | 1348533 B1 | 7/2002 |
| EP | 1358939 A2 | 4/2003 |
| EP | 1386657 A1 | 2/2004 |
| EP | 1399263 B1 | 3/2004 |
| EP | 1473079 A1 | 11/2004 |
| EP | 1788047 A1 | 8/2005 |
| EP | 1683571 A1 | 1/2006 |
| EP | 1316360 B1 | 9/2006 |
| GB | 1291610 | 10/1972 |
| GB | 2332273 A | 6/1999 |
| GB | 2334954 A | 9/1999 |
| JP | 3120453 B2 | 12/2000 |
| JP | 2002-502955 A | 1/2002 |
| JP | 2003-033177 A | 2/2003 |
| JP | 2004-020280 A | 1/2004 |
| JP | 2004-077476 A | 3/2004 |
| JP | 2004-535176 A | 11/2004 |
| JP | 2005-003803 A | 1/2005 |
| JP | 2005-099004 A | 4/2005 |
| WO | WO 1996-23879 | 8/1996 |
| WO | WO 98/04358 A1 | 2/1998 |
| WO | WO 1998-055852 | 12/1998 |
| WO | WO 99/39829 A1 | 8/1999 |
| WO | WO 2000-014311 | 3/2000 |
| WO | WO 00-58735 | 10/2000 |
| WO | WO 99/55826 | 10/2000 |
| WO | WO 2001/004144 A2 | 1/2001 |
| WO | WO 2003-029462 A1 | 4/2003 |
| WO | WO 2004-030820 A2 | 4/2004 |
| WO | WO 2004-111610 A2 | 12/2004 |
| WO | WO 2005/019254 A1 | 3/2005 |
| WO | WO 2005/019255 A1 | 3/2005 |
| WO | WO 2005/019256 A2 | 3/2005 |
| WO | WO 2006/004739 A2 | 1/2006 |
| WO | WO 2006/046699 A1 | 5/2006 |
| WO | WO 2007/102785 A1 | 9/2007 |
| WO | WO 2008/063136 A1 | 5/2008 |

(56) References Cited

FOREIGN PATENT DOCUMENTS

| WO | WO 98/47003 | 10/2008 |
|----|-------------|---------|
| WO | WO 2010/120249 A1 | 10/2010 |
| WO | WO 2012/011877 A2 | 1/2012 |

OTHER PUBLICATIONS

Curiox Biosystems PTE Ltd., International Preliminary Reporton Patentability, PCT/US2020/033251, dated Jun. 4, 2021, 26 pgs.
Curiox, International Preliminary Report on Patentability, PCT/IB2018/000436, dated Oct. 8, 2019, 11 pgs.
Curiox, International Search Report/Written Opinion, PCT/IB2018/000436, dated Sep. 7, 2018, 14 pgs.
Curiox, Extended Search Report, EP Application No. 18781680.6, dated Jan. 14, 2021, 8 pgs.
Agency for Science, Technology and Research, International Preliminary Report on Patentability, PCT/SG2007/000393, dated May 26, 2009, 4 pgs.
Agency for Science, Technology and Research, International Search Report and Written Opinion of the ISA, PCT/SG2007/000393, dated Feb. 20, 2008, 4 pgs.
Agency for Science, Technology and Research, Communication Pursuant to Article 94, EP07835548-4, dated Jul. 17, 2015, 3 pgs.
Agency for Science, Technology and Research, Communication Pursuant to Article 94, EP07835548-4, dated Oct. 2, 2018, 3 pgs.
Agency for Science, Technology and Research, Notification of First Office Action, CN 201110401674.9, dated Dec. 30, 2013, 9 pgs.
Agency for Science, Technology and Research, First Examination Report, IN3674/CHEN/P2009, dated Oct. 7, 2016, 9 pgs.
Agency for Science, Technology and Research, Notification of Reasons for Refusal, JP 2009-538373, dated Nov. 10, 2011, 7 pgs.
Agency for Science, Technology and Research, Notification of Reasons for Refusal, JP 2012-196318, dated Dec. 10, 2013, 3 pgs.
Agency for Science, Technology and Research, Notification of the Second Office Action, CN 200780048922.8, dated May 17, 2011, 4 pgs.
Agency for Science, Technology and Research, Notification on the Grant of Patent Right for Invention, CN 200780048922.8, dated Sep. 22, 2011, 1 pg.
Agency for Science, Technology and Research, Supplementary Search Report, EP 07835548.4, dated Jun. 30, 2010, 4 pgs.
Asberg, Surgace Energy Modified Chips for Detection of Conformational States and Enzymatic Activity in Biomolecules, Langmuir, 2006, pp. 2205-2211.
Beck, Improving Stamps for 10 nm Level Wafer Scale Nanoimprint Lithography, Microelectron. Eng., 2002, pp. 61-62 and 441.
Benor, Microstructuring by Microcontact Printing and Selective Surface Dewetting, J. of Vacuum Science & Technology B, 2007, pp. 1321-1326.
Beste, Small Antibody-like Proteins with Prescrived Ligand Specificities Derived from the Lipocalin Fold, Proc. Natl. Acad. Sci, USA, 1999, pp. 1898-1903.
Biffinger, The Polar Hydrophobicity of Cluorinated Compounds, ChemBioChem, 2004, pp. 622-627.
Burbulis, Quantifying Small Numbers of Antibodies with a 'Near-Universal' Protein-DNA Chimera, Nature Methods, Nov. 2007, 39 pgs.
Cheng, Office Action, U.S. Appl. No. 14/050.321, dated Feb. 26, 2016, 31 pgs.
Cheng, Office Action, U.S. Appl. No. 14/050,321, dated Mar. 31, 2017, 38 pgs.
Cheng, Final Office Action, U.S. Appl. No. 14/050,321, dated Jan. 24, 2018, 33 pgs.
Chiriac, Magnetic GMI Sensor for Detection of Biomolecules, J. Magnetism and Magnetic Materials, 2005, pp. 671-676.
Churaev, Wetting of Low-Energy Surgfaces, Advances in Colloid and Interface Science, 2007, pp. 134-135, 15-23.
Curiox Biosystems Pte Ltd., International Preliminary Report on Patentability, PCT/SG2010/000153, dated Oct. 18, 2011, 15 pgs.
Curiox Biosystems Pte Ltd., International Preliminary Report on Patentablity, PCT/IB2013/000623, dated Aug. 5, 2014, 7 pgs.
Curiox Biosystems Pte Ltd., International Search Report and Written Opinion, PCT/SG2006/000050, dated May 8, 2006, 6 pgs.
Curiox Biosystems Pte Ltd., International Search Report and Written Opinion, PCT/SG2010/000153, dated Sep. 17, 2010, 20 pgs.
Curiox Biosystems Pte Ltd., International Search Report and Written Opinion, PCT/SG2011/000263, dated Feb. 29, 2012, 18 pgs.
Curiox Biosystems Pte Ltd., International Search Report and Written Opinion, PCT/US2015/019760, dated Jun. 2, 2015, 12 pgs.
Daniel, Vibration-Actuated Drop Motion on Surfaces bor Batch Microfluidic Processes, Langmuir, 2005, pp. 4220-4228.
Dill, Modeling Water, The Hydrophobic Effect and Ion Solvation, Annu. Rev. Biophys. Biomol. Struc, 2005, pp. 173-199.
Erfle et al., "Reverse Transfections on Cell Arrays for High Content Screening Microscopy," Nature Protocols, Mar. 1, 2007, vol. 2 No. 2, 8 pgs.
Gao, A Commercially Available Perfectly Hydrophobic Material, Langmuir, 2007, pp. 9125-9127.
Gascoyne, Dielectrophoresis-based Programmable Fluidic Processors, Lab-on-a-Chip, 2004, pp. 299-309.
Genua, Functional Patterns Obtained by Nanoimprinting Lithography and Subsequent Growth of Polymer Brushes, Nanotechnology, 2007, 215301, 7 pgs.
Gill, Pharmaceutical Drug Discovery Using Novel Protein Scaffolds, Current Opinion in Biotechnology, 2006, 653-658.
Giovambattista, Effect of Surface Polarity on Water Contact Angle and Interfacial Hydration Structure, J. Phys. Chem., 2007, pp. 9581-9587.
Goddard, Polymer Surface Modification for the Attachment of Bioactive Compounds, Progress in Polymer Science, 2007, pp. 698-725.
Griffiths, Miniaturising the Laboratory in Emulsion Droplets, Trends in Biotechnology, 2006, pp. 395-402.
Herrmann, Enxymatically-Generated Fluorescent Detection in Micro-Channels with Internal Magnetic Mixing for the Development of Parallel Miicrofluidic ELISA, Lab-on-a-Chip, 2006, pp. 555-560.
Holt, Domain Antibodies: Proteins for Therapy, Trends Biotechnol, 2003, pp. 484-490.
Hutten, New Magnetic Nanoparticles for Biotechnology, J. Biotech., 2004, pp. 47-63.
Iliades, Triabodies: Single Chain Fv Fragments without a Linker Form Trivalent Trimers, FEBS Lett, 1997, pp. 437-441.
Jakobs, Micrometer Scale Gel Patterns, Colloids & Surfaces A: PhysioChem. Eng. Aspects, 2006, pp. 33-40.
Jung, Wetting Transition of Water Droplets on Superhydrophobic Patterned Surfaces, Scripta Materialia, 2007, pp. 1057-1060.
Kanta, Preparation of Silica-on-Titania Patterns with a Wettability Contrast, Langmuir, 2005, 5790-5794.
Kim, Final Office Action, U.S. Appl. No. 13/264,913, dated Jun. 21, 2013, 11 pgs.
Kim, Notice of Allowance, U.S. Appl. No. 12/282,162, dated May 14, 2012, 7 pgs.
Kim, Office Action, U.S. Appl. No. 12/282,162, dated Jun. 27, 2011, 8 pgs.
Kim, Office Action, U.S. Appl. No. 13/264,913, dated Nov. 7, 2012, 9 pgs.
Kim, Office Action, U.S. Appl. No. 13/264,913, dated Sep. 26, 2013, 10 pgs.
Kim, Office Action, U.S. Appl. No. 13/811,638, dated Sep. 11, 2015, 29 pgs.
Kim, Final Office Action, U.S. Appl. No. 13/811,638, dated Apr. 21, 2016, 24 pgs.
Kim, Final Office Action, U.S. Appl. No. 13/811,638, dated Feb. 9, 2017, 29 pgs.
Kim, Office Action, U.S. Appl. No. 14/326,780, dated Oct. 28, 2015, 13 pgs.
Kim, Final Office Action, U.S. Appl. No. 14/326,780, dated May 10, 2016, 11 pgs.
Kim, Notice of Allowance, U.S. Appl. No. 14/326,780, dated Sep. 22, 2016, 7 pgs.
Kim, Office Action, U.S. Appl. No. 14/452,172, dated Oct. 23, 2015, 16 pgs.

(56) References Cited

OTHER PUBLICATIONS

Kim, Final Office Action, U.S. Appl. No. 14/452,172, dated Jun. 3, 2016, 17 pgs.
Kim, Notice of Allowance, U.S. Appl. No. 14/452,172, dated Dec. 12, 2017, 9 pgs.
Kim, Office Action, U.S. Appl. No. 14/338,168, dated Nov. 6, 2015, 8 pgs.
Kim, Office Action, U.S. Appl. No. 14/338,168, dated Jun. 22, 2016, 9 pgs.
Kim, Notice of Allowance, U.S. Appl. No. 14/338,168, dated Sep. 13, 2017, 8 pgs.
Kusumaatmaja, Controlling Drop Size and Polydispersity Using Chemically Patterned Surfaces, Langmuir, 2007, pp. 956-959.
Kwon, Quantitative Evaluation of the Relative Cell Permeability of Peptoids and Peptides, J. Am. Chem. Soc., 2007, pp. 1508-1509.
Leek, Final Office Action, U.S. Appl. No. 11/984,197, dated May 8, 2012, 10 pgs.
Leek, Office Action, U.S. Appl. No. 11/984,197, dated Mar. 14, 2013, 11 pgs.
Leek, Office Action, U.S. Appl. No. 11/984,197, dated May 26, 2011, 11 pgs.
Leek, Office Action, U.S. Appl. No. 11/984,197, dated Jul. 31, 2013, 12 pgs.
Leek, Notice of Allowance, U.S. Appl. No. 14/246,004, dated Sep. 15, 2016, 8 pgs.
Leek, Office Action, U.S. Appl. No. 15/424,604, dated Aug. 11, 2017, 7 pgs.
Li, What Do We Need for a Superhydrophobic surface? A review on the recent progress in the preparation of superhydrophobic surfaces, Chem. Soc. Rev, 2007, pp. 1350-1368.
Lowe et al., "Perfluorochemicals: Their Applications and Benefits to Cell Culture," Tibtech, Jun. 1998, vol. 16, 6 pgs.
Luca, Preparation of TIOx Thin Films by Reactive Pulsed-Laser Ablation, J. Optoelectronics and Adv. Materials, Apr. 2005, pp. 625-630.
Lundgren, Modeling of Wetting: A Study of Nanowetting at Rough and Heterogeneous Surfaces, Langmuir, 2007, pp. 1187-1194.
Ma, Superhydrophobic Surfaces, Current Opinion in Colloid & Interface Science, 2006, pp. 193-202.
Mardare, Microelectrochemical Lithography: A method for Direct Writing of Surface Oxides, Electrochimica Acta, 2007, pp. 7865-7869.
Matsuda, Phosphorylcholine-Endcapped Oligomer and Block Co-Oligomer and Surface Biological Reactivity, Biomaterials, 2003, pp. 4517-4527.
Meyer, Recent Progress in Understanding Hydrophobic Interactions, Proc. Netl. Acad. Sci USA, 2006, pp. 15739-15746.
Mosavi, The Ankyrin Repeat as Molecular Architecture for Protein Recognition, Protein Science, 2004, pp. 1435-1448.
Opdahl, Polymer Surface Science, The Chemical Record, 2001, pp. 101-122.
Perfulorodecalin-FluoroMed, downloaded on Sep. 5, 2013, from http://fluoromed.com/products/perfluorodecalin.html, 1 pg.
Pollack, Electrowetting-based Actuation of Liquid Droplets for Microfluidic Applications, Appl. Phys. Lett., 2000, pp. 1725-1726.
Popp, Sortagging: A versatile Method for Protein Labeling, Nature Chemical Biology, 2007, pp. 707-708.
Rastogi, Development and Evaluation of Realistic Microbioassys in Freely Suspended Droplets on a Chip, Biomicrofludics, 2007, 014107-1-014107-17.
Roach, Controllling Nonspecific Protein Adsorption in a Plug-Based Microfluidic System by Controlling Interfacial Chemistry Using Fluorous-Phase Surfactants, Analytical Chemistry, vol. 77, No. 3, Feb. 1, 2005, pp. 785-796.
Ronaghi, Pyrosequestering Sheds Light on DNA Sequestering, Genome Research, 2001, pp. 3-11.
Rose, Microdispensing Technologies in Drug Discovery, Drug Discovery Today, 1999, pp. 411-419.
Satriano, Bacterial Adhesion Onto Nanopatterned Polymer Surfaces, Materials Science & Engineering C, 2006, pp. 942-946.
Silverman, Multivalent Avimer Proteins Evolved by Exon Shuffling of a Family of Human Receptor Domains, Nature Biotechnology, 2005, pp. 1556-1561.
Skerra, Engineered Protein Scaffolds for Molecular Recognition, J. Mol. Recognit., 2000, pp. 167-187.
Song, Miniature Biochip System for Detection of Sscherichi coli O157:H7 Based on Antibody-Immobilized Capillary Reactors and Enzyme-linked Immunosorbent Assay, Analytica Chimica Acta, 2004, pp. 115-121.
Stephenson, Quantifying the Hydrophobic Effect: A Computer Simulation-Molecular-Thermodynamic Model for the Self-Assembly of Hydrophibic and Amphiphilic Solutes in Aqueous Solution, Jp. Phys. Chem. B, 2007, 1025-1044.
Stone, The Assembly of Single Domain Antibodies into Bispecific Decavalent Molecules, J. Immunological Methods, 2007, pp. 88-94.
Sundberg, Contact Angle Measurements by Confocal Microscopy for Non-Destructive Microscale Surface Characterization, J. Colloid and Interface Science, 2007, pp. 454-460.
Takahashi et al., Induction of Pluripotent Stem Cells from Mouse Embryonic and Adult Fibroblast Cultures by Defined Factors, Cell, Aug. 25, 2006, 126, 14 pgs.
Vancha et al., "Use of Polyethyleneimine Polymer in Cell Culture as Attachment Factor and Lipofection Enhancer," BMC Biotechnology, Oct. 15, 2004, 12 pgs.
Van Oss, Long-Rage and Short-Range Mechanisms of Hydrophobic Attraction and Hydrophilic Repulsion in Specific and Aspecific Interactions, J. Mol. Recognit., 2003, pp. 177-190.
Wang, Flow-Focusing Generation of Monodisperse Water Droplets Wrapped by Ionic Liquid on Microfluidic Chips: From Plug to Sphere, langmuir, 2007, pp. 11924-11931.
Wang, In-Situ Wilhelmy Balance Surface Energy Determination of Poly(3-hexylthiophere) and Poly(3,4-ethylenedioxythiophere) during Electrochemical Doping-Dedoping, Langmuir, 2006, pp. 9287-9294.
Washizu, Elecrostatic Actuation of Liquid Droplets for Microreactor Applications, IEEE Transactions on Industry Applications, vol. 34, No. 4, Jul.-Aug. 1998.
West, Microplasma Writing for Surface-Directed Millifludics, Lab-on-a-Chip, 2007, pp. 981-983.
Widom, The Hydrophobic Effect, Phys. Chem. Chem. Phys., 2003, pp. 3085-3093.
Wixforth, Flatland Fluidics, mstnews, 2002, pp. 42-43.
Agency for Science, Technology and Research, Decision to Grant, Application No. CN201110401674.9, dated Aug. 7, 2014, 4 pgs.
Agency for Science, Technology and Research, Decision to Grant, JP2012-196318, dated Sep. 12, 2014, 5 pgs.
Agency for Science, Technology and Research, Notification of the First Office Action, CN 200780048922.8, dated Nov. 12, 2010, 7 pgs.
Curiox Biosystems Pte Ltd, International Preliminary Report on Patentability, PCT/SG2011/000263, dated Dec. 21, 2012, 18 pgs.
Curiox Biosystems Pte Ltd, International Search Report and Written Opinion, PCT/IB2013/000623, dated Jul. 10, 2013, 10 pgs.
Office Action, KR 10-2019-7032755, dated Jan. 28, 2022, 12 pgs.
Curiox Biosystems Pte Ltd, EP18781680, Decision to grant a European patent, dated May 8, 2023, 4 pgs.

\* cited by examiner

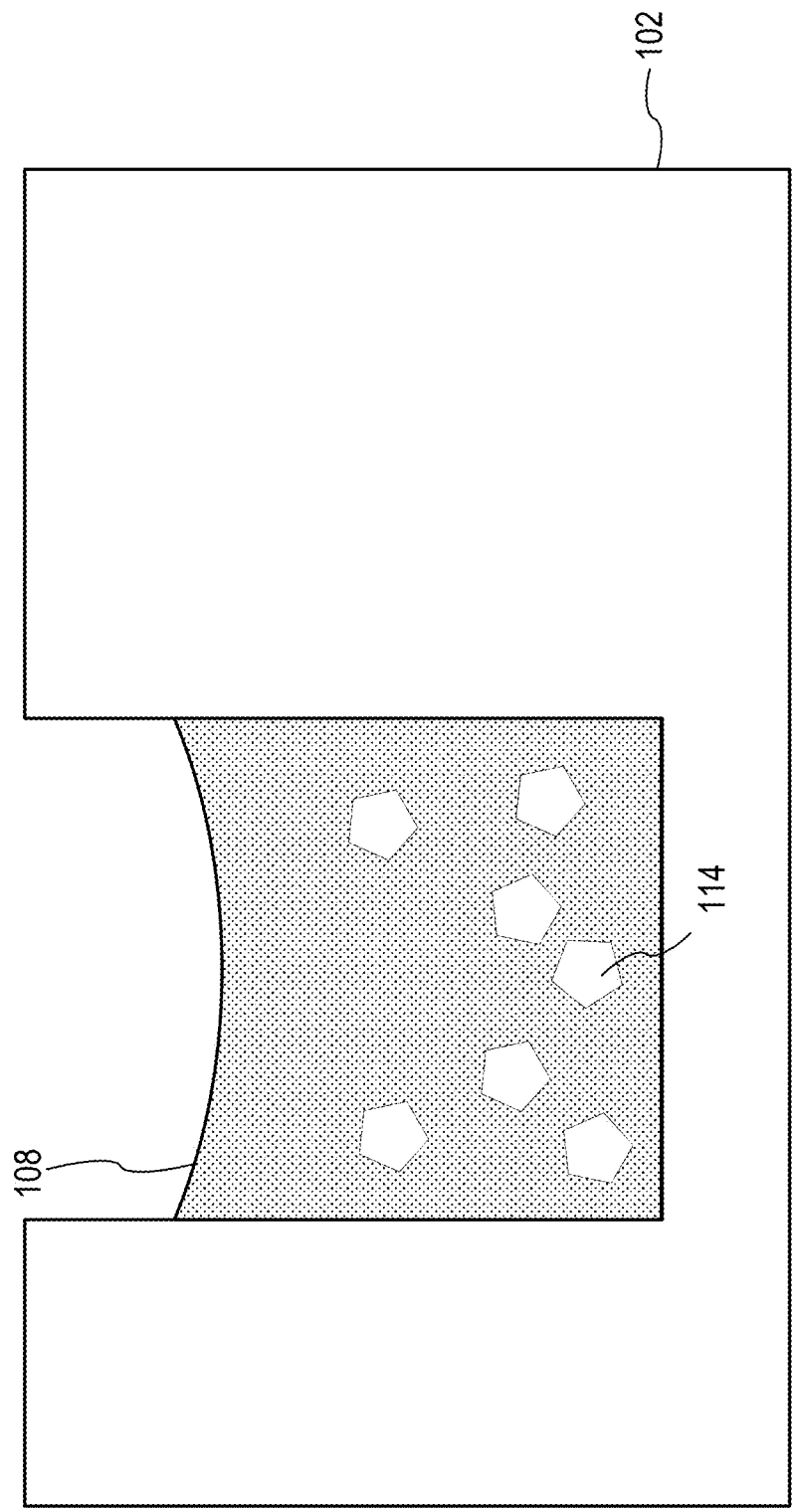

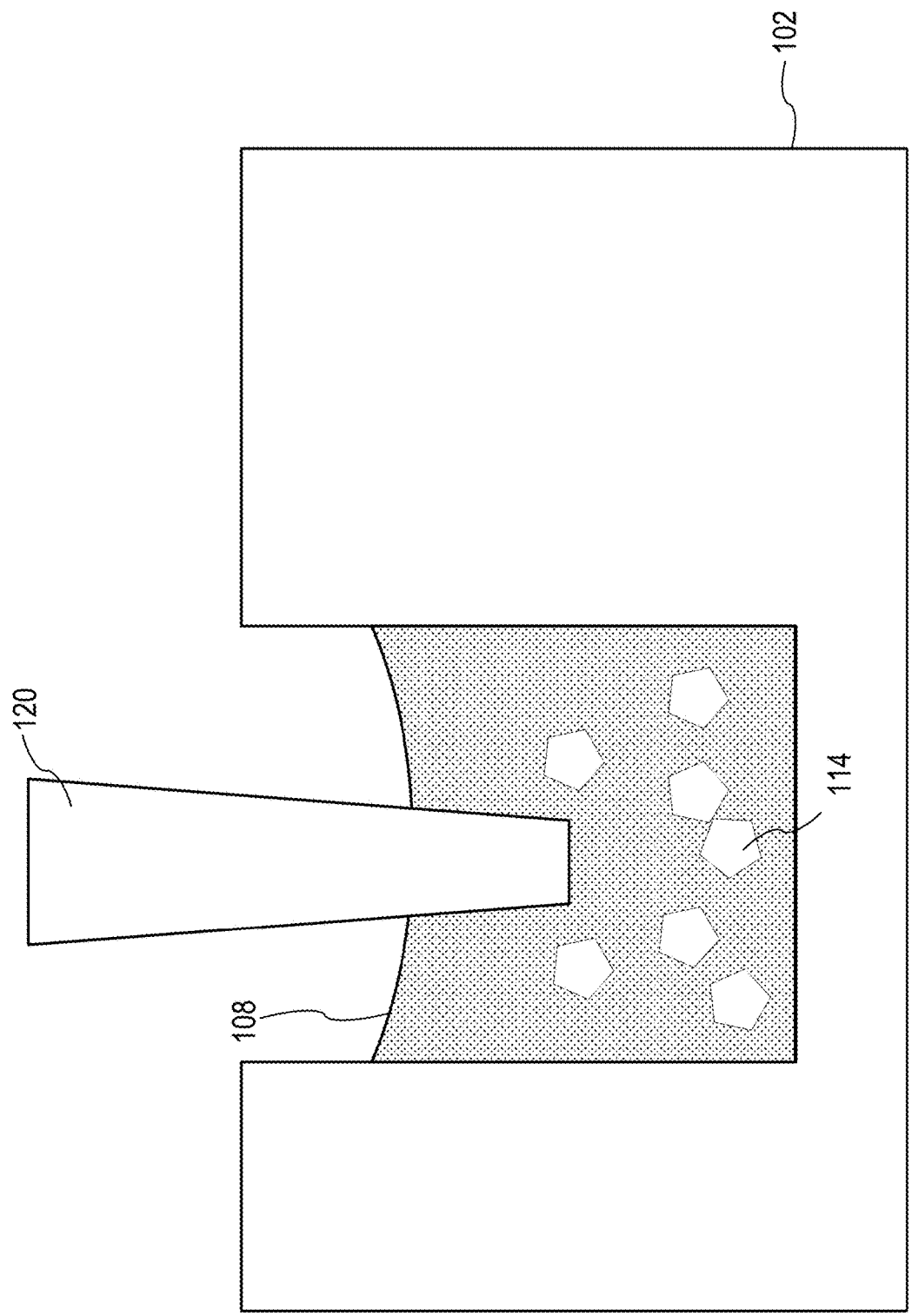

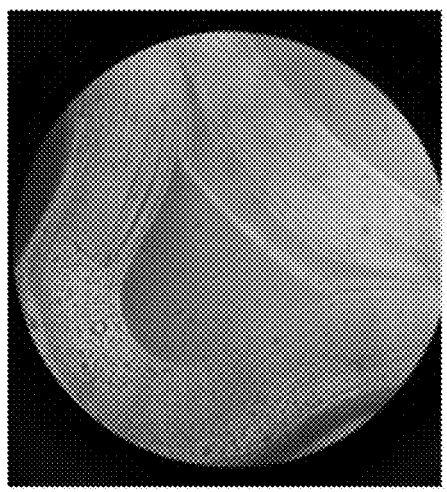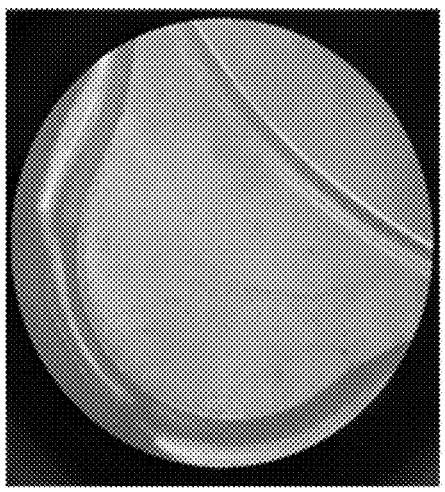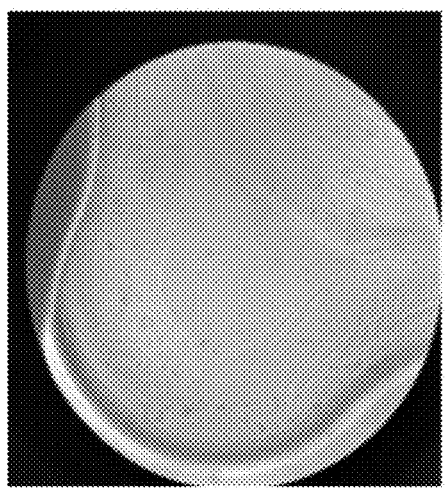
Figure 7C                              Figure 7D

METHODS, DEVICES, AND APPARATUS FOR WASHING SAMPLES ON ARRAY PLATES

RELATED APPLICATIONS

This application is a continuation application of International Patent Application No. PCT/IB2018/000436, filed Apr. 5, 2018, which claims the benefit of, and priority to, U.S. Provisional Patent Application Ser. No. 62/482,140, filed Apr. 5, 2017, U.S. Provisional Patent Application Ser. No. 62/517,166, filed Jun. 9, 2017, and U.S. Provisional Patent Application Ser. No. 62/517,788, filed Jun. 9, 2017. All of these applications are incorporated reference herein in their entireties.

TECHNICAL FIELD

The disclosed embodiments relate generally to methods, devices, and apparatus for washing samples (e.g., cells, particles, etc.). More particularly, the disclosed embodiments relate to methods, devices, and apparatus for washing samples on array plates and slides.

BACKGROUND

An array plate is also called a microtiter plate, microplate, or microwell plate. Array plates are typically used to hold respective liquid droplets separately for biological and/or chemical reaction. For example, a well-type array plate includes a plurality of wells so that each liquid droplet or each sample may be dispensed into a separate well for further processing. Typically, the number of wells is selected from 6, 24, 96, 384, 1536, 3456, and 9600.

Samples (e.g., cells) are frequently washed. Washing typically involves adding a wash solution to a sample solution, including samples (e.g., cells), on the slide and removing the mixture of the wash solution and the sample solution. By repeating the dilution and partial removal of the sample solution, the concentration of chemicals and/or biological reagents other than the samples are reduced. However, certain cells (e.g., suspension cells, non-adherent cells, and weakly adherent cells) do not strongly adhere to the slide. Thus, during removal of the mixture, cells may be removed along with the mixture, thereby reducing the number of cells that remain on the hydrophilic area of the slide after the washing. Because a reliability of cell-based reactions typically requires a sufficient number of cells, the loss of cells during washing negatively affects cell-based reactions.

In addition, variations in the sample washing increase measurement errors, which are not desirable for accurate assays.

SUMMARY

Accordingly, there is need for methods, devices, and apparatus that better retain cells during washing. Such methods, devices, and apparatus plates may replace the conventional methods, devices, and apparatus for washing cells. Such methods, devices, and apparatus reduce or eliminate the loss of cells during washing, thereby improving the reliability of cell-based reactions. Similarly, such methods, devices, and apparatus may be used in washing other types of samples, such as beads or particles conjugated with target molecules. In addition, such methods, devices, and apparatus improve the accuracy in assays and reduce the time required for washing samples.

A number of embodiments that overcome the limitations and disadvantages of existing methods, devices, and apparatus are presented in more detail below. These embodiments provide methods, devices, and apparatus for washing a sample in a solution.

As described in more detail below, in accordance with some embodiments, an apparatus for washing an array plate includes one or more dispensers. A respective dispenser of the one or more dispensers is configured to dispense a first liquid on the array plate. The respective dispenser includes a first piston configured to slide at least partially within a first channel; and a first valve configured to allow the first liquid in the first channel to be dispensed from the first channel through the first valve and prevent a liquid from entering into the first channel through the first valve.

In accordance with some embodiments, an apparatus for washing an array plate includes one or more aspirators. A respective aspirator of the one or more aspirators is configured to aspirate a liquid on an array plate. The respective aspirator includes a piston configured to slide at least partially within a channel; and a valve configured to allow the liquid on the array plate to be aspirated into the channel through the valve and prevent a liquid in the channel from exiting from the channel through the valve.

In accordance with some embodiments, an apparatus for washing an array plate includes one or more dispensers, a respective dispenser of the one or more dispensers configured to dispense a first liquid on the array plate; and one or more aspirators that are distinct from the one or more dispensers, a respective aspirator of the one or more aspirators including a positive displacement pump configured to aspirate liquid on the array plate.

In accordance with some embodiments, a method for washing a sample includes obtaining an array plate that includes an array of hydrophilic areas surrounded by one or more hydrophobic areas. A respective solution containing a sample is located on a respective hydrophilic area of the array of hydrophilic areas. The respective hydrophilic area includes one or more indentations from a respective surrounding hydrophobic area of the one or more hydrophobic areas. The respective hydrophilic area includes a first indented surface that is offset from a reference surface defined by the respective surrounding hydrophobic area. The method also includes placing an aspirator nozzle above the respective hydrophilic area at least 100 µm from the first indented surface; and aspirating the solution with the aspirator nozzle while the aspirator nozzle is located at least 100 µm from the first indented surface.

In accordance with some embodiments, an apparatus is configured for performing any method described herein.

In accordance with some embodiments, a device for washing a sample includes a plate having an array of hydrophilic areas; and one or more hydrophobic areas surrounding the array of hydrophilic areas. A respective hydrophilic area of the array of hydrophilic areas is offset from a surrounding hydrophobic area of the one or more hydrophobic areas. The respective hydrophilic area includes a primary area and two or more secondary areas that extend from the primary area on a plane defined by the primary area.

BRIEF DESCRIPTION OF THE DRAWINGS

For a better understanding of the aforementioned embodiments as well as additional embodiments, reference should be made to the Description of Embodiments below, in conjunction with the following drawings in which like reference numerals refer to corresponding parts throughout the figures.

FIGS. 1A-1F illustrate a washing operation with a conventional micro-titer plate.

FIG. 7C shows results of washing operations performed with an array plate without filleted corners in accordance with some embodiments.

FIG. 7D shows results of washing operations performed with an array plate with filleted corners in accordance with some embodiments.

Like reference numerals refer to corresponding parts throughout the drawings.

DESCRIPTION OF EMBODIMENTS

Methods, devices, and apparatus for washing samples are described. Reference will be made to certain embodiments, examples of which are illustrated in the accompanying drawings. While the claims will be described in conjunction with the embodiments, it will be understood that it is not intended to limit the claims to these particular embodiments alone. On the contrary, the embodiments are intended to cover alternatives, modifications and equivalents that are within the spirit and scope of the appended claims.

Moreover, in the following description, numerous specific details are set forth to provide a thorough understanding of the embodiments. However, it will be apparent to one of ordinary skill in the art that the embodiments may be practiced without these particular details. In other instances, methods, procedures, components, and networks that are well-known to those of ordinary skill in the art are not described in detail to avoid obscuring aspects of the embodiments.

It will also be understood that, although the terms first, second, etc. may be used herein to describe various elements, these elements should not be limited by these terms. These terms are only used to distinguish one element from another. For example, a first piston could be termed a second piston, and, similarly, a second piston could be termed a first piston, without departing from the scope of the embodiments. The first piston and the second piston are both pistons, but they are not the same piston.

The terminology used in the description of the embodiments herein is for the purpose of describing particular embodiments only and is not intended to be limiting of the invention. As used in the description of the embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, a liquid droplet refers to an aliquot of a liquid. A droplet may have any shape, and the term "droplet" is not used herein to describe a particular shape.

FIGS. 1A-1F illustrate a washing operation with a conventional micro-titer plate.

Figure 1A:
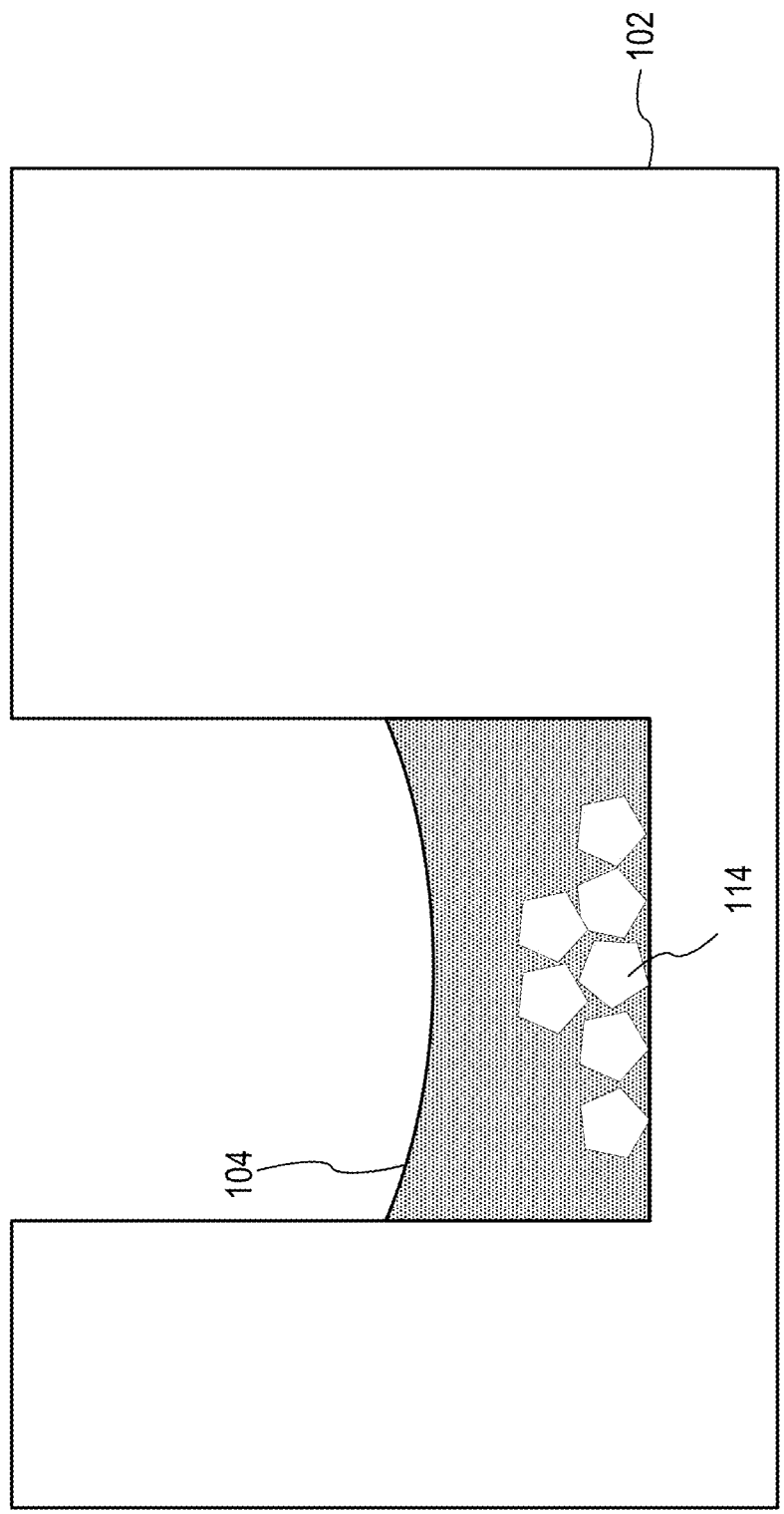

FIG. 1A illustrates solution 104 containing samples 114 (e.g., cells, particles, etc.) in a well that is defined in micro-titer plate 102.

Figure 1B:
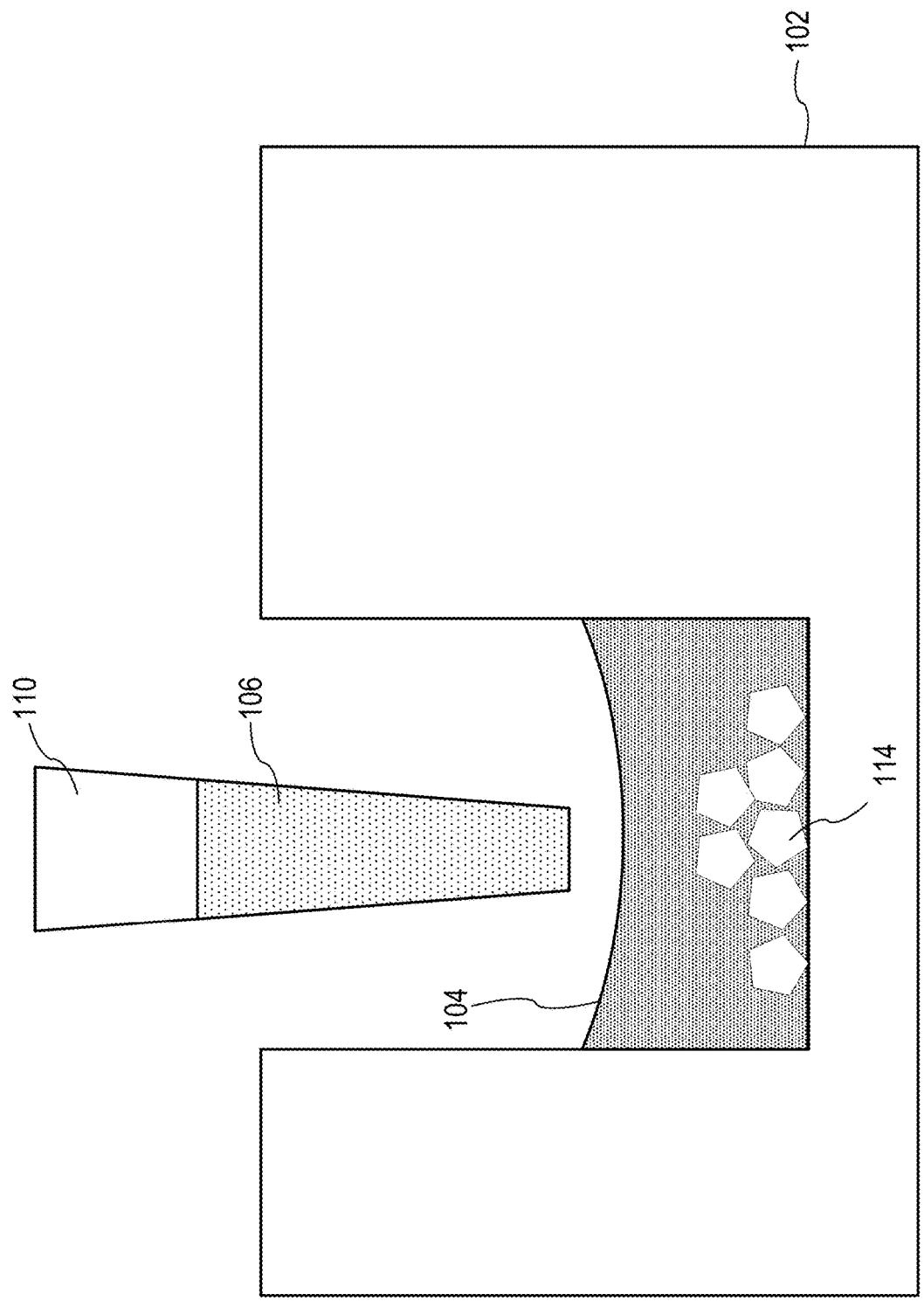

FIG. 1B illustrates that dispenser 110 containing wash liquid 106 (e.g., a wash buffer, such as phosphate-buffered saline, Tris-buffered saline, borate-buffered saline, and TE buffer) is used for washing samples 114.

Figure 1C:
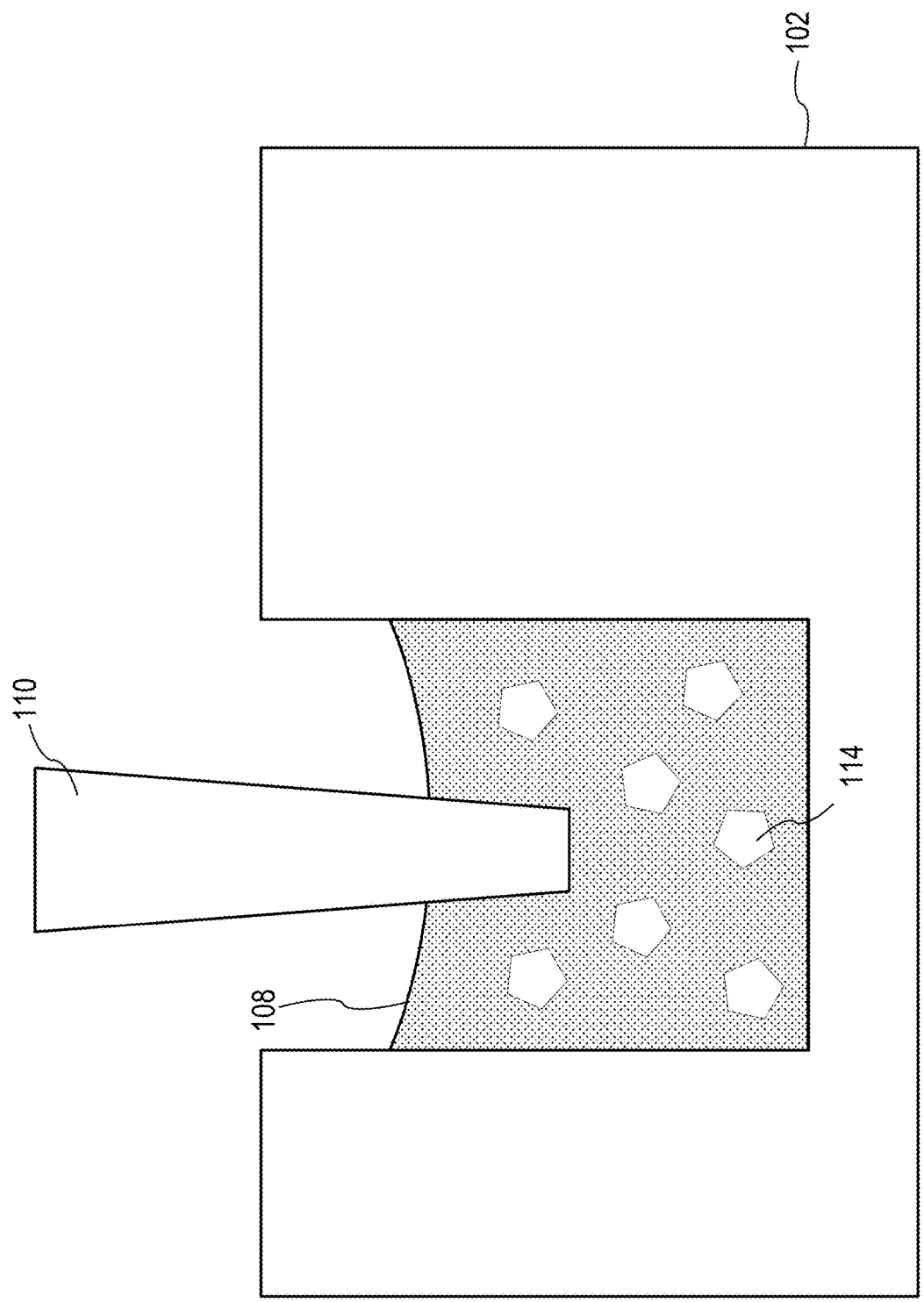

For example, as shown in FIG. 1C, wash liquid 106 in dispenser 110 is dispensed into solution 104, thereby forming mixture 108 (e.g., liquid) of solution 104 and wash liquid 106. As a result, chemical and biological reagents in solution 104 are diluted (e.g., concentrations of chemicals and biological reagents in solution 104 are reduced). FIG. 1C also illustrates that at least a portion of samples 114 is lift-off from the bottom of the well and suspended in mixture 108, due to the liquid flow caused by introduction of wash liquid 106 into solution 104.

FIG. 1D illustrates that samples 114 settle over time.

FIG. 1E illustrates that aspirator 120 is used to aspirate (e.g., remove) a portion of mixture 108.

Figure 1F:
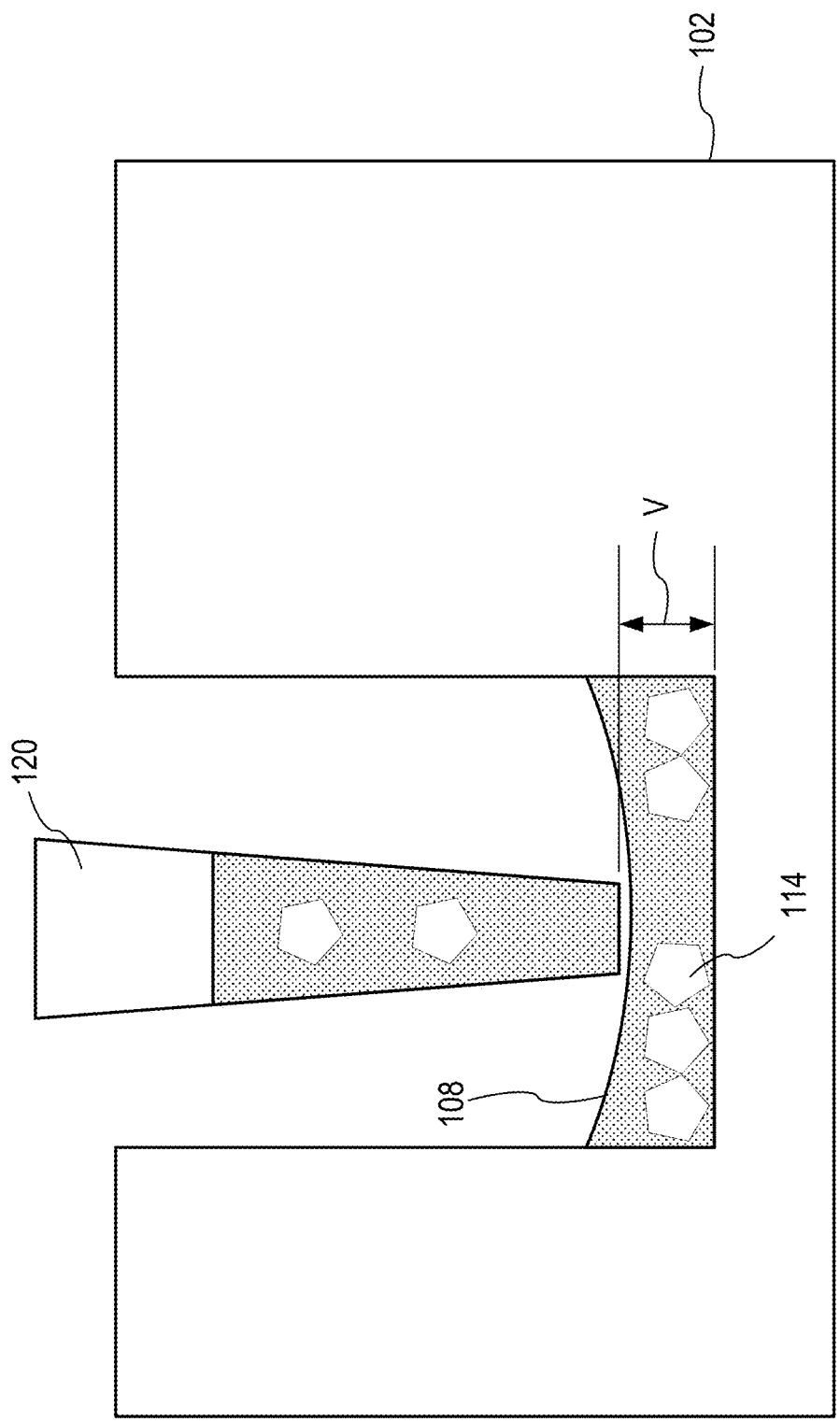

FIG. 1F illustrates that aspirator 120 has aspirated a portion of mixture 108. The volume of mixture 108 remaining in the well defined in micro-titer plate 102, after the portion of mixture 108 is aspirated, is determined at least in part by height V of aspirator 120 (e.g., a distance between a nozzle tip of aspirator 120 and a bottom of the well defined in the micro-titer plate 102).

FIG. 1F also illustrates that a portion of samples 114 is also aspirated by aspirator 120. Wells of micro-titer plate 102 have a high aspect ratio (e.g., a ratio between the height of the well and the diameter of the well). Thus, once samples 114 are agitated, it takes a long time for samples 114 to settle down. If a portion of mixture 108 is aspirated before samples 114 have fully settled down, a portion of samples 114 that is aspirated is increased.

In addition, FIG. 1F illustrates that samples 114 cluster toward corners of the well when the volume of mixture 108 is reduced. In addition, mixture 108 clings toward corners of the well. Both of these can reduce the efficiency of washing.

FIGS. 2A-2E illustrate washing operations with an array plate having a hydrophilic region and a hydrophobic area in accordance with some embodiments.

Figure 2A:
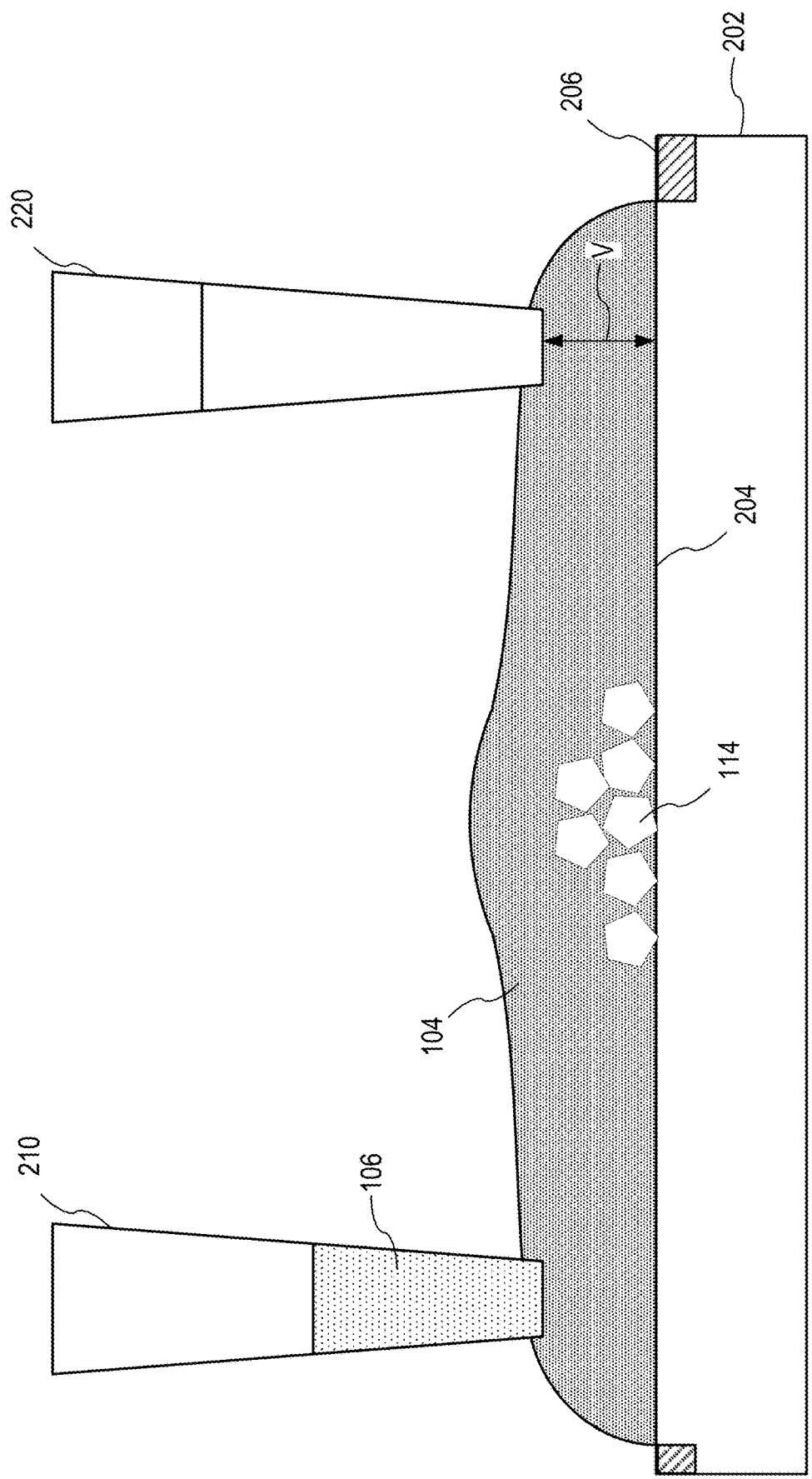
FIGS. 2A-2E illustrate washing operations with an array plate having a hydrophilic region and a hydrophobic area in accordance with some embodiments.

FIG. 2A is a partial cross-section of an array plate, where hydrophilic region 204 is surrounded by hydrophobic area 206. In FIG. 2A, solution 104 containing samples 114 is located over hydrophilic region 204. Solution 104 is retained over hydrophilic region 204, as surrounding hydrophobic area 206 prevents spreading of solution 104 beyond hydrophilic region 204.

FIG. 2A also illustrates dispenser 210 and aspirator 220. Dispenser 210 includes liquid 106 for washing samples 114 in solution 104 (by dilution of solution 104).

The array plate illustrated in FIG. 2A is configured to hold solution 104 without tall side walls, like conventional micro-titer plates. Thus, in the configuration shown in FIG. 2A, there are no corners toward which solution 104 and samples 114 cluster.

In addition, solution 104 in FIG. 2A has a low aspect ratio (e.g., a ratio between the height of solution 104 and the width or diameter of solution 104 on the array plate is less than the height of solution 104 and the diameter of solution 104 in a conventional micro-titer plate, sometimes by a factor of 2, 4, 6, 8, 10, or 20). Thus, when samples 114 are agitated, samples 114 in solution 104 on the array plate can settle faster than samples in solution 104 in a conventional micro-titer plate (shown in FIG. 1F).

In some embodiments, magnetic particles configured to couple with cells (e.g., coated with materials that can reversibly or irreversibly bind to the cells) are included in solution 104 (e.g., by introducing the magnetic particles into solution 104). Once the magnetic particles bind to the cells in solution 104, a magnetic field is applied to the magnetic particles in solution 104 to accelerate settling of the magnetic particles (and associated cells).

The inventors of this application have also discovered that the distance between hydrophilic region 204 and aspirator 220 (e.g., a distance between hydrophilic surface 204 and a nozzle tip of aspirator 220) is important in improving retention of samples 114. In some embodiments, aspirator 220 needs to be positioned at least 100 μm from hydrophilic region 204. In some embodiments, aspirator 220 needs to be positioned at least 200 μm from hydrophilic region 204. In some embodiments, aspirator 220 needs to be positioned at least 300 μm from hydrophilic region 204.

Figure 2B:
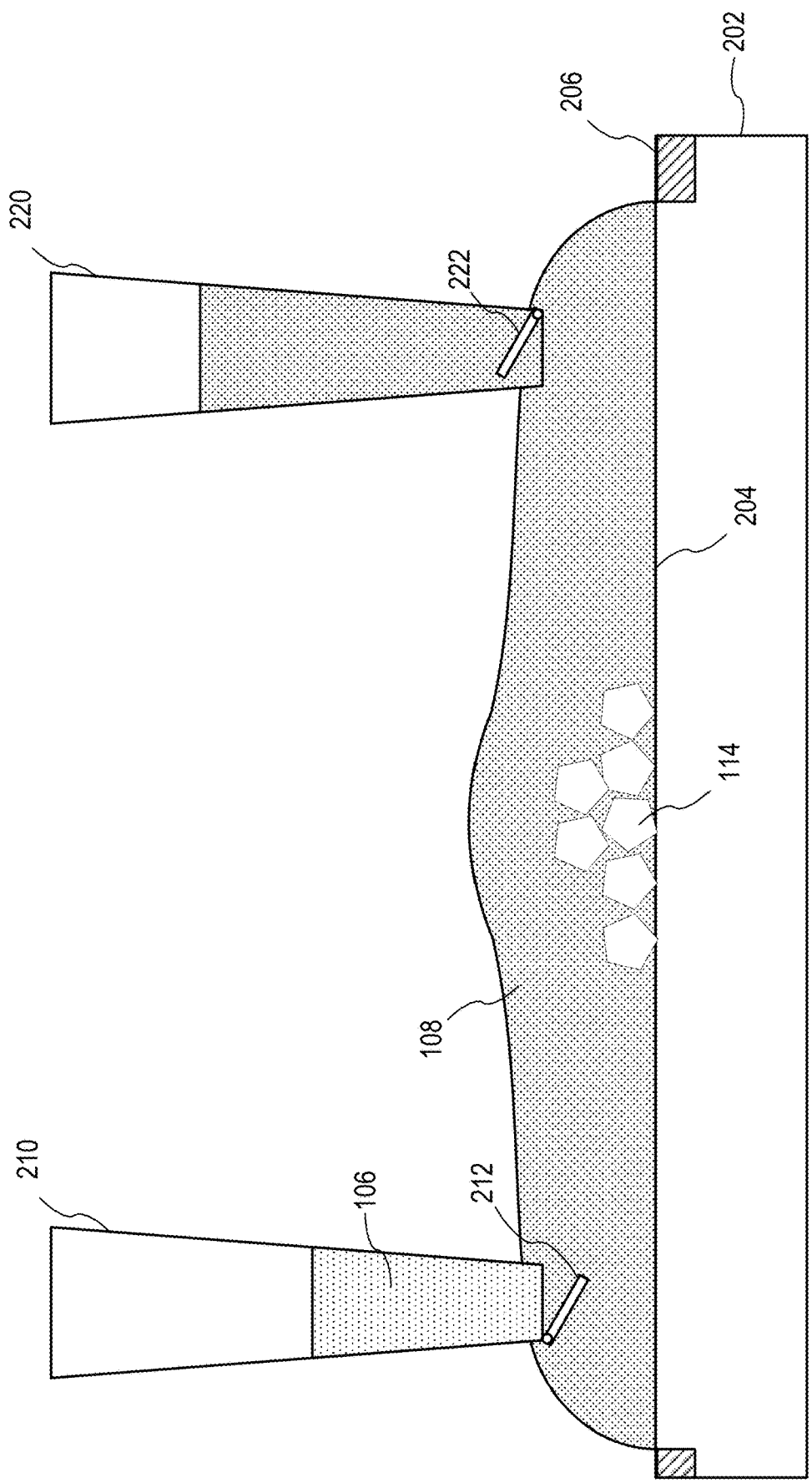

FIG. 2B illustrate dispenser 210 and aspirator 220 with improved volume control. A variation in the dispensed volume and/or the aspirated volume contributes to a variation in the dilution factor, which leads to an increased error in assays. Thus, reducing the variation in the volume of the dispensed liquid and/or the volume of the aspirated liquid improves the assay accuracy (e.g., an accuracy of an assay performed using the washing operation).

In FIG. 2B, dispenser 210 includes valve 212 (e.g., a one-way valve, which is also called a check valve, or a check valve) to reduce the variation in the volume of the dispensed liquid, and aspirator 220 includes valve 222 (e.g., a one-way valve or a check valve) to reduce the variation in the volume of the aspirated liquid. For example, a respective valve allows a liquid to flow in one direction but prevents the liquid to flow in the opposite direction (e.g., valve 212 allows the liquid in dispenser 210 to exit from dispenser 210 through valve 212 but prevents a liquid to enter into dispenser 210 through valve 212, and valve 222 allows mixture 108 to enter into aspirator 220 through valve 222 but prevents mixture 108 in aspirator 220 from exiting from aspirator 220 through valve 222).

Figure 2C:
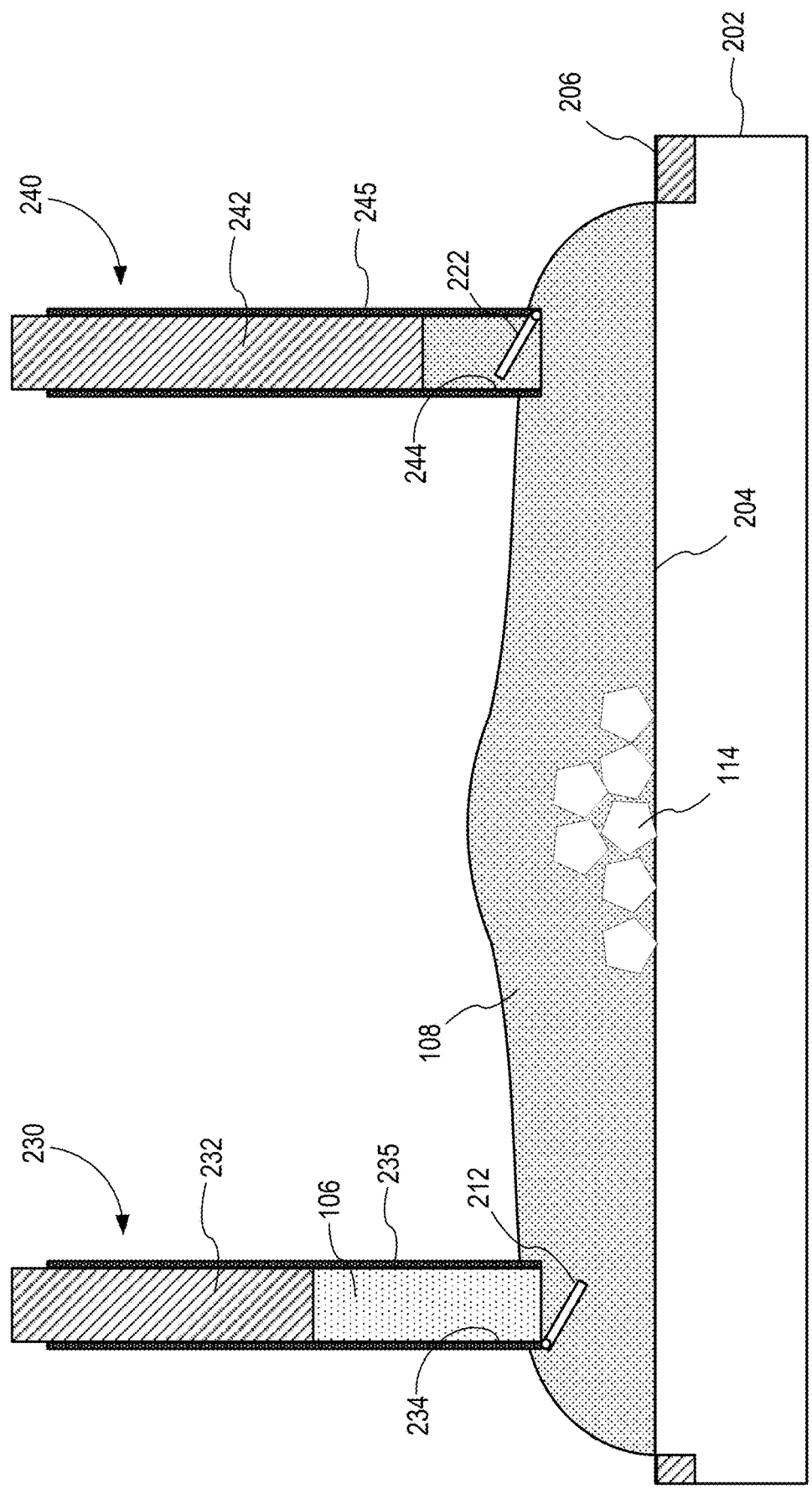

FIG. 2C is similar to FIG. 2B, except that dispenser 230 is used in place of dispenser 210 and aspirator 240 is used in place of aspirator 220. Dispenser 230 includes piston 232 (e.g., a plunger) configured to slide within channel 234 for dispensing wash liquid 106 in channel 234 through valve 212. Aspirator 240 includes piston 242 (e.g., a plunger) configured to slide within channel 244 for aspirating a liquid (mixture 108) into channel 244 through valve 222. In some embodiments, channel 234 is defined by tube 235. In some embodiments, channel 244 is defined by tube 245.

In some implementations, the volume of the aspirated liquid is controlled by a movement of piston 242 (e.g., a diameter of channel 244 and a travel distance of piston 242). In some embodiments, the diameter of piston 242 is less than the diameter of mixture 108, which facilitates an accurate control of the volume of the aspirated solution. Similarly, the volume of the aspirated liquid is accurately controlled by a movement of piston 232. In some implementations, the volume of the aspirated liquid (and/or the remaining liquid) is determined based on a height of an aspirator (e.g., a portion of the liquid located above the tip of aspirator 240 is aspirated and a portion of the liquid located below the tip of aspirator 240 remains, as shown in FIG. 1F).

Figure 2D:
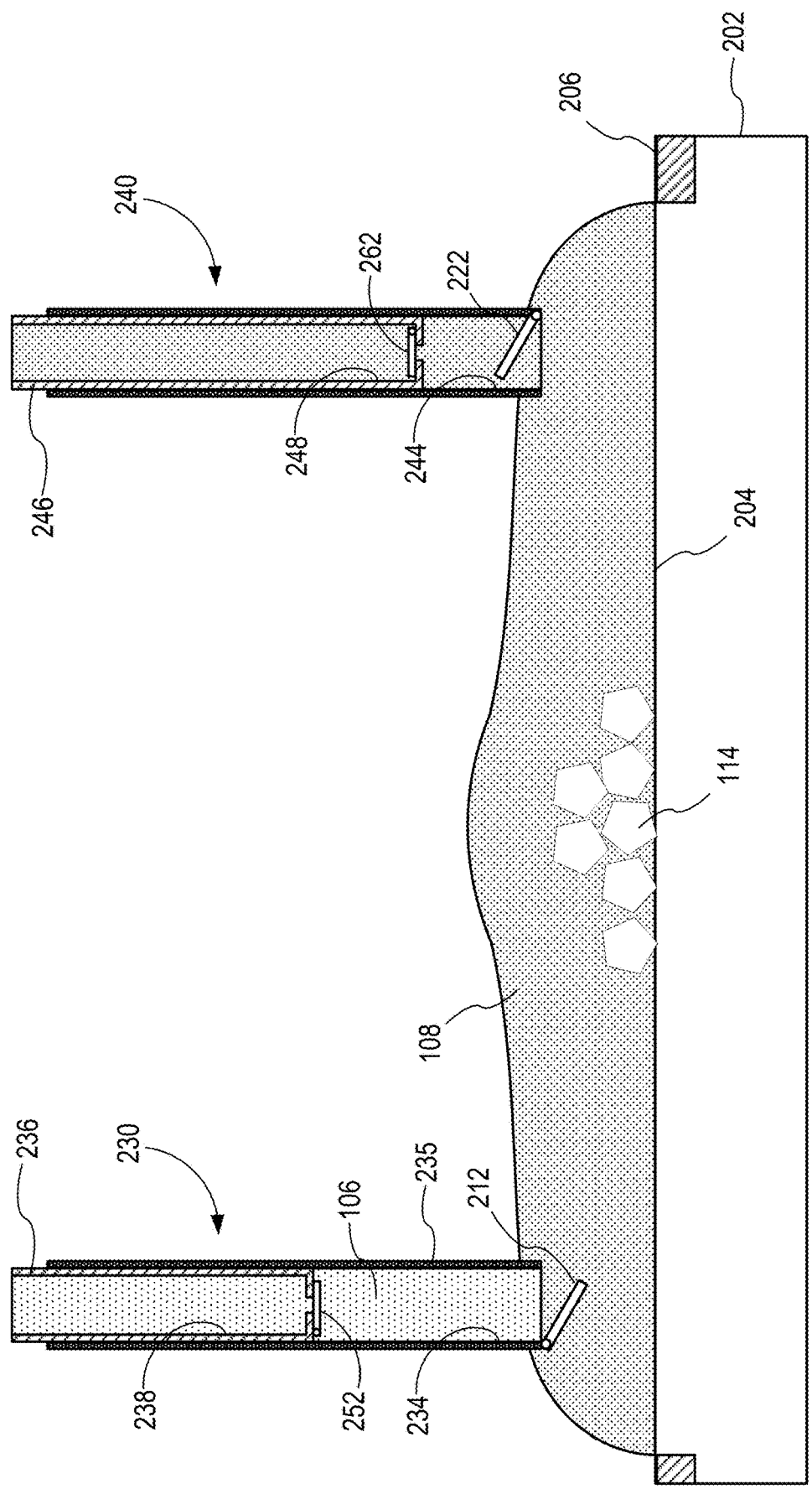

FIG. 2D is similar to FIG. 2C, except that piston 236 defines channel 238 within piston 236 and piston 236 is coupled with valve 252 (e.g., a one-way valve, a check valve, etc.), and piston 246 defines channel 248 within piston 246 and piston 246 is coupled with valve 262 (e.g., a one-way valve, a check valve, etc.). Channel 238 and valve 252 are configured to deliver a precise volume of wash liquid 106 into channel 234. Channel 248 and valve 262 are configured to remove mixture 108 in channel 244. The operations of these components are described further below with respect to FIGS. 3A-3G.

Figure 2E:
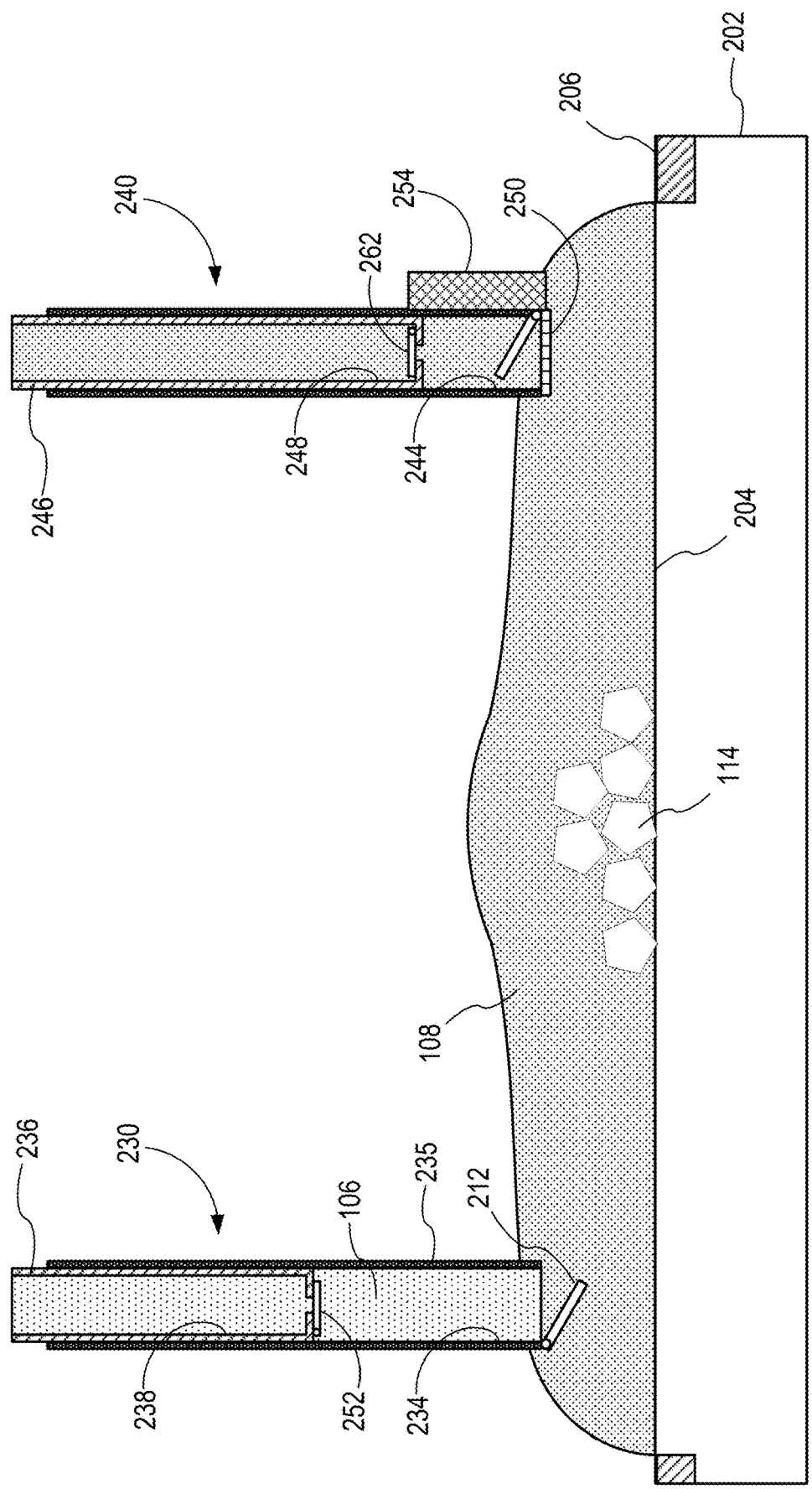

FIG. 2E is similar to FIG. 2D, except that filter 250 is coupled with a tip of aspirator 240. In some implementations, filter 250 reduces or prevents aspiration of cells. In some embodiments, filter 250 has a plurality of pores. In some embodiments, the plurality of pores has a pore size between 0.1 and 20 μm. In some embodiments, the plurality of pores has a pore size between 1 and 10 μm. In some embodiments, the plurality of pores has a pore size between 1 and 5 μm. In some embodiments, the plurality of pores has a pore size between 2 and 8 μm.

FIG. 2E also illustrates that aspirator 240 is coupled with vibrator 254. In FIG. 2E, vibrator 254 is positioned adjacent to filter 250. Vibrator 254 is configured to provide vibration to filter 250, which reduces clogging of filter 250 by preventing accumulation of cells on filter 250. In some embodiments, vibrator 254 is a piezo-electric vibrator.

Figure 3A:
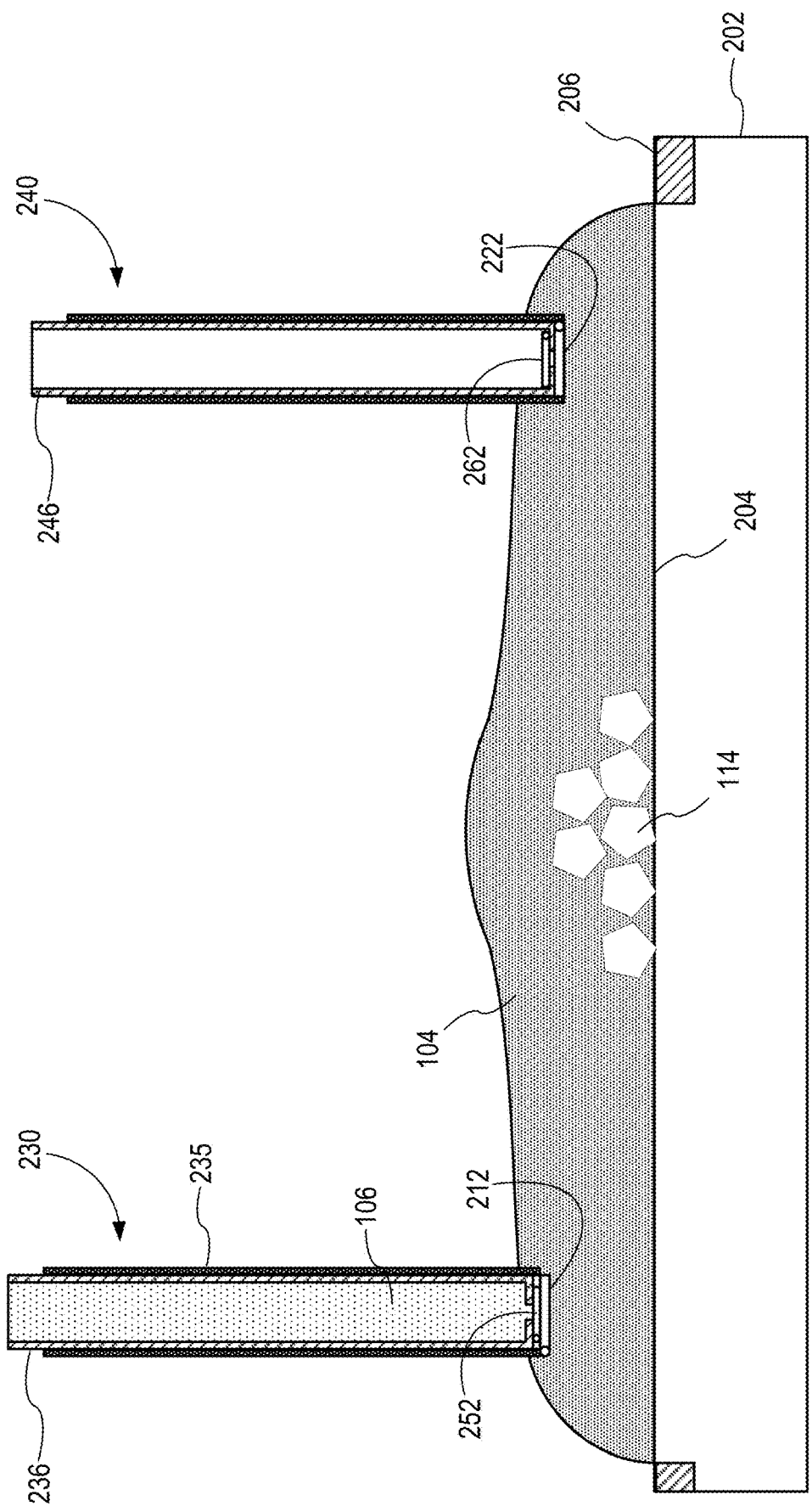
FIGS. 3A-3G illustrate a washing operation in accordance with some embodiments.

FIG. 3A illustrates that dispenser 230 includes piston 236 in a first position. The channel defined within piston 236 includes wash liquid 106.

Figure 3B:
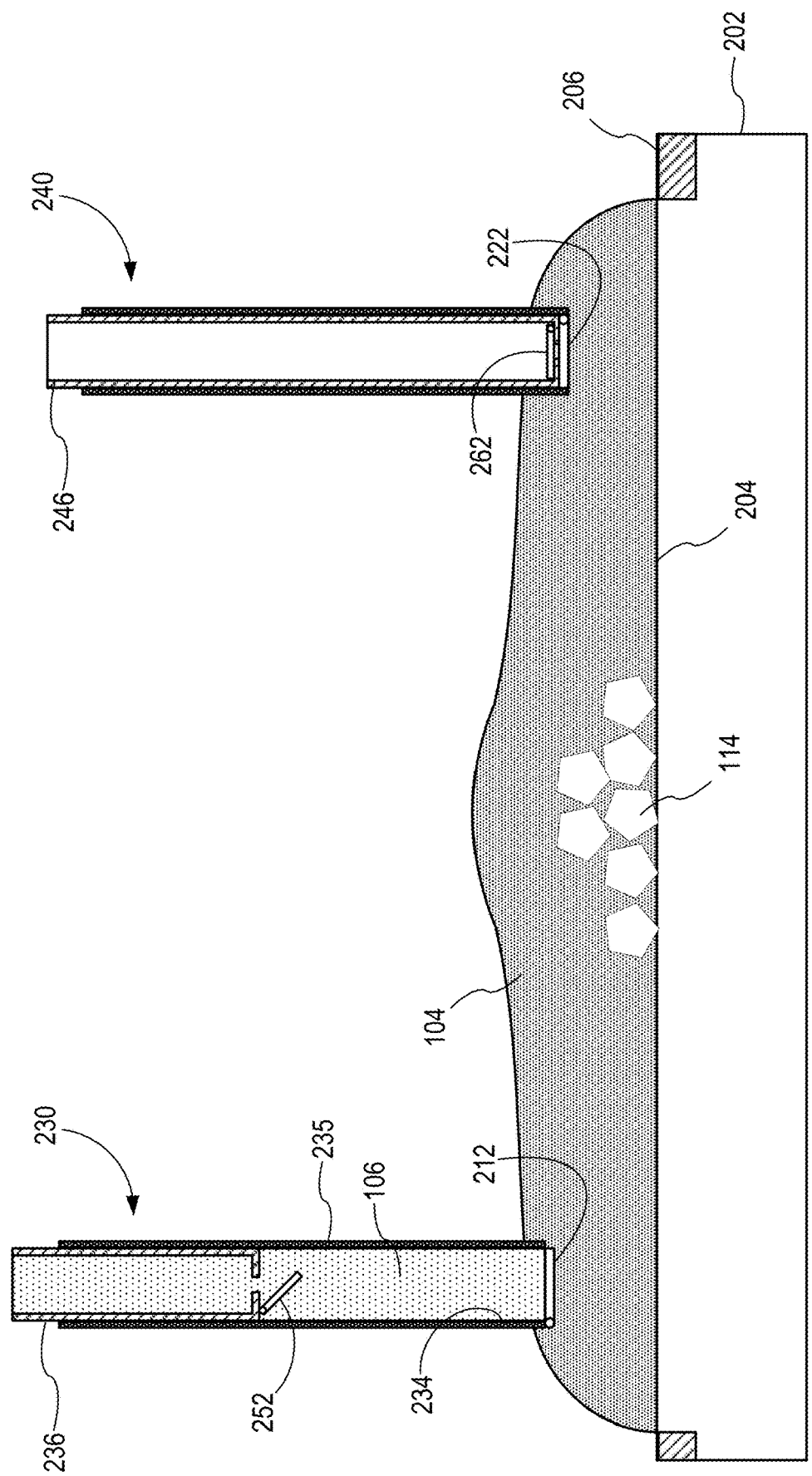

FIG. 3B illustrates that piston 236 moves up to a second position, which allows liquid 106 in the channel defined within piston 236 to flow into channel 234. During the upward movement of piston 236, there is a negative pressure within channel 234, which keeps valve 212 closed.

Figure 3C:
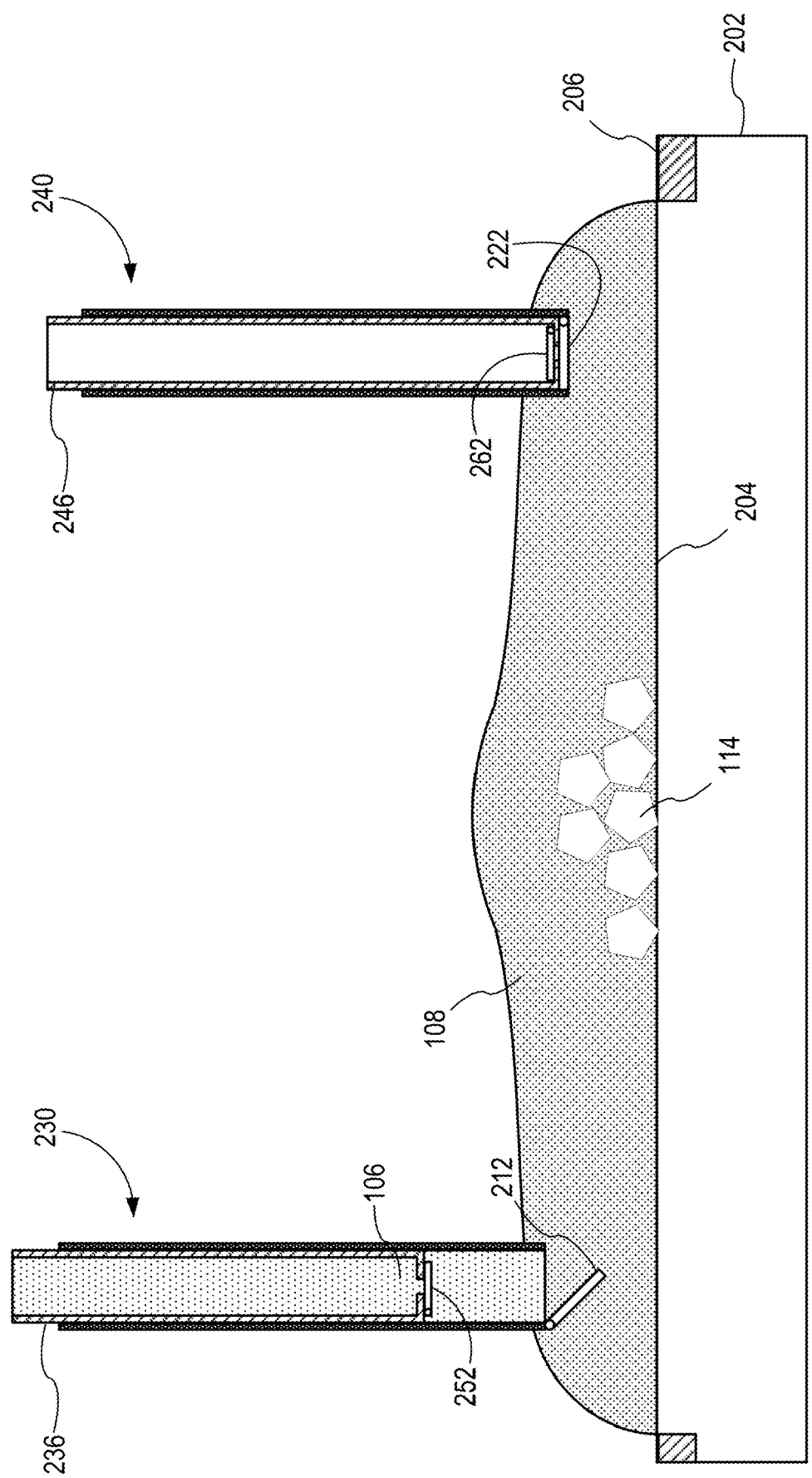

Once channel 234 is filled with a predefined volume of wash liquid 106, piston 236 moves down to push wash liquid 106 out of channel 234. FIG. 3C illustrates that piston 236 moves down, which causes valve 252 to close. The increased pressure within channel 234 opens valve 212 so that wash liquid 106 in channel 234 is dispensed (e.g., released) into sample solution 104, thereby forming mixture 108.

Figure 3D:
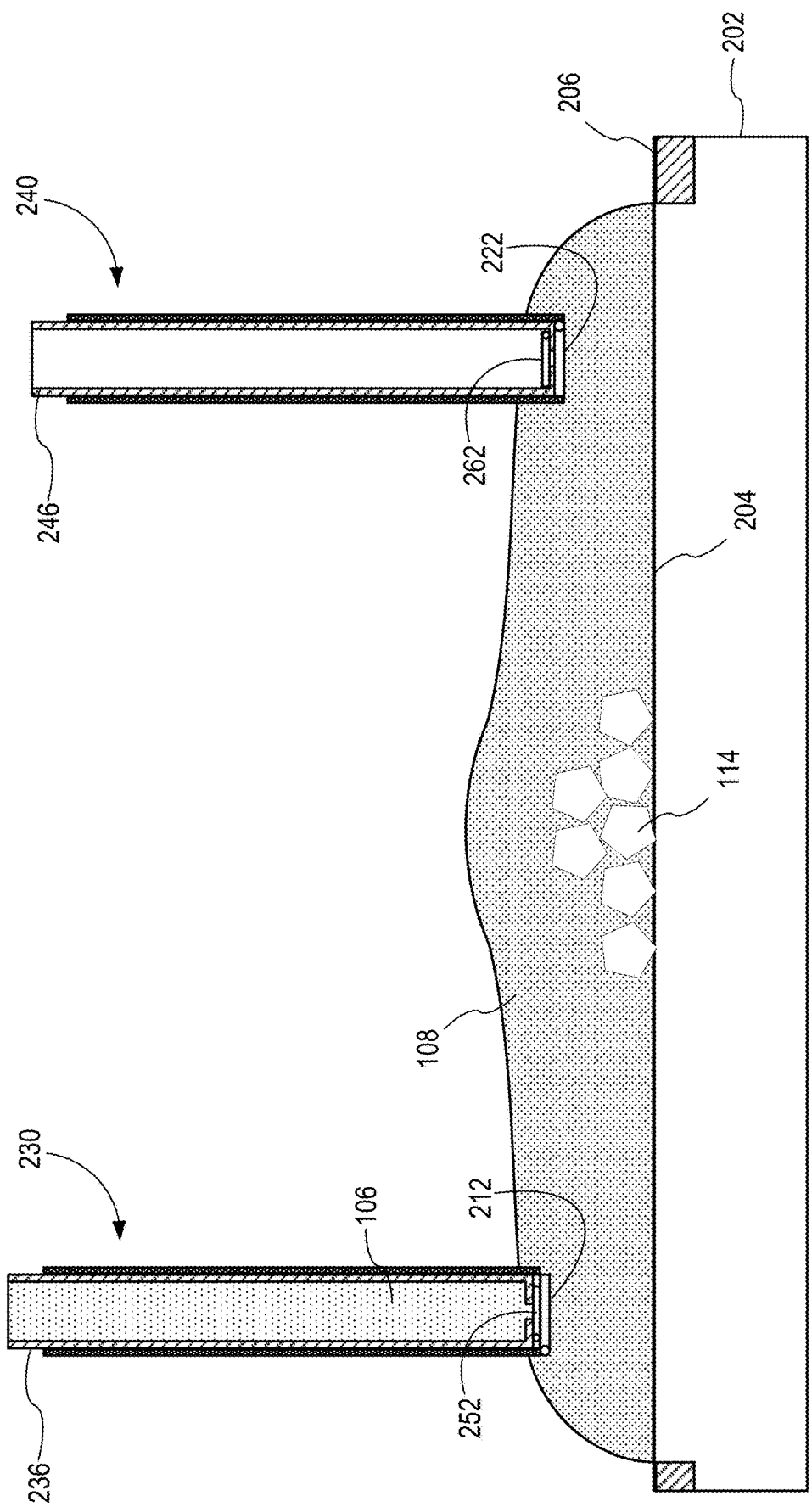

FIG. 3D illustrates that piston 236 has returned to the first position. In FIG. 3D, piston 246 of aspirator 240 is in a third position.

Figure 3E:
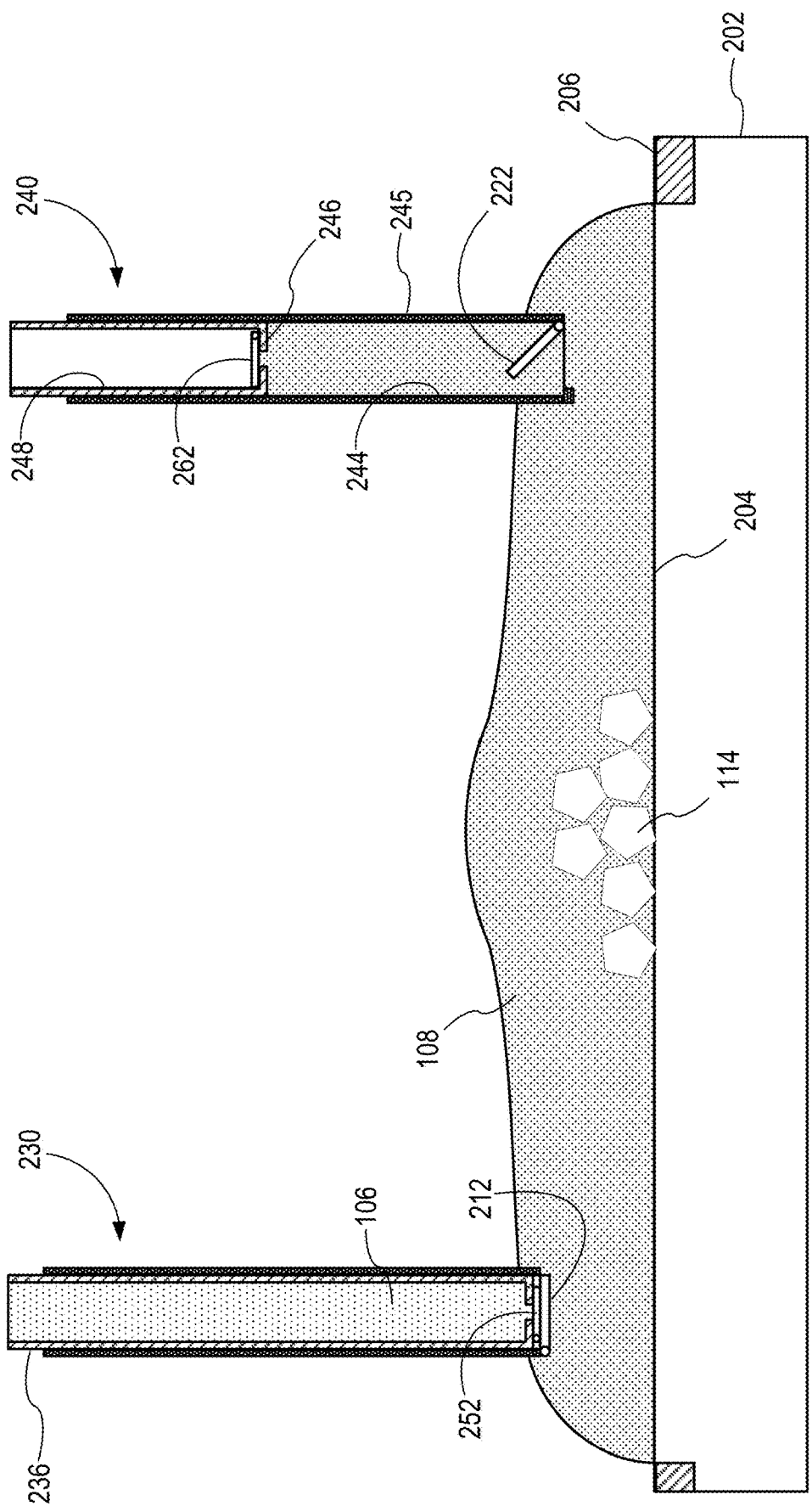

FIG. 3E illustrates an upward movement of piston 246 to a fourth position. The negative pressure within channel 244 causes valve 222 to open, which allows a portion of mixture 108 to flow into channel 244. The negative pressure within channel 244 causes valve 262 to close so that mixture 108 does not flow into the channel 248.

Figure 3F:
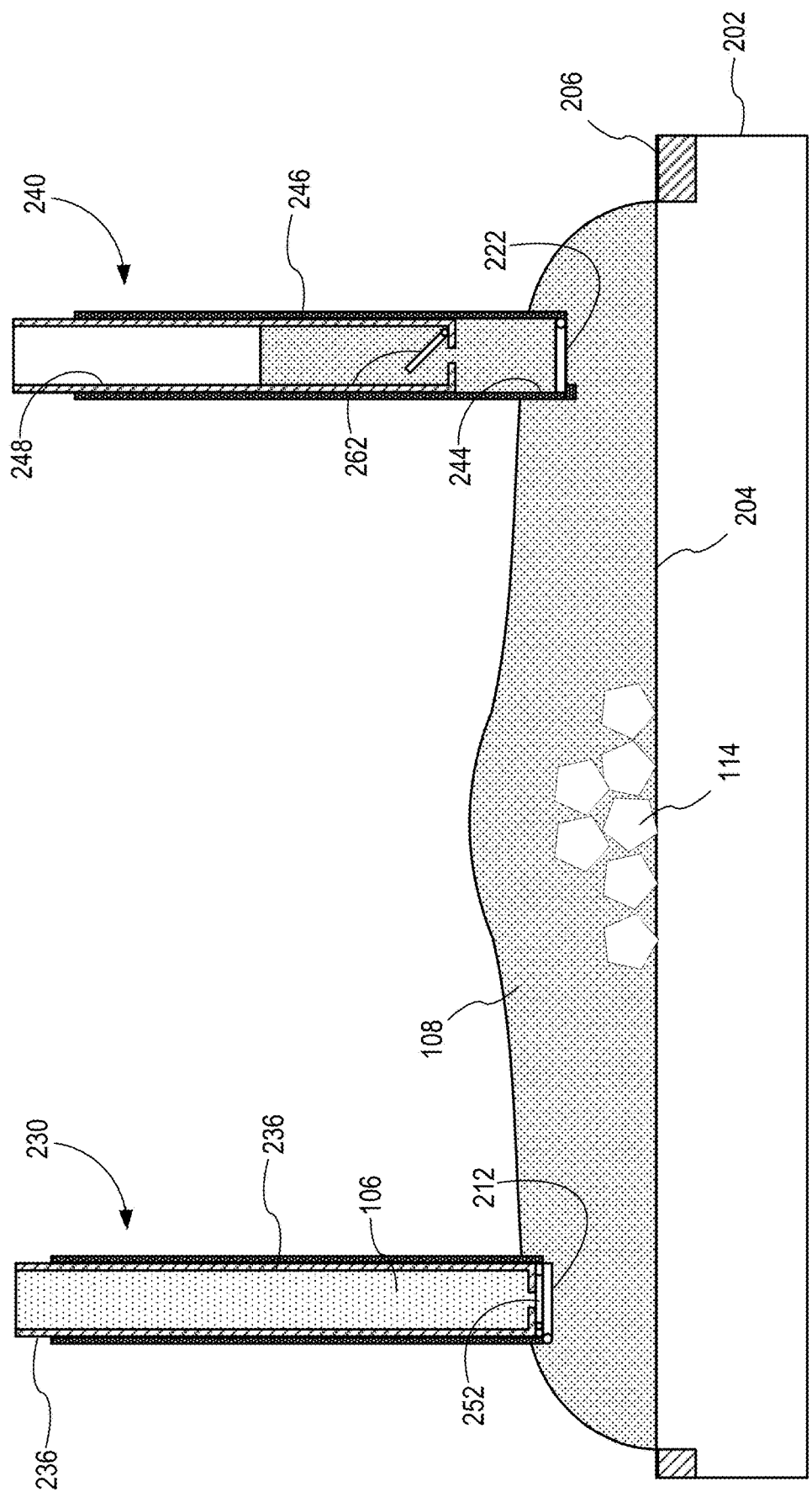

Once channel 244 is filled with a predefined volume of mixture 108, piston 246 moves down to move mixture 108 in channel 244 to channel 248. FIG. 3F illustrates piston 246 moves down, which causes valve 222 to close. The increased pressure within channel 244 opens valve 262 so that mixture 108 in channel 244 flows into channel 248.

Figure 3G:
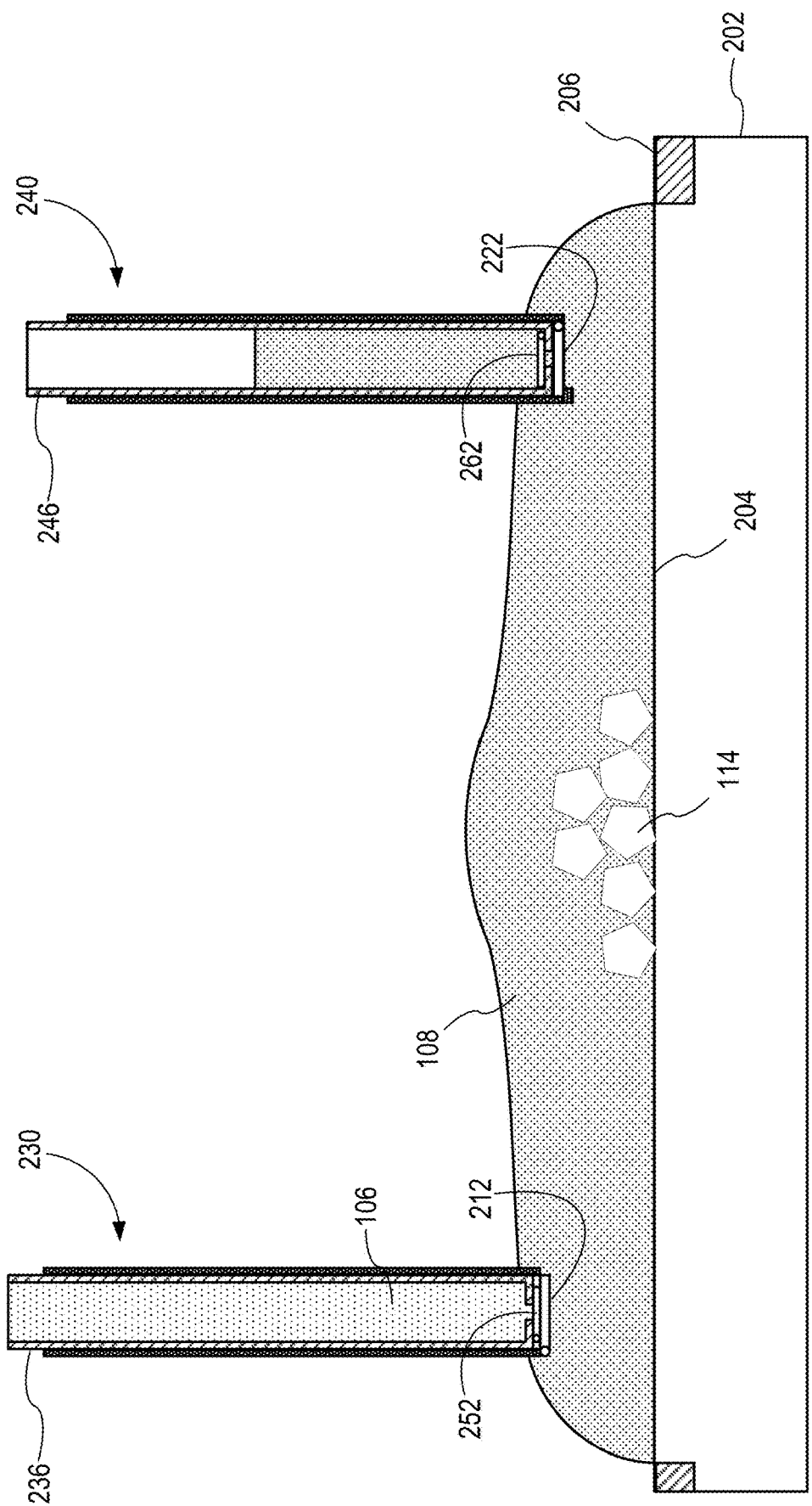

FIG. 3G illustrates that piston 246 has returned to the third position.

In some embodiments, dispenser 230 is coupled with a wash liquid source (e.g., a reservoir containing a wash liquid, which is optionally combined with a pump configured to provide the wash liquid). For example, wash liquid 106 is provided to channel 238 by the wash liquid source. In some embodiments, aspirator 240 is coupled with a suction pump. For example, mixture 108 in channel 248 is removed by the suction pump. In some embodiments, aspirator 240 is coupled with a reservoir. For example, mixture 108 in channel 248 is drained to the reservoir while piston 246 moves up.

In some embodiments, subsequent to dispensing wash liquid 106 and prior to aspirating a portion of mixture 108, mixture 108 is shaken and/or agitated (e.g., the array plate on which mixture 108 is located is shaken and/or agitated by placing the array plate on a shaker and activating the shaker).

In some embodiments, one or more valves illustrated in FIGS. 3A-3G (e.g., valves 212, 222, 252, and 262) are spring-loaded. A spring-loaded valve is configured to close itself and/or remain closed when a pressure difference applied on the valve is less than a predefined threshold.

Figure 3H:
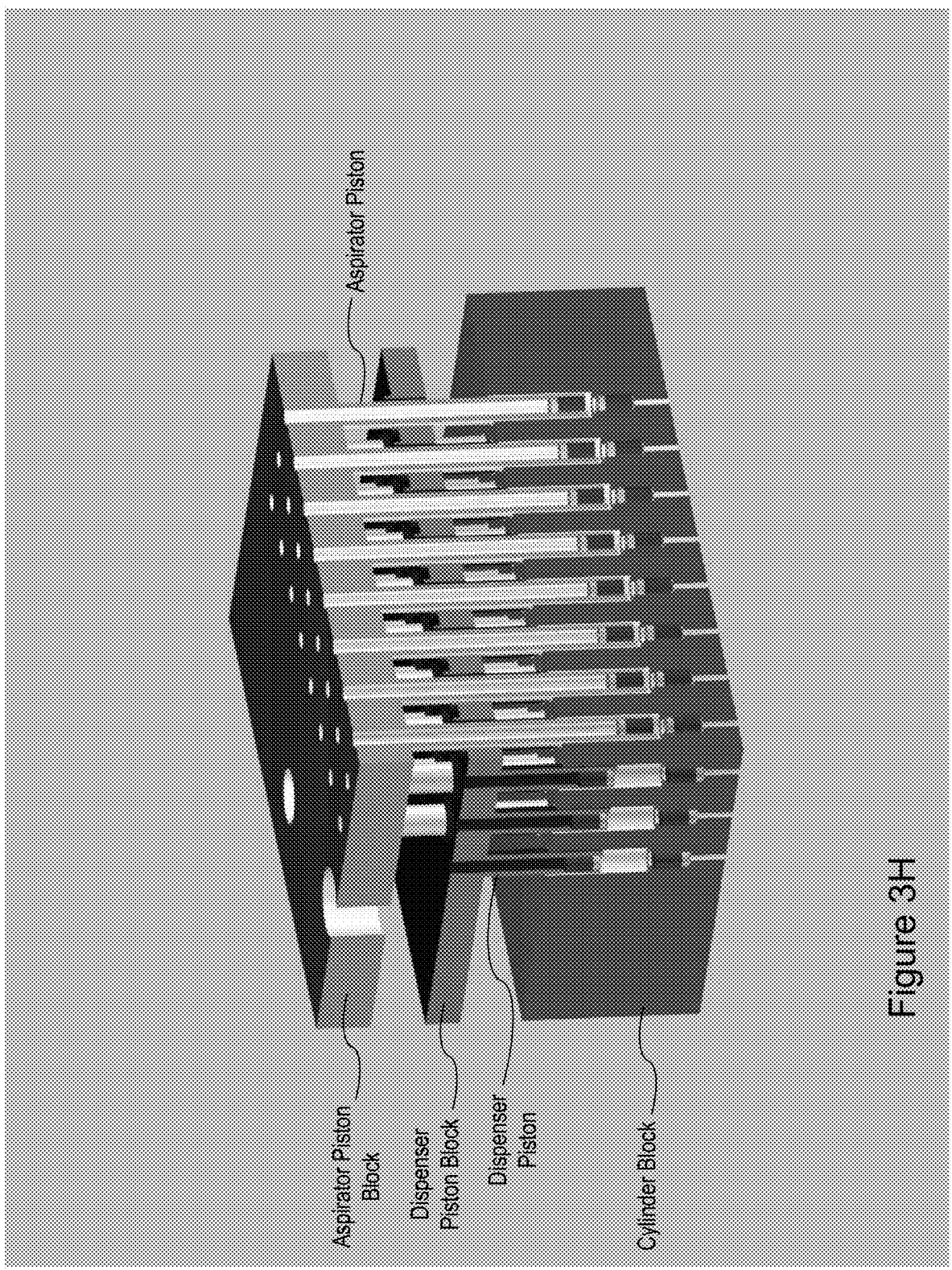
FIG. 3H illustrates components of a washing apparatus in accordance with some embodiments.

Although FIGS. 3A-3G illustrate that a single dispenser and a single aspirator for a single sample spot, in some embodiments, multiple dispensers and/or multiple aspirators are used for a single sample spot (e.g., using multiple dispensers and multiple aspirators for a particular sample spot can reduce the washing time, especially for a large sample spot). In some embodiments, multiple dispensers are configured for concurrent operations and/or multiple aspirators are configured for concurrent operations. For example, multiple dispensers are built into a single block, and multiple aspirators are built into a single block, as shown in FIG. 3H.

In some embodiments, a single dispenser is used for dispensing a wash liquid into multiple spots. For example, a single dispenser is coupled with a split channel (e.g., 2-channel, 4-channel, 8-channel, 12-channel, 16-channel, 32-channel, 64-channel, 128-channel, 256-channel splitter). In some embodiments, a single aspirator is used for aspirating liquid (e.g., a mixture) from multiple spots. For example, a single aspirator is coupled with a split channel (e.g., 2-channel, 4-channel, 8-channel, 16-channel, 32-channel, 64-channel, 128-channel, 256-channel splitter).

In some embodiments, one or more of a dispenser and an aspirator are coupled with a positive displacement pump (e.g., a membrane pump, such as a solenoid micropump). The positive displacement pump reduces the variation in the volume of the dispensed liquid or the volume of the aspirated liquid. In some embodiments, a dispenser is coupled with a positive displacement pump without a valve. In some embodiments, an aspirator is coupled with a positive displacement pump without a valve.

Although FIGS. 2A-2E and 3A-3G illustrate configurations, in which both a dispenser and an aspirator are concurrently in contact with a liquid (e.g., solution 104 or mixture 108), a person having ordinary skill in the art would understand that only one of the dispenser and the aspirator may be in contact with the liquid (e.g., a dispenser comes in contact with solution 104 first for dispensing a wash liquid, while an aspirator remains separated from solution 104, and the dispenser is subsequently removed from mixture 108 of solution 104 and the wash liquid, and the aspirator comes in contact with mixture 108 for aspirating a portion of mixture 108 while the dispenser remains separated from mixture 108). In some embodiments, a dispenser is used at a first time without an aspirator, and an aspirator is used at a second time distinct from the first time (e.g., the second time is subsequent to the first time) without a dispenser. For brevity, these details are omitted.

In FIGS. 1A-1F, 2A-2E, and 3A-3G, top portions of dispensers and aspirators are truncated to simplify the drawings.

Although FIGS. 2A-2E and 3A-3G illustrate washing operations, analogous operations can be used for introducing reagents to the array plate (or the cells on the array plate). For example, instead of a wash liquid, a reagent liquid (e.g., a liquid containing reagents for reaction with cells) is used in some implementations. Such operations can introduce the reagents without agitating the cells on the array plate, thereby improving the accuracy and reliability of reaction between the reagents and the cells. In addition, the loss of the cells is reduced by using such operations.

Although FIGS. 2A-2E and 3A-3G illustrate an aspirator located away from a dispenser (e.g., the aspirator and the dispenser are located toward two opposite ends of solution 104), in some implementations, the aspirator and the dispenser are located adjacent to each other (e.g., the aspirator and the dispenser are located toward a same end of solution 104, or toward the center of solution 104).

Figure 4A:
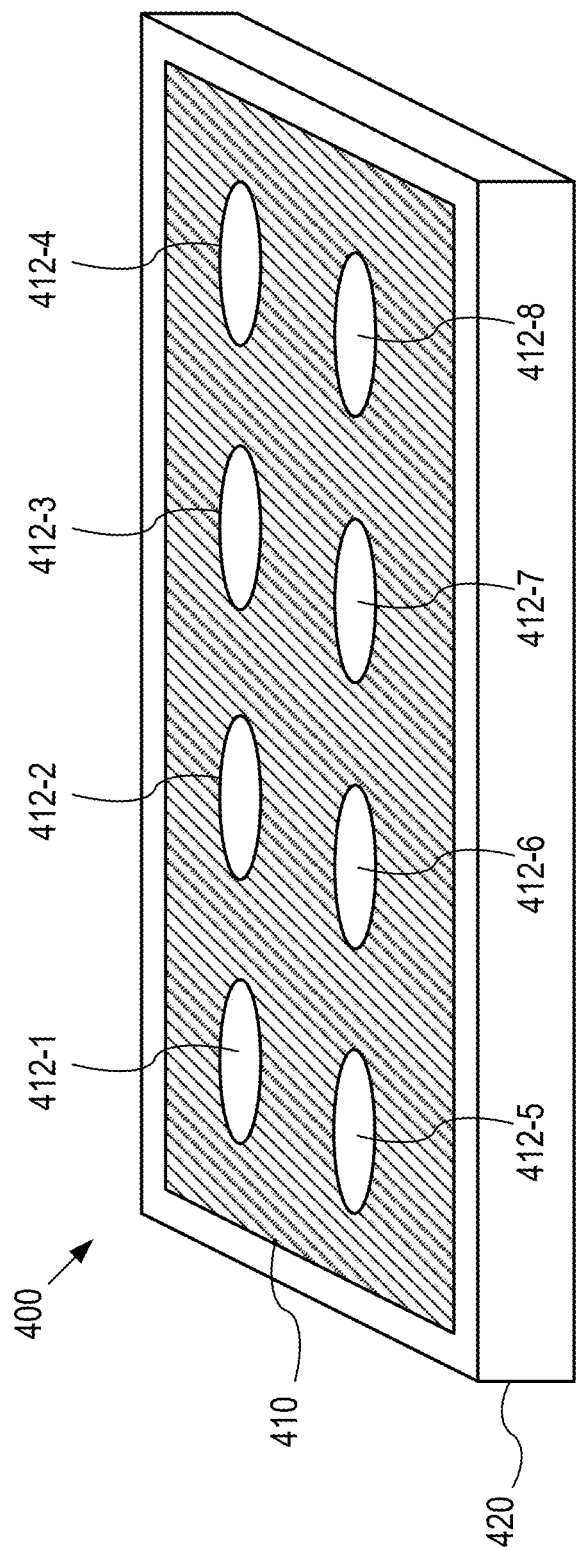
FIGS. 4A-4C are perspective views of array plates in accordance with some embodiments.
Figure 4B:
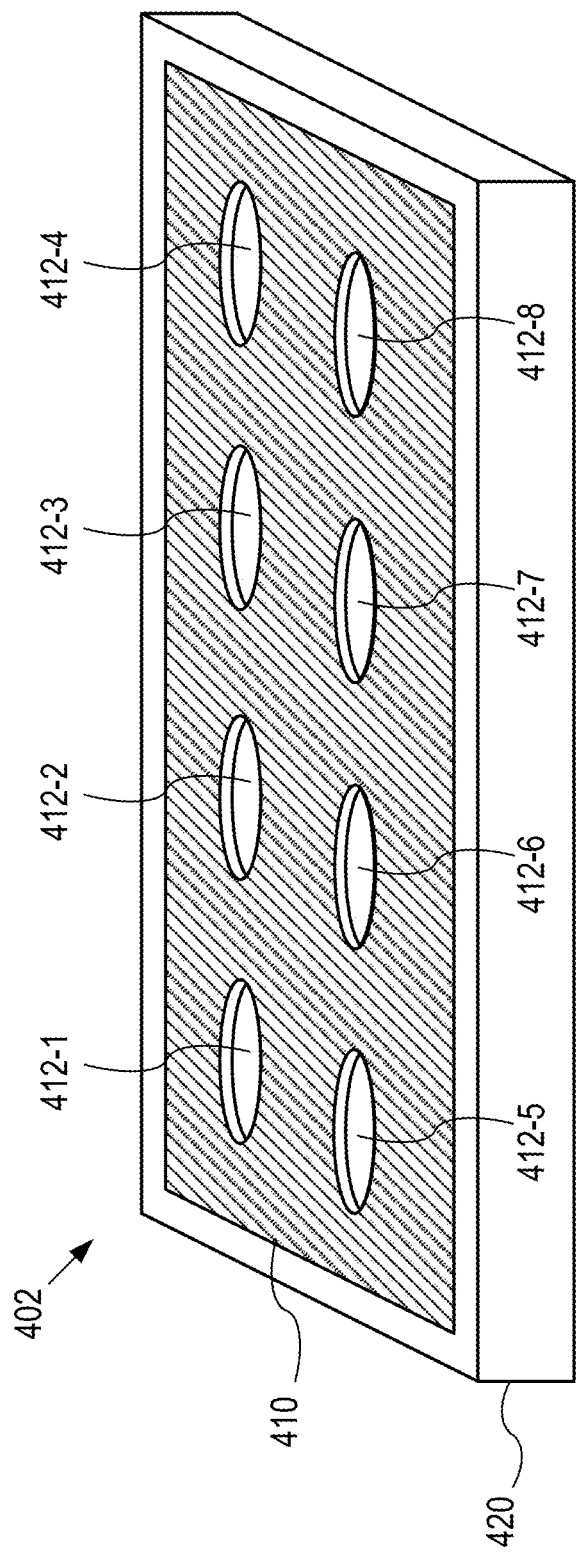
Figure 4C:
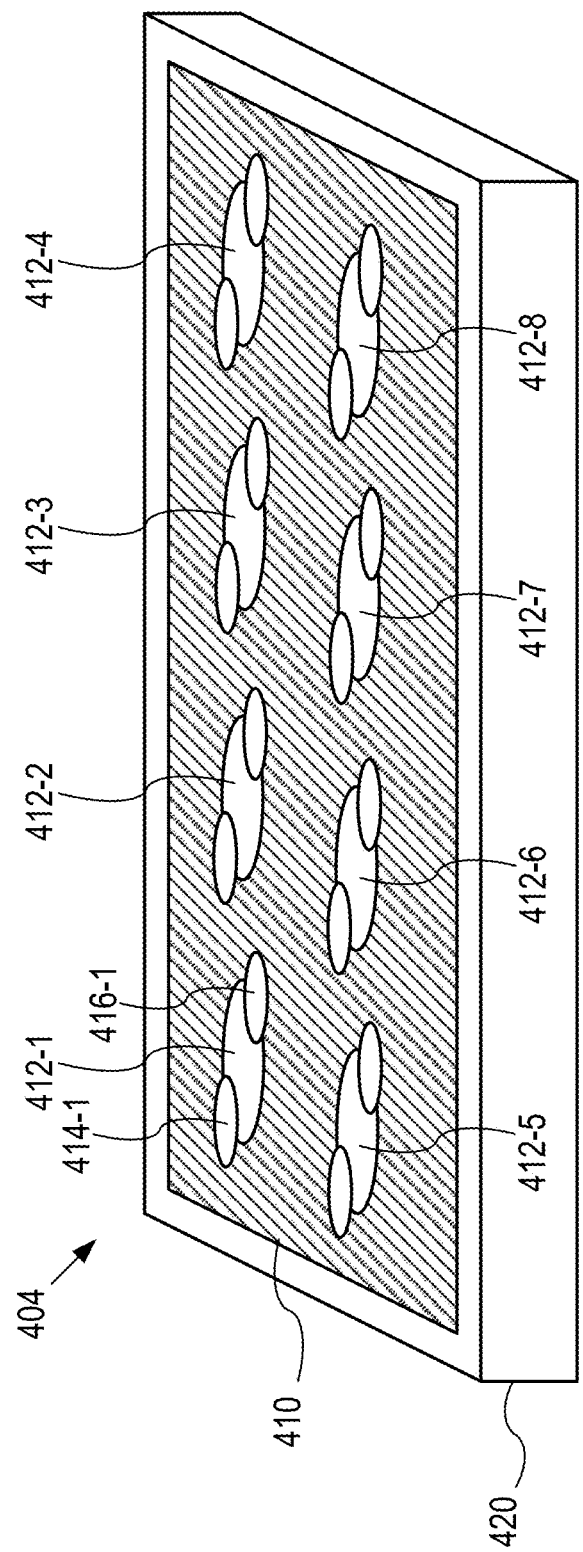

FIGS. 4A-4C are perspective views of array plates in accordance with some embodiments.

FIG. 4A illustrates array plate 400 with base 420. On top of base 420, hydrophilic regions 412 (e.g., 412-1, 412-2, 412-3, 412-4, 412-5, 412-6, 412-7, and 412-8) are surrounded by hydrophobic area 410.

FIG. 4B illustrates array plate 402, which is similar to array plate 400 except that hydrophilic regions 412 are offset from surrounding hydrophobic area 410.

In some embodiments, a respective hydrophilic region 412 (e.g., hydrophilic region 412 in FIG. 4A or FIG. 4B) has a circular shape or an ellipsoidal shape.

FIG. 4C illustrates array plate 404, which is similar to array plate 400 except that hydrophilic regions 412 (called herein "primary areas") are coupled with one or more secondary areas, such as secondary areas 414 (e.g., 414-1) and 416 (e.g., 416-1). Although each hydrophilic region 412 in FIG. 4C is coupled with two secondary areas, a respective hydrophilic region may have only one secondary area, or more than two secondary areas (e.g., three or four secondary areas). A secondary area is a hydrophilic region that is configured for placing a dispenser and/or an aspirator. However, in some embodiments, a hydrophilic region without any secondary area (e.g., array plates 400 and 402 shown in FIGS. 4A and 4B) is used, and a dispenser and an aspirator are positioned over the hydrophilic region (e.g., a primary area).

Figure 4D:
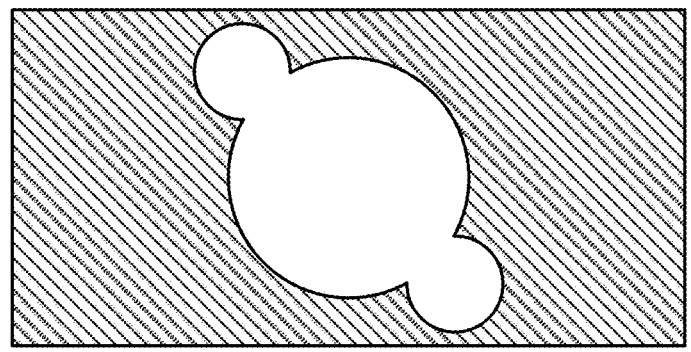
FIGS. 4D-4F are partial plan views of example array plates in accordance with some embodiments.
Figure 4E:
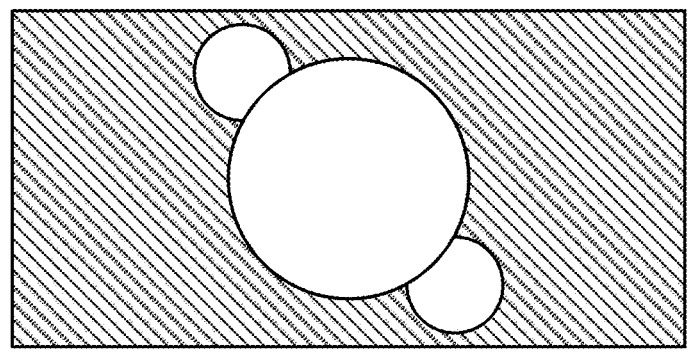
Figure 4F:
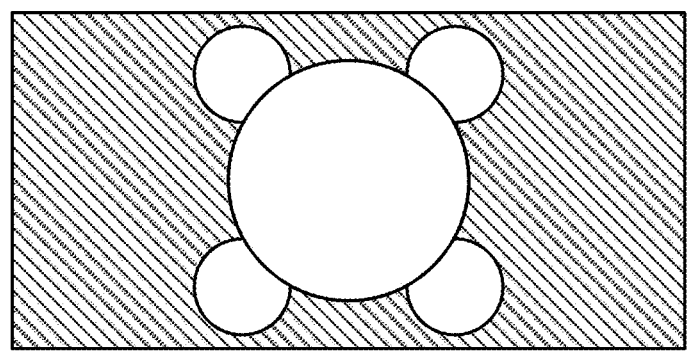

FIGS. 4D-4F are partial plan views of example array plates in accordance with some embodiments. In FIGS. 4D-4F, a respective hydrophilic region (or a primary area) has a circular shape, and a respective secondary area has a shape that corresponds to a portion of a circle (e.g., a crescent shape).

FIG. 4D illustrates that a hydrophilic region (also called herein a primary area) and secondary areas are located on a same plane.

FIG. 4E illustrates that a hydrophilic region (or a primary area) is located on a plane different from a plane on which secondary areas are located. Partial cross-sections of different embodiments that correspond to FIG. 4E are illustrated in FIGS. 5A-5D.

FIG. 4F illustrates a hydrophilic region (or a primary area) with four adjacent secondary areas in accordance with some embodiments.

Figure 4G:
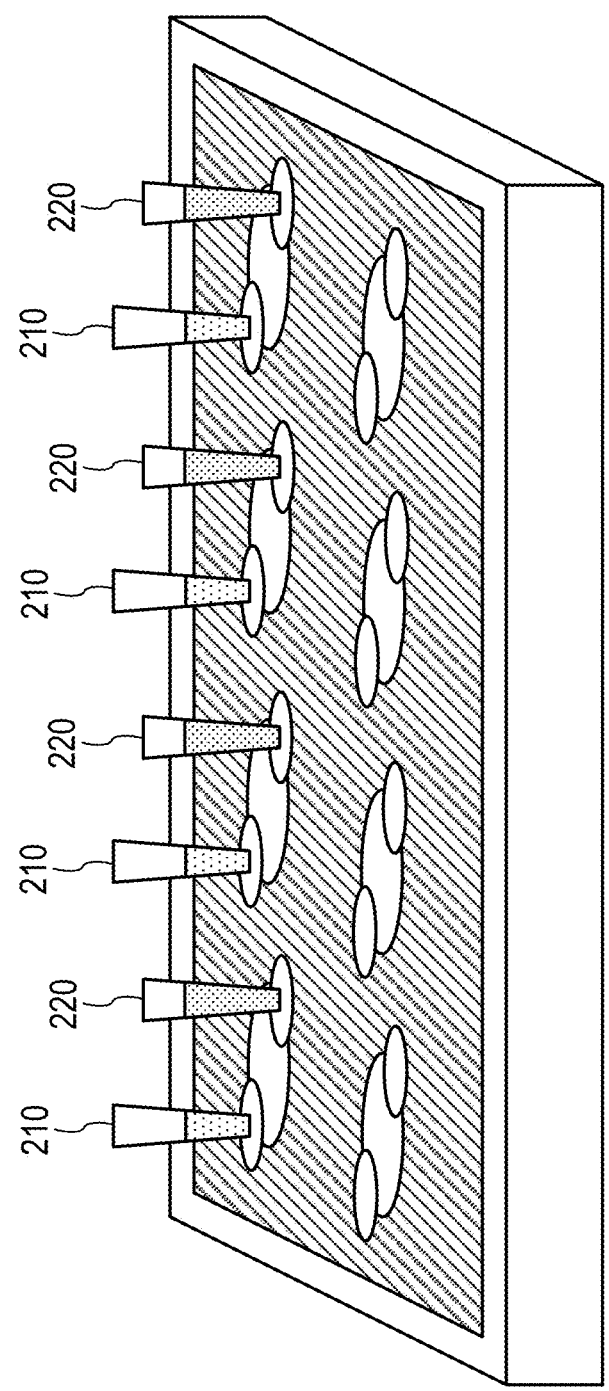
FIGS. 4G-4H illustrate arrangement of dispensers and aspirators in accordance with some embodiments.
Figure 4H:
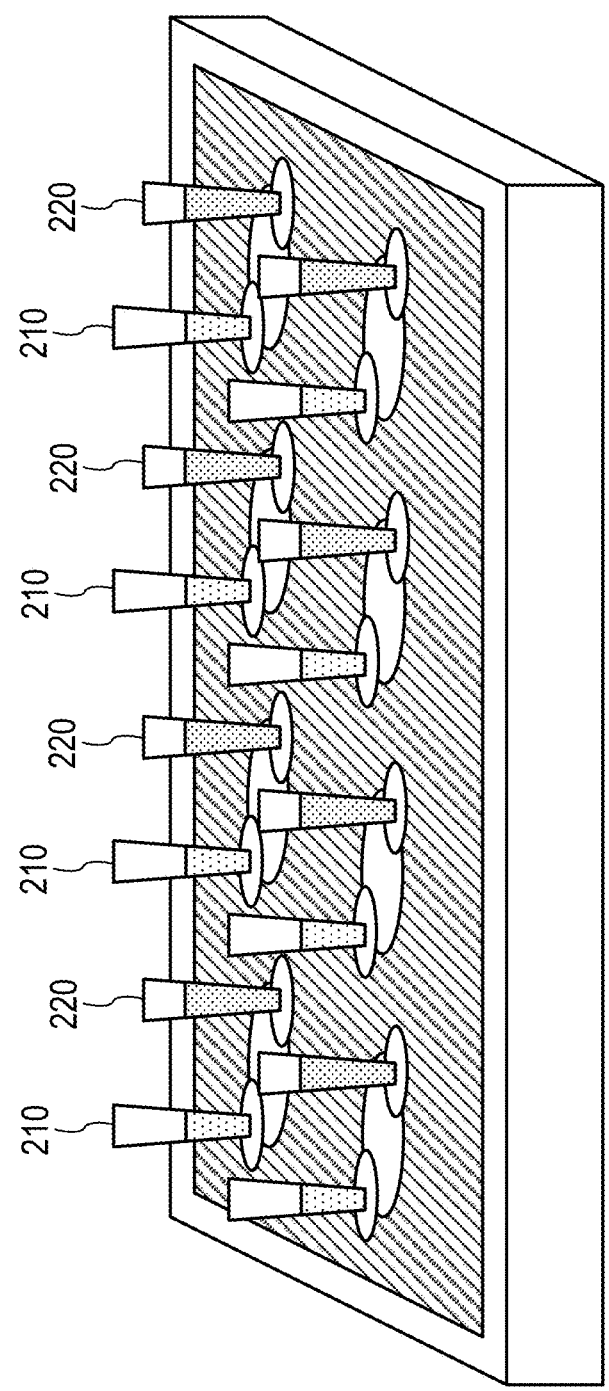

FIGS. 4G-4H illustrate arrangement of dispensers and aspirators in accordance with some embodiments.

FIG. 4G illustrates that a row of dispensers 210 and a row of aspirators 220 are used. As shown in FIG. 4G, a row of dispensers 210 is used to dispense a wash liquid to a row of spots (or associated hydrophilic secondary areas) and a row of aspirators 220 is used to aspirate mixtures from the same row of spots (or associated hydrophilic secondary areas). In some cases, after a row of spots is washed, the array plate and/or the dispensers and the aspirators are moved so that the next row of spots can be washed.

FIG. 4H illustrates that a two-dimensional array of dispensers 210 and a two-dimensional array of aspirators 220 are used.

Figure 5A:
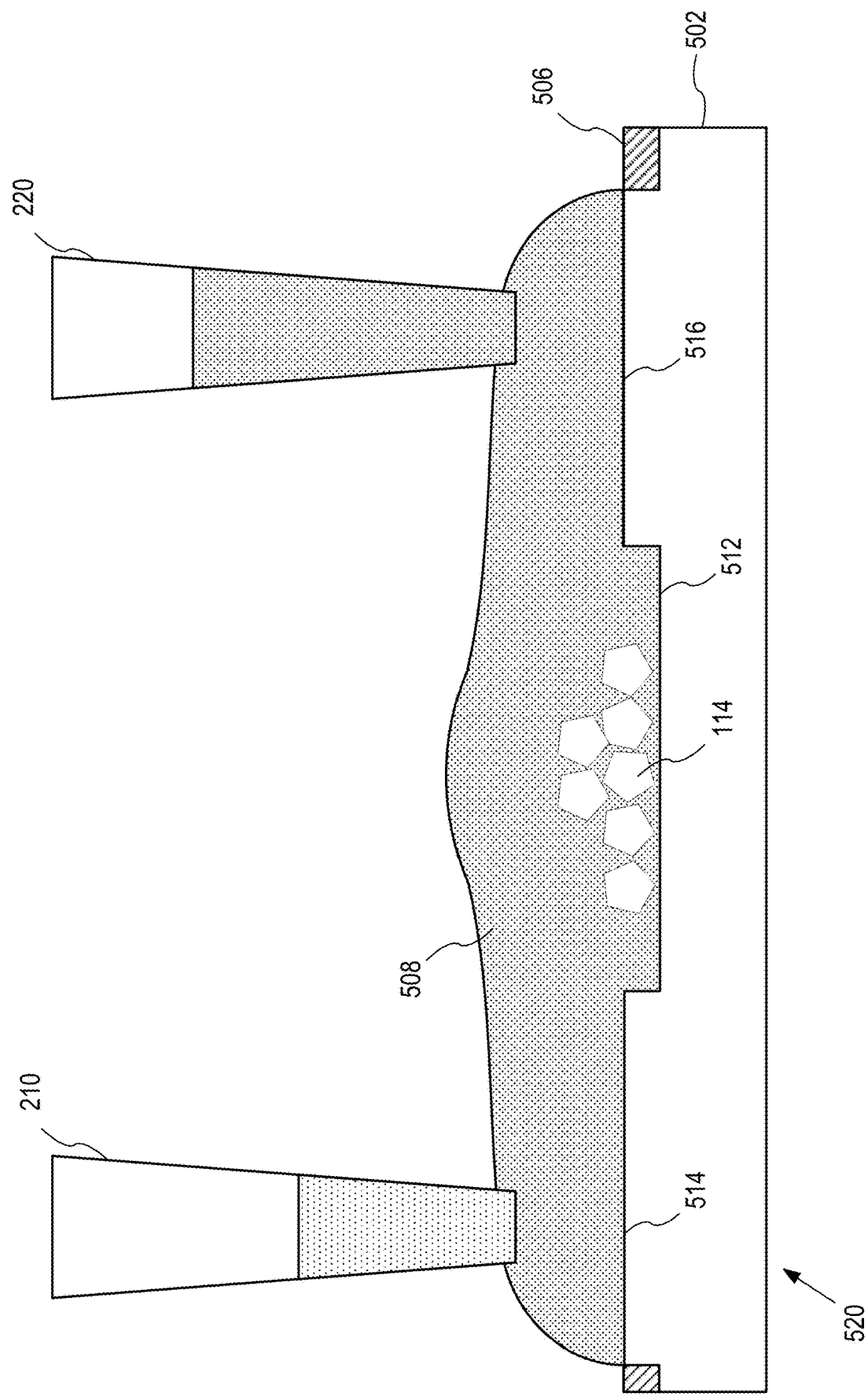
FIGS. 5A-5I are partial cross-sectional views of example array plates in accordance with some embodiments.

FIG. 5A illustrates a partial cross-section of array plate 520. Array plate 520 includes base 502 with secondary areas 514 and 516 located on a same plane as surrounding hydrophobic area 506. Primary area 512 is located offset from the plane on which secondary areas 514 and 516 are located (e.g., primary area 512 is indented so that primary area 512 is located deeper than secondary areas 514 and 516).

In some embodiments, the hydrophilic areas (e.g., the primary area and/or the secondary areas) include, or are made of, hydrophilic materials, such as polyvinyl alcohol, poly vinyl pyrrolidone, etc. In some embodiments, the hydrophobic area includes, or is made of, hydrophobic materials, such as a polytetrafluoroethylene (PTFE) matrix, poly(methylmethacrylate), etc.

In some embodiments, the hydrophilic areas (e.g., the primary area and/or the secondary areas) include, or are made of, glass (e.g., the primary area and/or the secondary areas are etched into glass). In some embodiments, the hydrophobic area includes a layer of hydrophobic material (e.g., a hydrophobic coating), such as a polytetrafluoroethylene (PTFE) layer (e.g., a PTFE tape). For example, the polytetrafluoroethylene (PTFE) matrix is patterned on a glass slide (e.g., a microscope slide) so that the PTFE matrix covers portions of the glass microscope slide and the remaining portions of the glass microscope slide are not covered by the PTFE matrix. The PTFE matrix has hydrophobic characteristics and the portions of the glass microscope slide that are not covered by the PTFE matrix have hydrophilic characteristics. Aqueous solutions that include samples (e.g., cells) are typically placed on hydrophilic areas of the slide.

Figure 5B:
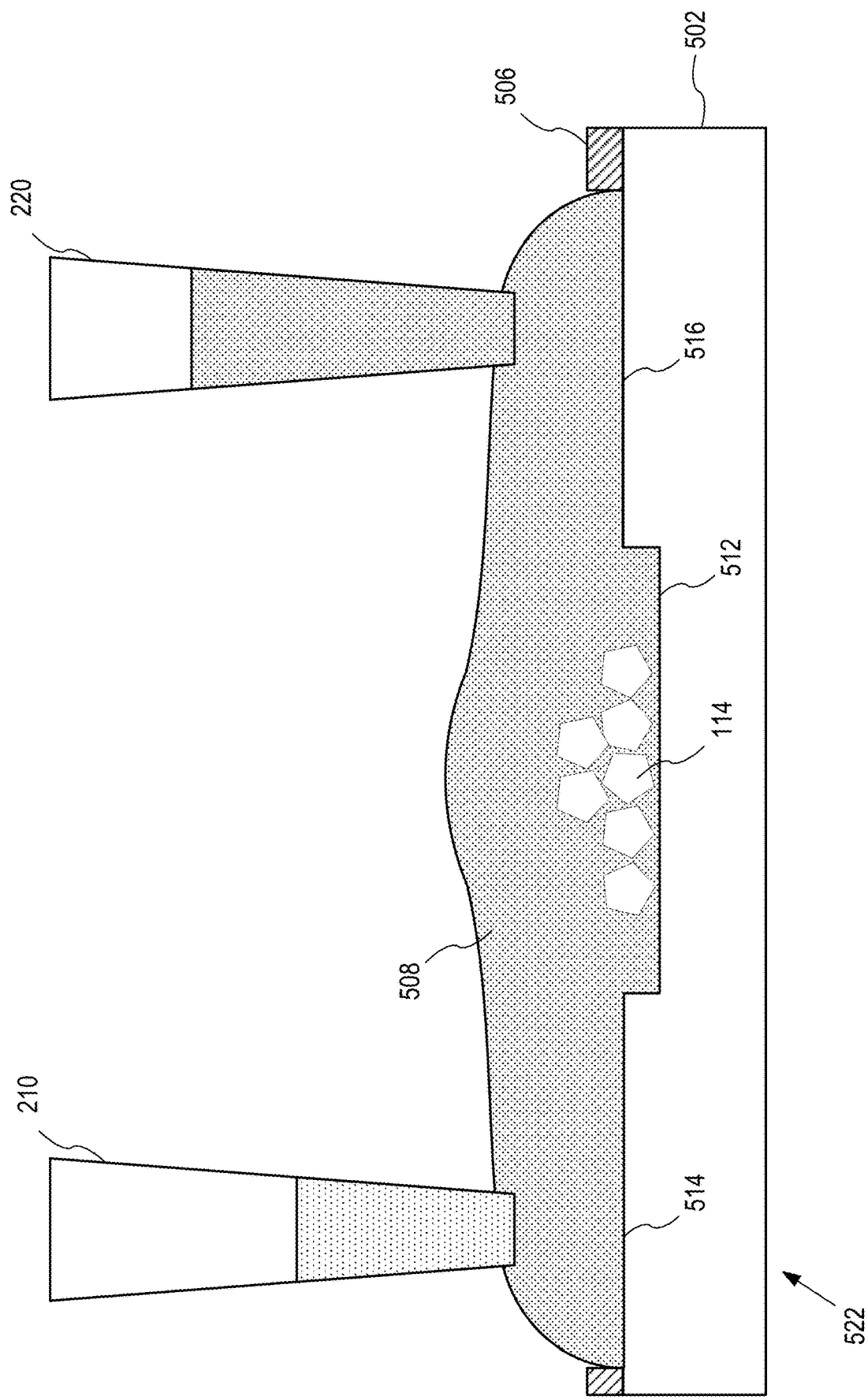

FIG. 5B illustrates a partial cross-section of array plate 522. In array plate 522, secondary areas 514 and 516 are offset from the plane on which surrounding hydrophobic area 506 is located, and primary area 512 is offset from the plane on which secondary areas 514 and 516 are located (e.g., primary area 512 is located at a primary area depth from surrounding hydrophobic area 506, secondary areas 514 and 516 are located at a secondary area depth from surrounding hydrophobic area 506, and the first region depth is greater than the secondary area depth).

Figure 5C:
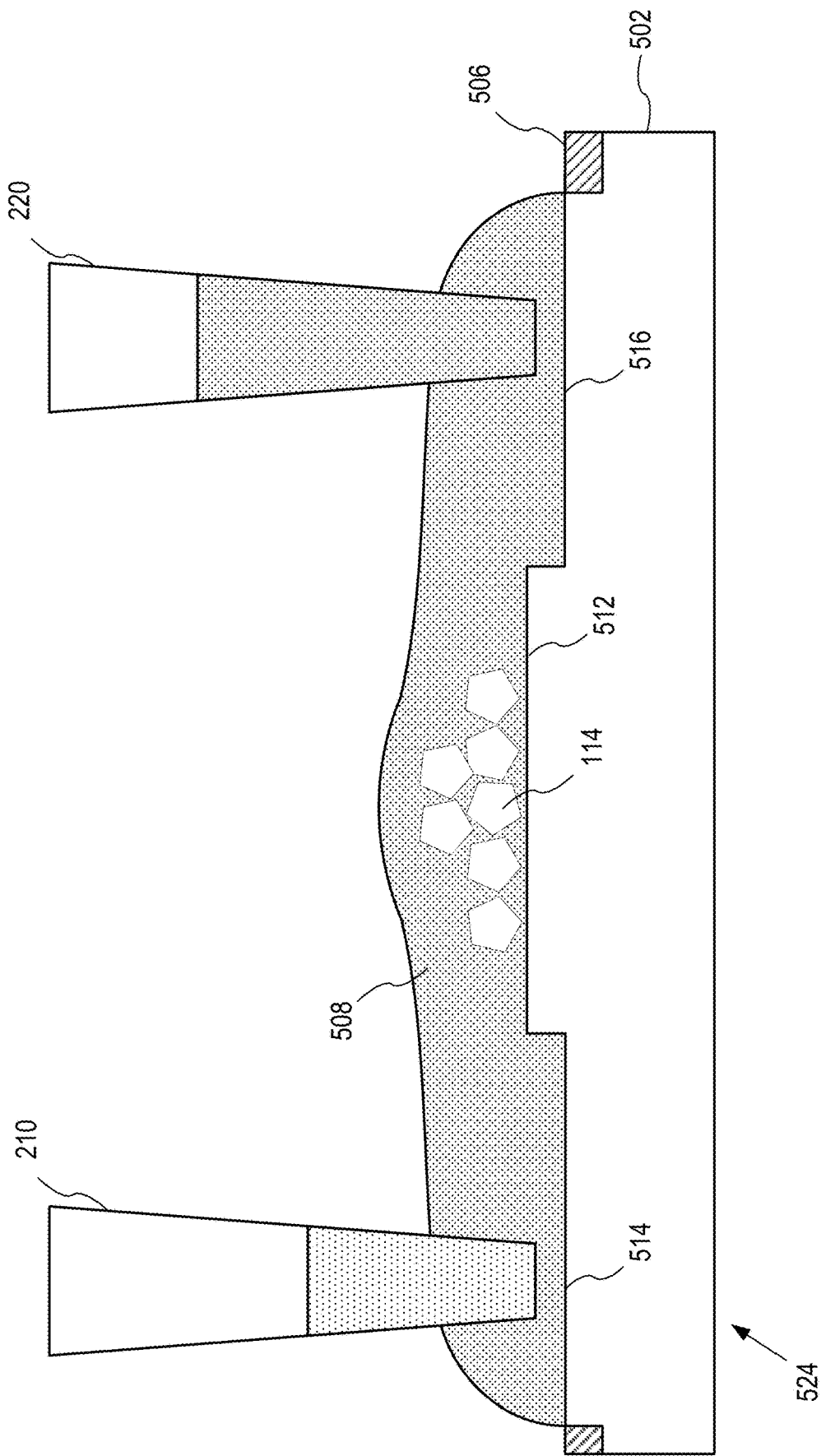

FIG. 5C illustrates a partial cross-section of array plate 524. In array plate 524, secondary areas 514 and 516 are located on a same plane as surrounding hydrophobic area 506. Primary area 512 is located offset from the plane on which secondary areas 514 and 516 are located (e.g., primary area 512 protrudes from secondary areas 514 and 516).

Figure 5D:
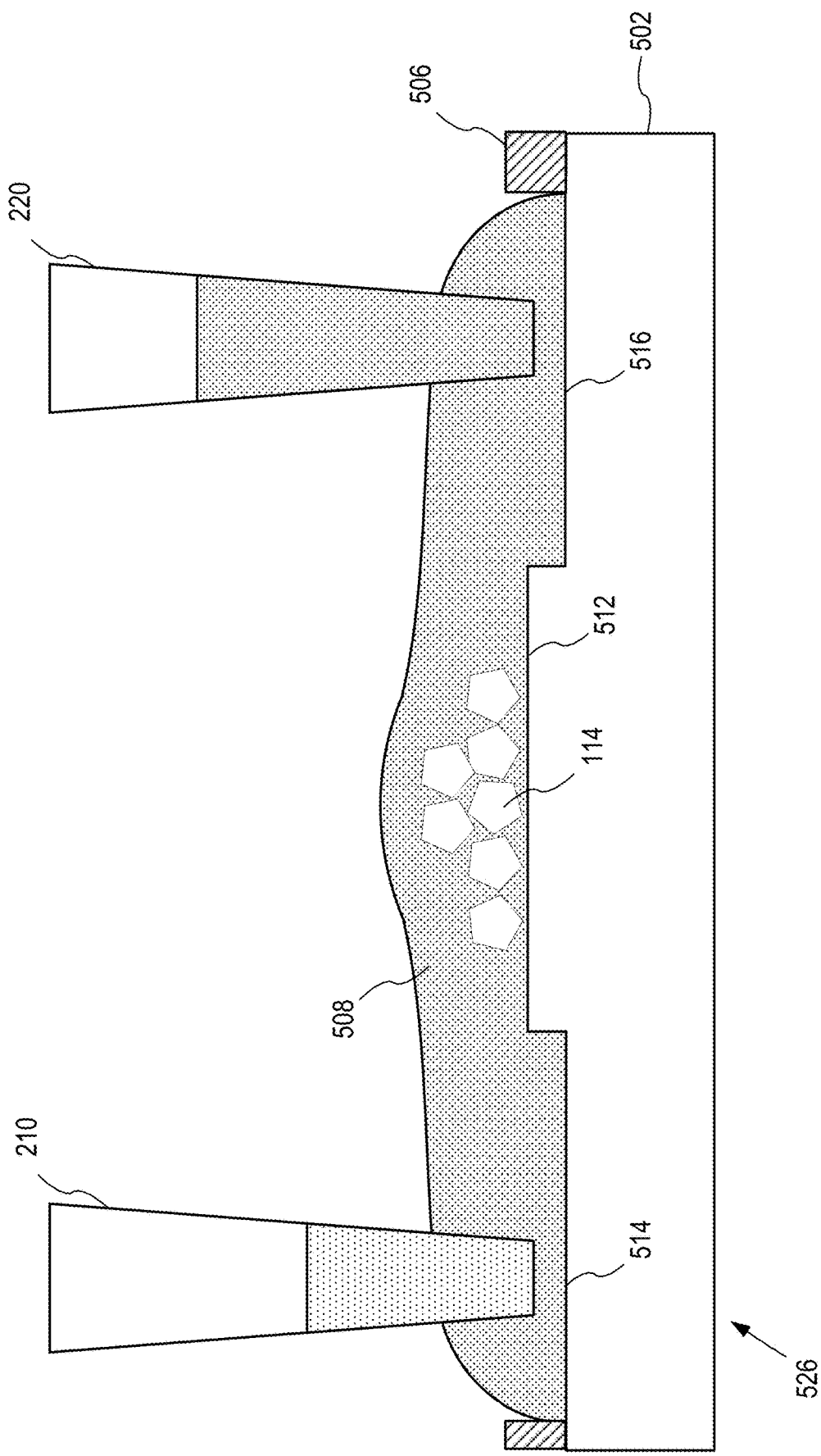

FIG. 5D illustrates a partial cross-section of array plate 526. In array plate 526, secondary areas 514 and 516 are offset from the plane on which surrounding hydrophobic area 506 is located. Primary area 512 is offset from the plane on which secondary areas 514 and 516 are located (e.g., primary area 512 is located at a primary area depth from surrounding hydrophobic area 506, secondary areas 514 and 516 are located at a secondary area depth from surrounding hydrophobic area 506, and the first region depth is less than the secondary area depth). In some embodiments, primary area 512 is located on a plane on which surrounding hydrophobic area 506 is located (e.g., the first region depth is zero).

Although FIGS. 5A-5D illustrate dispenser 210 and aspirator 220 to show the positioning of dispenser 210 over secondary area 514 and aspirator 220 over secondary area 516, dispenser 210 and aspirator 220 are not part of the array plate.

Figure 5E:
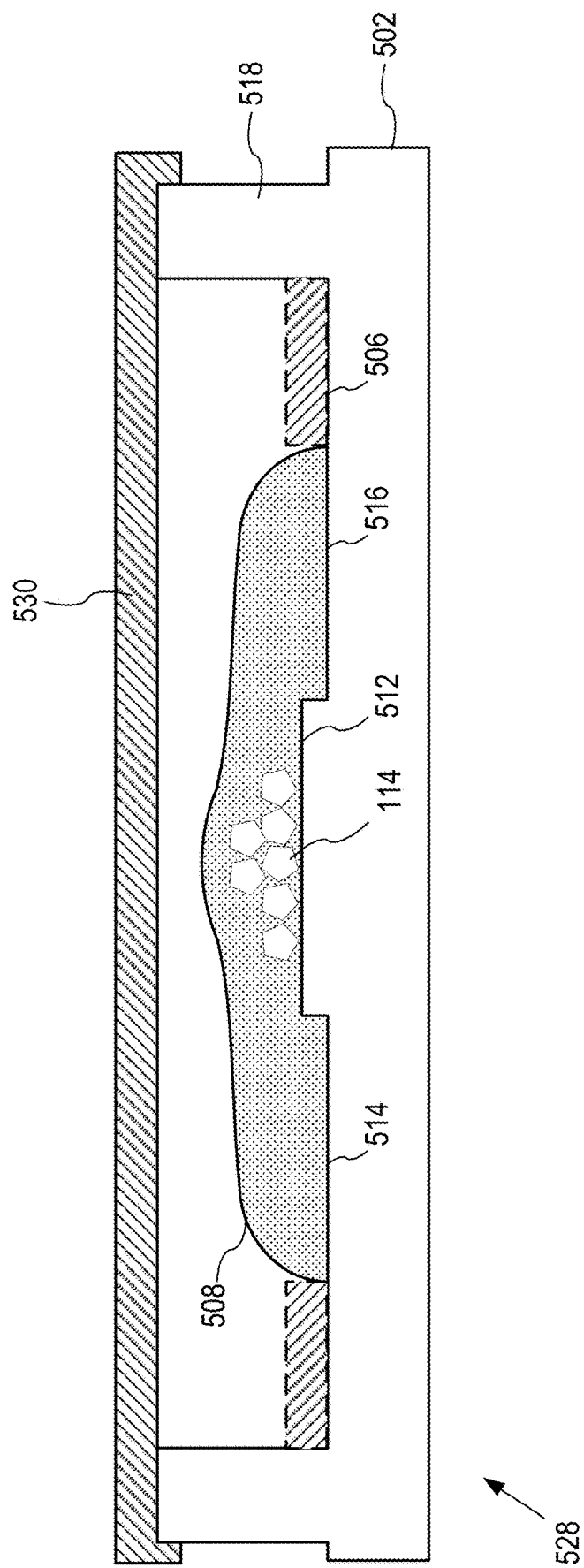

FIG. 5E illustrates a partial cross-section of array plate 528. Array plate 528 is similar to array plate 526 shown in FIG. 5D, except that array plate 528 includes walls 518.

In some embodiments, as shown in FIG. 5D, walls 518 are separated from hydrophilic regions (e.g., primary area 512 and secondary areas 514 and 516) by hydrophobic region 506. In some embodiments, walls 518 extends directly from the hydrophilic regions.

In some implementations, walls 518 define a well so that the well can hold a larger volume of liquid than a volume of liquid that the primary area and the secondary areas can hold. This allows washing with a larger volume of wash liquid, thereby enhancing the efficiency of washing.

In some embodiments, walls 518 are made of hydrophobic material (e.g., polytetrafluoroethylene). In some embodiments, walls 518 are made of hydrophilic material.

In some embodiments, walls 518 are positioned away from the primary region 512 by a predefined distance (e.g., at least 1 mm, at least 2 mm, at least 3 mm, at least 4 mm, at least 5 mm, at least 6 mm, at least 7 mm, at least 8 mm, at least 9 mm, at least 10 mm, etc.). This reduces the likelihood that cells get into the corner around walls 518.

In some embodiments, walls 518 are configured to removably couple (e.g., mate) with cap 530, as shown in FIG. 5E. Cap 530 is placed over walls 518 to preventing spillage of a liquid located on array plate 528 (e.g., a sample solution or mixture 508). For example, cap 530 is placed over walls 518 for transportation of array plate 528 and/or shaking or agitation of array plate 528. In some embodiments, walls 518 and/or cap 530 have mechanical features for maintaining cap 530 in place (e.g., walls 518 and cap 530 have mating threads, or cap 530 has latches and walls 518 have corresponding indentations for preventing slippage of latches).

Although array plate 528 shown in FIG. 5E is based on array plate 526, any other array plate (including the array plates illustrated herein, such as array plate 520, 522, 524, and 526) can be modified to have walls 518. In some embodiments, walls 518 are integrated with base 502. In some embodiments, walls 518 are formed separate from base 502 and subsequently attached to base 502 (e.g., removable grids 552 shown in FIG. 5N).

Figure 5F:
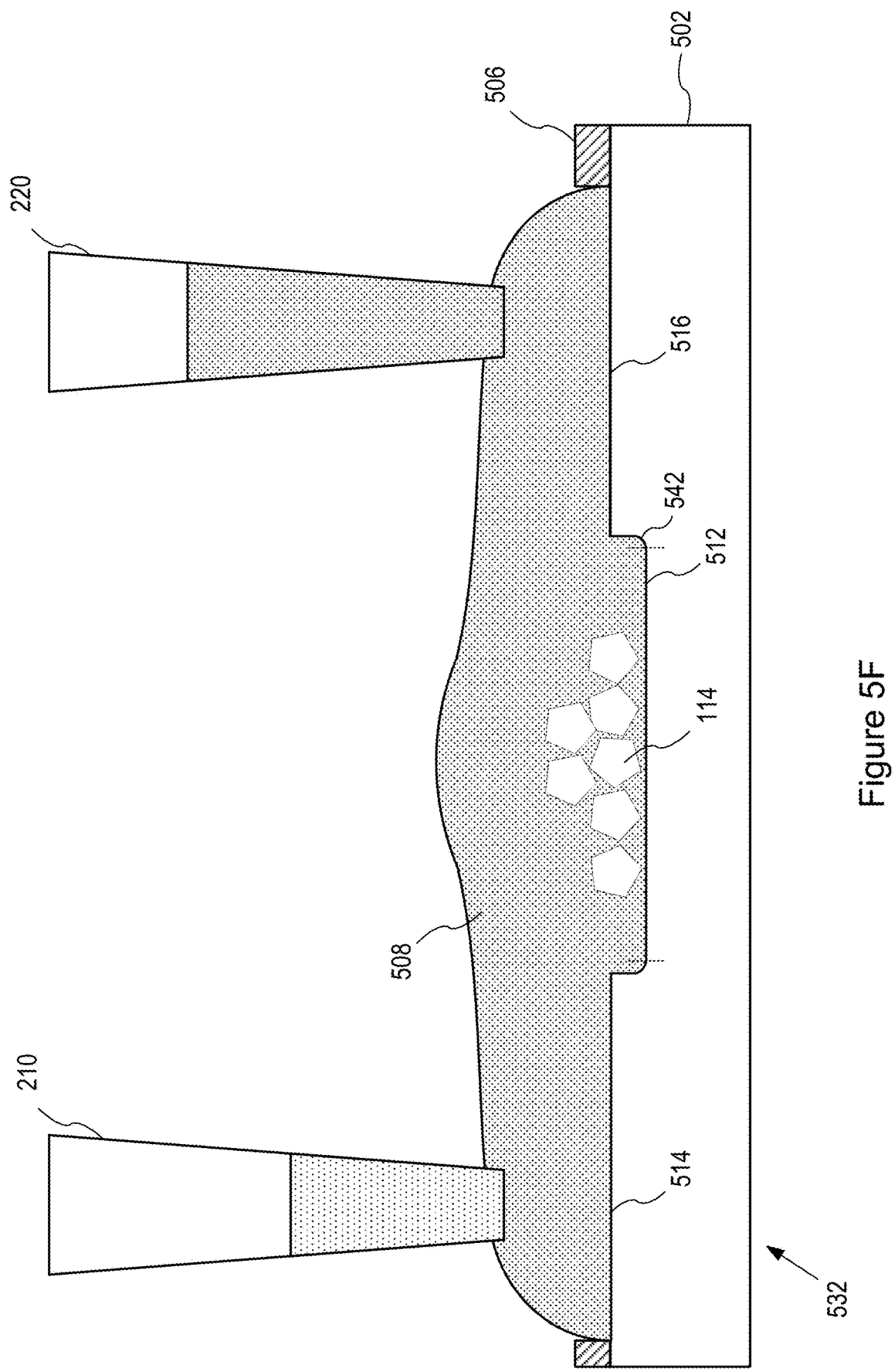

FIG. 5F illustrates a partial cross-section of array plate 532. Array plate 532 is similar to array plate 522 shown in FIG. 5B, except that region 542 around primary area 512 is filleted (e.g., edge(s) around primary area 512 has a rounded corner). In some embodiments, the region around primary area 512 (e.g., region 542) is chamfered (e.g., edge(s) around primary area 512 has a beveled corner). In some embodiments, the chamfered region is formed by removing material from array plate 532. In some embodiments, the chamfered region is formed by molding (e.g., injection molding).

Using array plate 532 with filleted or chamfered corners reduces cells remaining adjacent to the corners (after washing), thereby reduces trapping of one or more liquid droplets by the cells located adjacent to the corners (e.g., by capillary force between the cells and the plate surface around the corners). Thus, array plate 532 improves the efficiency of washing. In some embodiments, a radius of curvature (of a rounded corner) is at least 0.1 mm, 0.2 mm, 0.3 mm, 0.4 mm, 0.5 mm, or 1 mm. For example, the radius of curvature is 0.5 mm, 0.6 mm, 0.7 mm, 0.8 mm, or 0.9 mm. In some embodiments, a chamfer width is at least 0.1 mm, 0.2 mm, 0.3 mm, 0.4 mm, 0.5 mm, or 1 mm. For example, the chamfer width is 0.5 mm, 0.6 mm, 0.7 mm, 0.8 mm, or 0.9 mm. In some embodiments, a chamfer depth is at least 0.1 mm, 0.2 mm, 0.3 mm, 0.4 mm, 0.5 mm, or 1 mm. For example, the chamfer depth is 0.5 mm, 0.6 mm, 0.7 mm, 0.8 mm, or 0.9 mm. In some embodiments, a chamfer length is at least 0.14 mm, 0.28 mm, 0.42 mm, 0.56 mm, 0.7 mm, or 1.4 mm. For example, the chamfer length is 0.7 mm, 0.84 mm, 0.98 mm, 1.12 mm, or 1.26 mm.

Figure 5G:
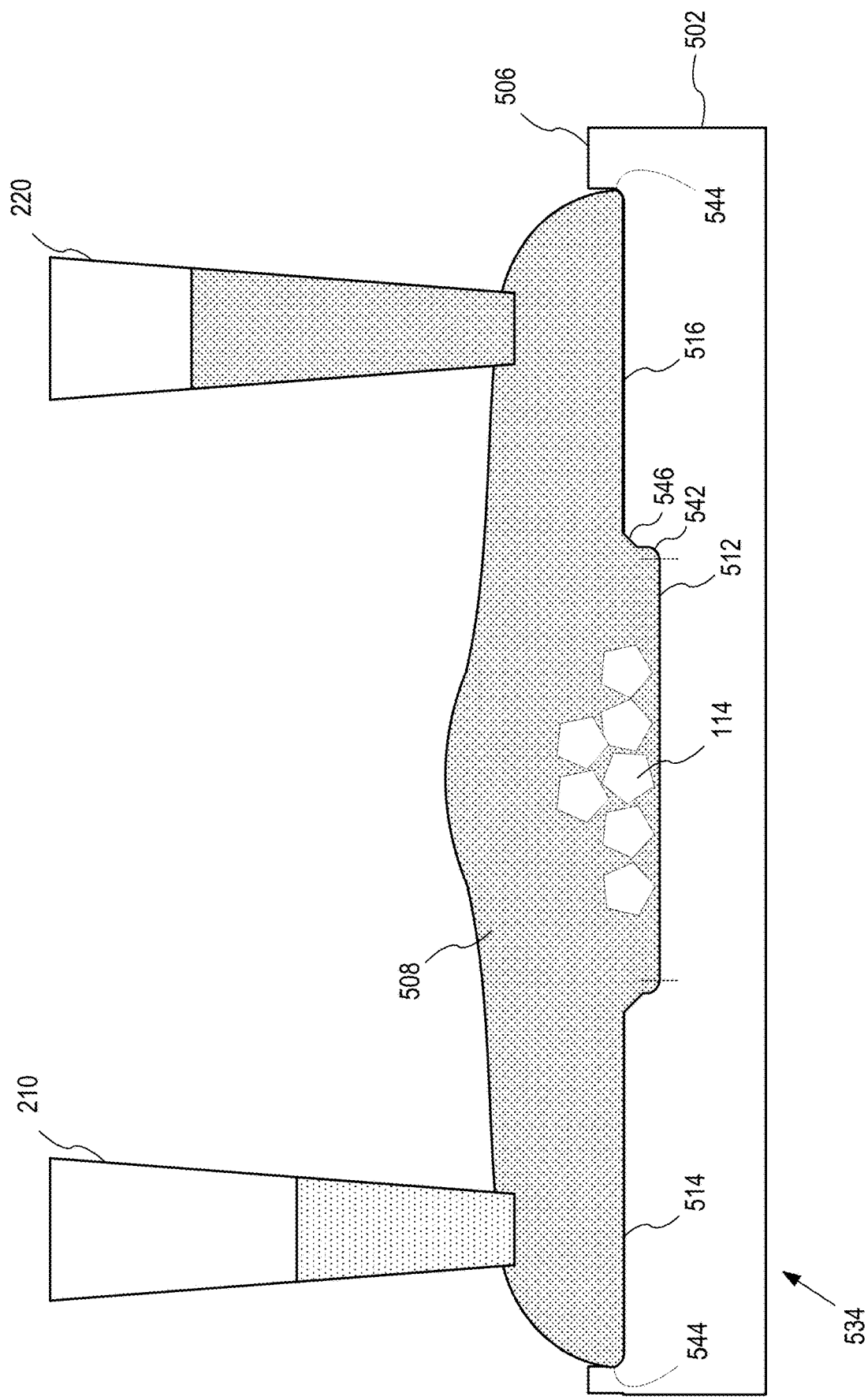

FIG. 5G illustrates a partial cross-section of array plate 534. Array plate 534 is similar to array plate 532 shown in FIG. 5F, except that regions 544 around secondary areas 514 and 516 are filleted (e.g., edges around second regions 514 and 516 have a rounded corner). In some embodiments, the regions around secondary areas 514 and 516 (e.g., regions 544) are chamfered (e.g., edges around secondary areas 514 and 516 have beveled corners). In some embodiments, the chamfered regions are formed by removing material from array plate 534. In some embodiments, the chamfered regions are formed by molding (e.g., injection molding).

Figure 5H:
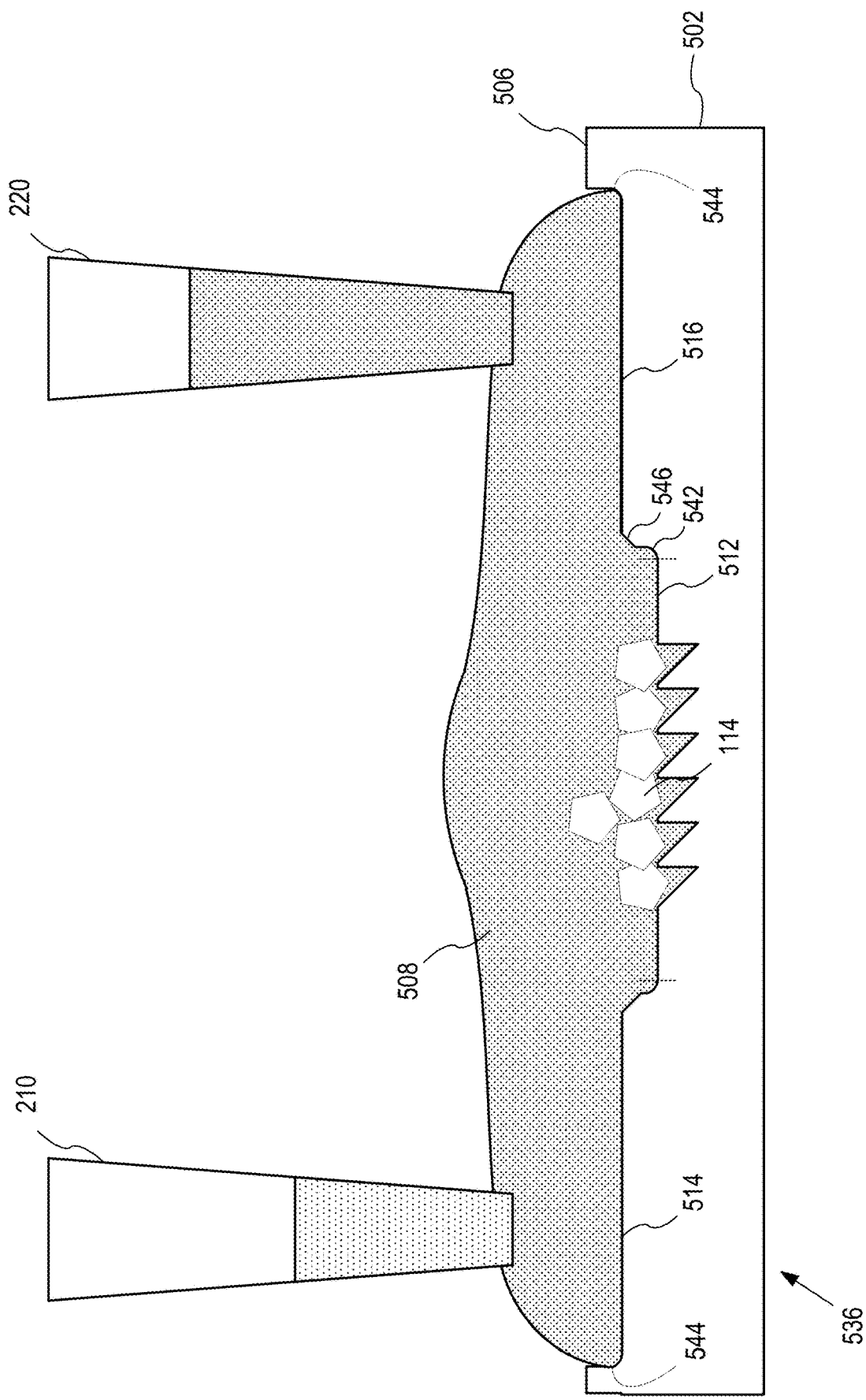

FIG. 5H illustrates a partial cross-section of array plate 536. Array plate 536 is similar to array plate 534 shown in FIG. 5G, except that a plurality of structures is defined in primary area 512, the plurality of structures configured to retain cells in the sample solution or mixture 508 during dispensing of liquid from dispenser 210 and/or aspiration of the sample solution or mixture with aspirator 220. In some embodiments, the plurality of structures includes an array of dimples. In some embodiments, a respective dimple has a characteristic dimension (e.g., a diameter, width, depth, etc.) between 1 and 100 μm (e.g., a half-spherical dimple having a diameter of 20 μm). In some embodiments, a respective dimple has a characteristic dimension between 10 and 50 μm. In some embodiments, the dimples have an asymmetric shape (e.g., a right triangular cross section, as shown in FIG. 5H) so that the dimples can retain the cells better when the liquid flows from dispenser 210 to aspirator 220.

Figure 5I:
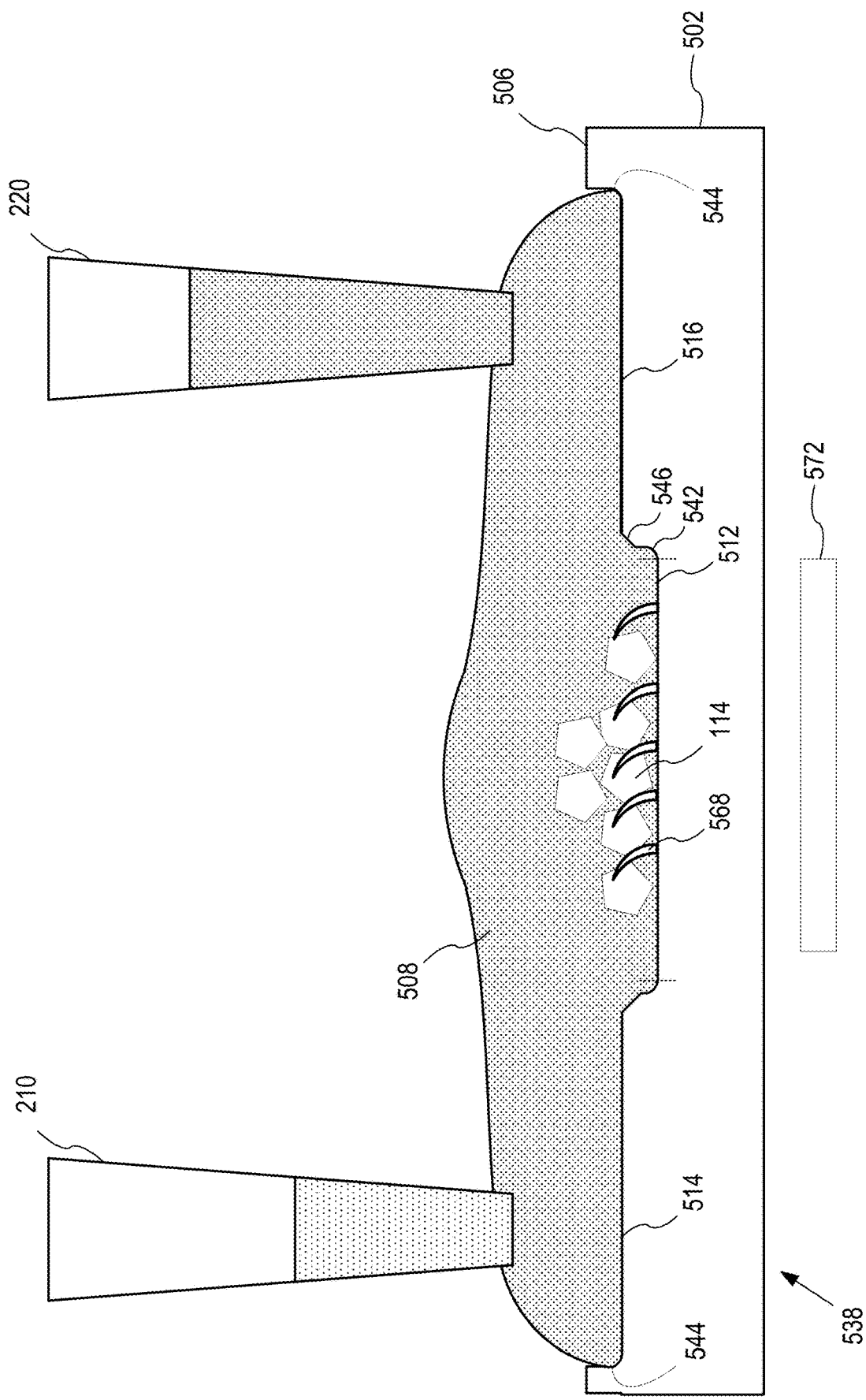

FIG. 5I illustrates a partial cross-section of array plate 538. Array plate 538 is similar to array plate 534 shown in FIG. 5G, except that a plurality of structures 568 is located over at least primary area 512. In some embodiments, the plurality of structures 568 has a shape of pillars. In some embodiments, a plurality of structures 568 has a shape of claws as shown in FIG. 5I. In some embodiments, the plurality of structures 568 includes a magnetic material (e.g., a ferromagnetic material), and the plurality of structures 568 is held by a magnetic force (e.g., a magnetic force induced by a magnetic field from magnet 572 located below array plate 538). In some embodiments, array plate 538 includes magnet 572. In some embodiments, magnet 572 is removably coupled with array plate 538.

Figure 5J:
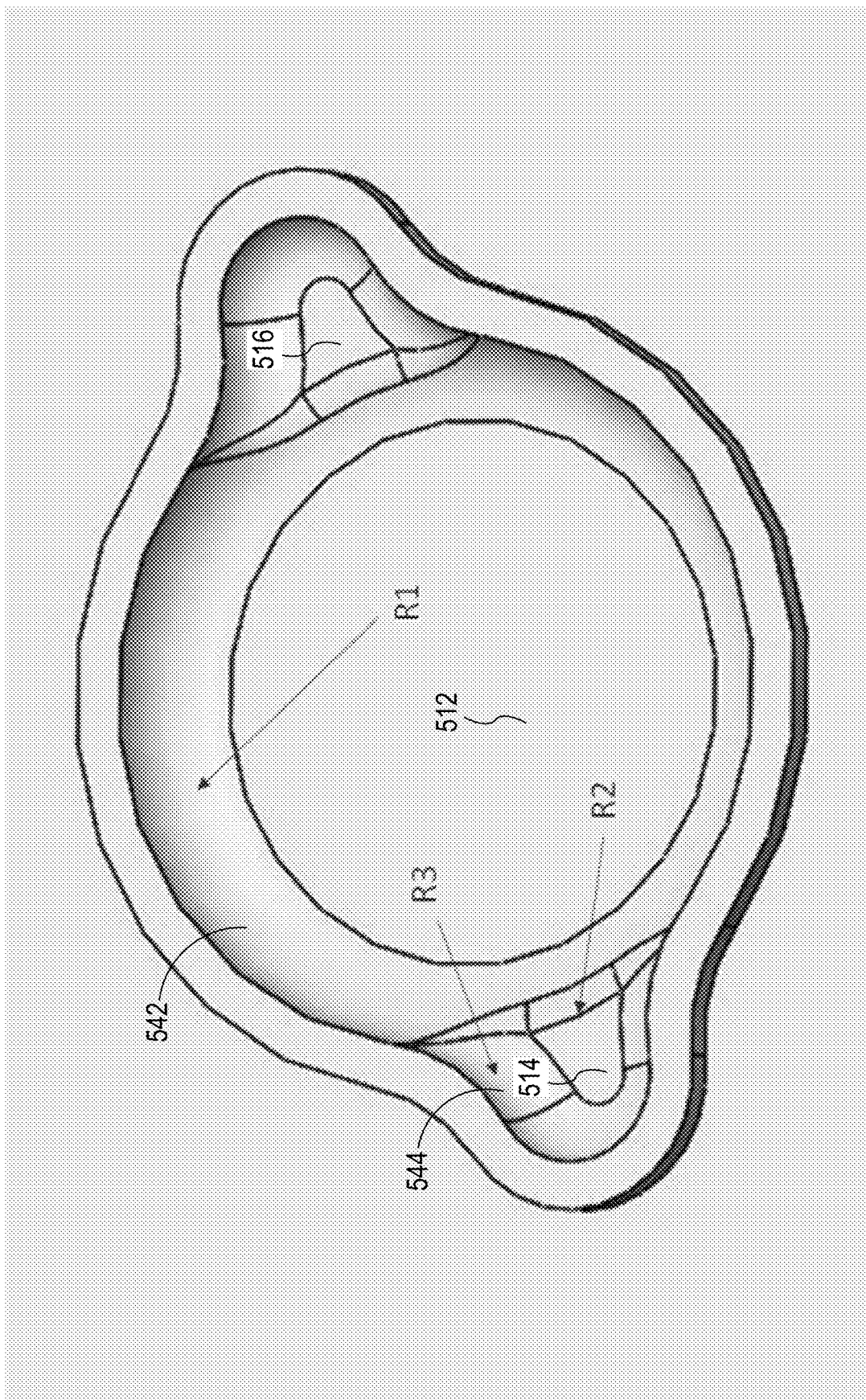
FIGS. 5J-5K illustrate an example array plate in accordance with some embodiments.
Figure 5K:
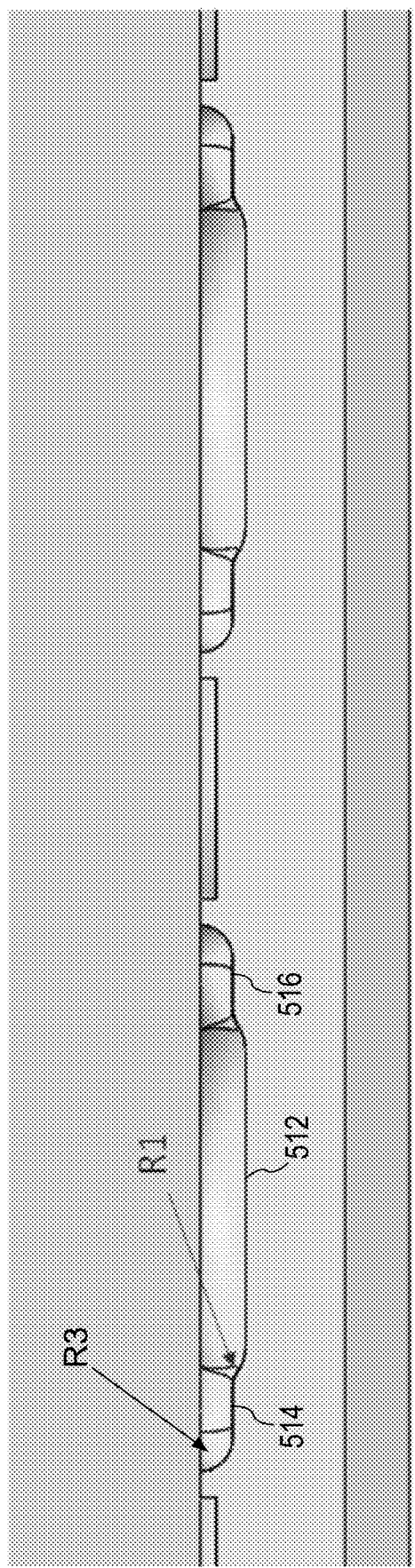

FIGS. 5J-5K illustrate an example array plate in accordance with some embodiments.

FIG. 5J is a perspective view of a portion of the array plate in accordance with some embodiments. The portion of the array plate shown in FIG. 5G has primary area 512 surrounded by region 542. As explained above with respect to FIG. 5F, region 542 is filleted or chamfered. In some embodiments, region 542 is filleted and has a radius of curvature (R1) that corresponds to at least 0.1 mm, 0.2 mm, 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 3 mm, 4 mm, 5 mm, 6 mm, 7 mm, 8 mm, 9 mm, or 10 mm. In some embodiments, region 542 has a radius of curvature (R1) that is less than 0.1 mm, 0.2 mm, 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 3 mm, 4 mm, 5 mm, 6 mm, 7 mm, 8 mm, 9 mm, or 10 mm. In some embodiments, the region 542 has a radius of curvature that is between 0.1 mm and 1 mm. In some embodiments, the region 542 has a radius of curvature that is between 0.2 mm and 0.8 mm.

The portion of the array plate shown in FIG. 5J also has secondary areas 514 and 516. In FIG. 5J, a respective second region (e.g., secondary area 514 or secondary area 516) is surrounded by region 544. In some embodiments, region 544 is filleted or chamfered. In some embodiments, region 544 is filleted and has a radius of curvature (R3) that corresponds to at least 0.1 mm, 0.2 mm, 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 3 mm, 4 mm, 5 mm, 6 mm, 7 mm, 8 mm, 9 mm, or 10 mm. In some embodiments, region 544 has a radius of curvature (R3) that is less than 0.1 mm, 0.2 mm, 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 3 mm, 4 mm, 5 mm, 6 mm, 7 mm, 8 mm, 9 mm, or 10 mm. In some embodiments, the region 544 has a radius of curvature that is between 0.1 mm and 1 mm. In some embodiments, the region 544 has a radius of curvature that is between 0.2 mm and 0.8 mm. In some embodiments, the radius of curvature (R3) of region 544 is less than the radius of curvature (R1) of region 542.

FIG. 5J also illustrates that an edge of secondary area 514 facing primary area 512 has a radius of curvature (R2) in some embodiments. In some embodiments, the radius of curvature (R2) corresponds to at least 0.1 mm, 0.2 mm, 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 3 mm, 4 mm, 5 mm, 6 mm, 7 mm, 8 mm, 9 mm, or 10 mm. In some embodiments, the radius of curvature (R2) is less than 0.1 mm, 0.2 mm, 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 3 mm, 4 mm, 5 mm, 6 mm, 7 mm, 8 mm, 9 mm, or 10 mm. In some embodiments, the radius of curvature (R2) is between 0.1 mm and 1 mm. In some embodiments, the radius of curvature (R2) is between 0.2 mm and 0.8 mm. In some embodiments, the radius of curvature (R2) is identical to the radius of curvature (R1) of region 512. In some embodiments, the radius of curvature (R2) is identical to the radius of curvature (R3) of region 544.

FIG. 5K is a partial cross-sectional view of the array plate shown in FIG. 5J.

The array plate shown in FIGS. 5J-5K have rounded corners for both primary and secondary areas, which further improves the efficiency of washing operations.

Figure 5L:
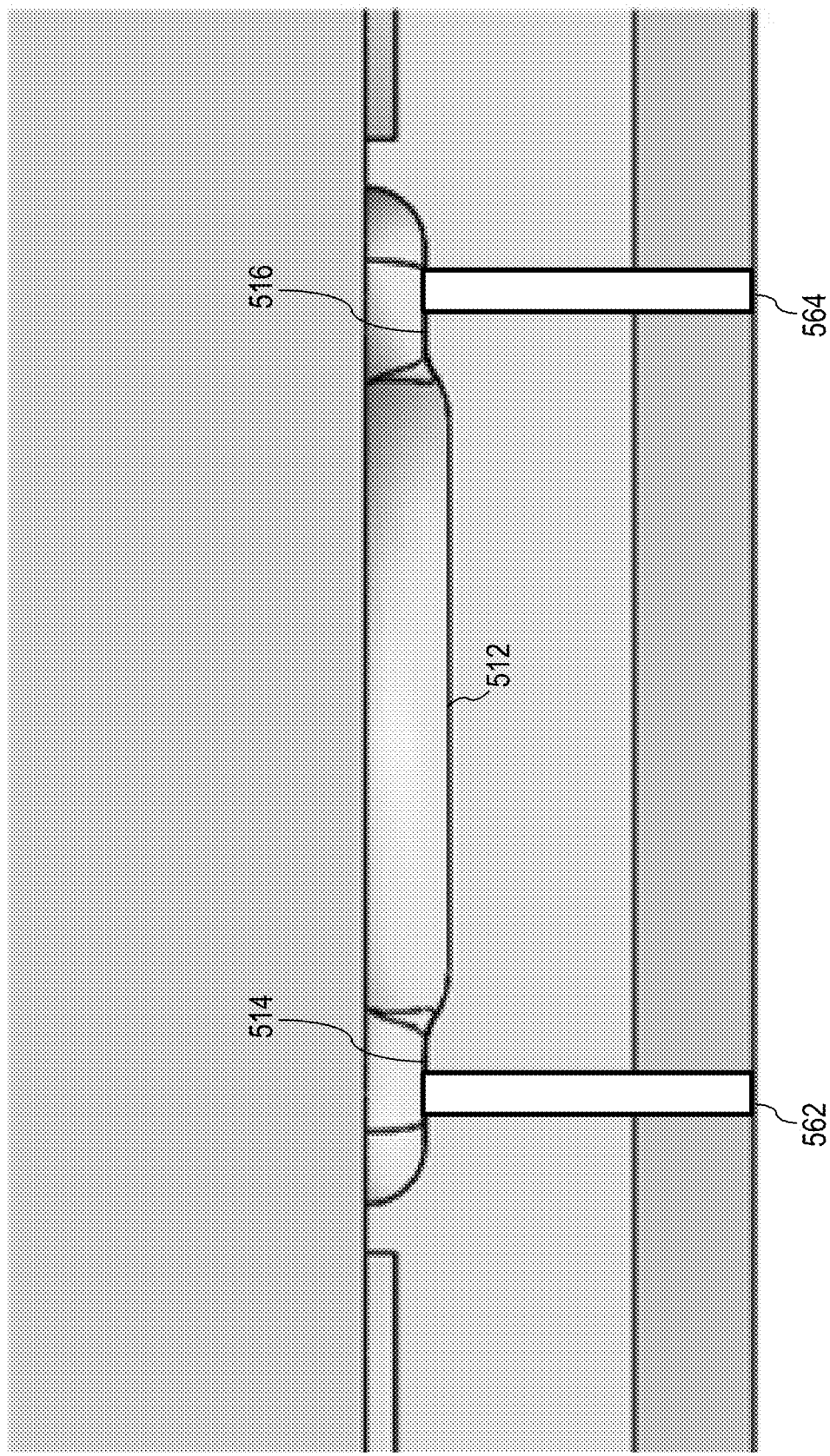
FIG. 5L illustrates an array plate in accordance with some embodiments.

FIG. 5L illustrates an array plate in accordance with some embodiments.

The array plate shown in FIG. 5L is similar to the array plate shown in FIG. 5K, except that the array plate shown in FIG. 5L defines two or more channels 562 and 564. In some embodiments, channel 562 is configured to introduce or provide liquid (e.g., a wash liquid, a reagent liquid, etc.) to the array plate. In some embodiments, channel 562 is configured to couple with a dispenser (e.g., with a coupler, such as a clip, configured to removably couple with a nozzle of the dispenser). In some embodiments, channel 564 is configured to remove liquid (e.g., a sample solution or a mixture of the sample solution with other liquids) on the array plate. In some embodiments, channel 564 is configured to couple with an aspirator (e.g., with a coupler, such as a clip, configured to removably couple with a nozzle of the aspirator). In some embodiments, secondary areas 514 and 516 are offset from each other. For example, secondary area 514 is located on a first plane and secondary area 516 is located on a second plane that is located away from the first plane (e.g., the second plane is located below the first plane).

Figure 5M:
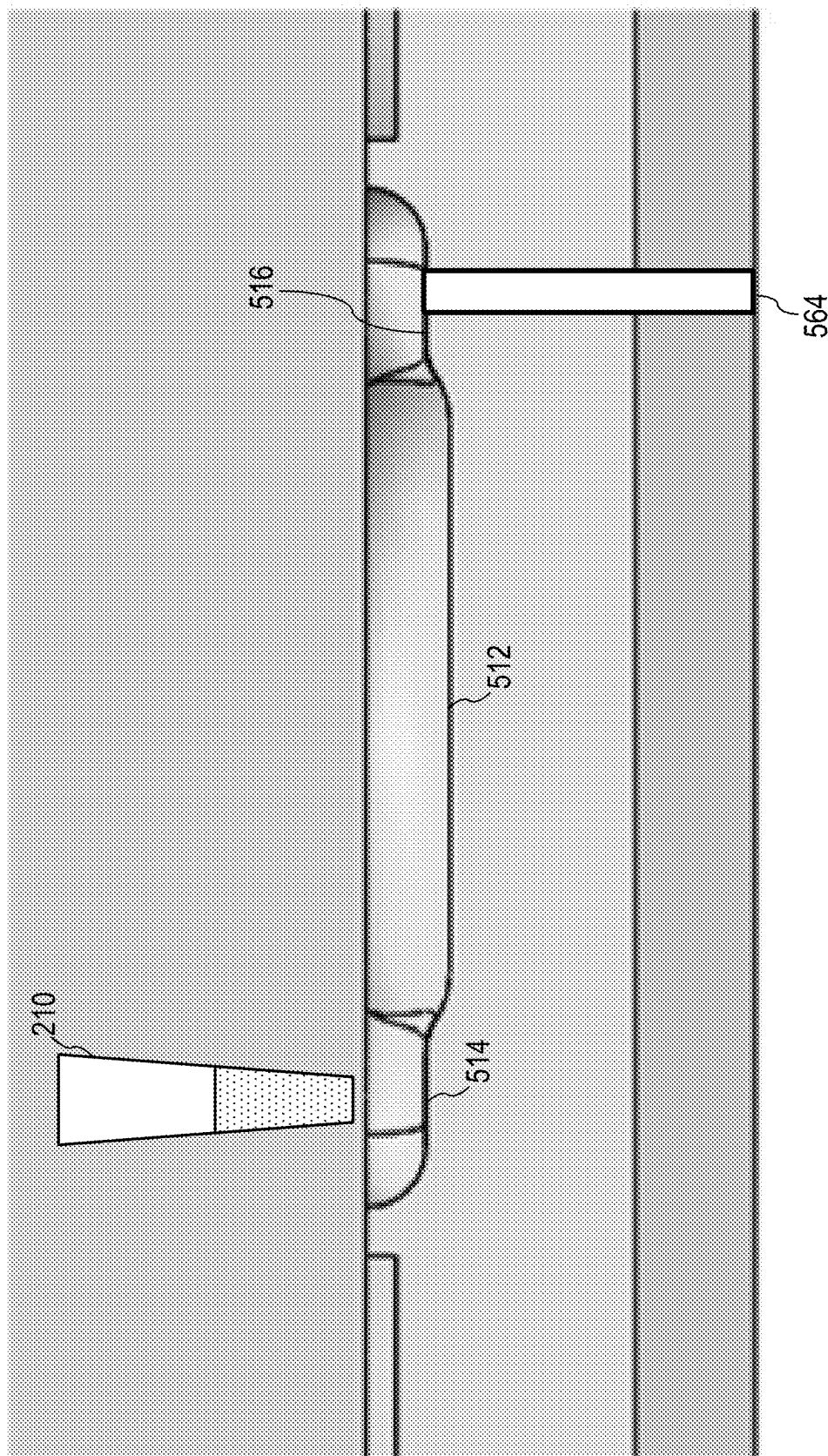
FIG. 5M illustrates an array plate in accordance with some embodiments.

FIG. 5M illustrates an array plate in accordance with some embodiments.

The array plate shown in FIG. 5M is similar to the array plate shown in FIG. 5L, except that the array plate shown in FIG. 5M defines only one channel 564.

In some embodiments, channel 564 is configured to remove liquid (e.g., a sample solution or a mixture of the sample solution with other liquids) on the array plate. In some embodiments, similar to the array plate shown in FIG. 5M, channel 564 is configured to couple with an aspirator (e.g., with a coupler, such as a clip, configured to removably couple with a nozzle of the aspirator). In such embodiments, liquid (e.g., a wash liquid or a reagent solution) is introduced by using dispenser 210 that is located above the array plate. In some embodiments, secondary area 516 is located on a first plane and primary area 512 is located on a second plane that is located away from the first plane (e.g., the second plane is located below the first plane). In some embodiments the first plane is separated from the second plane by a predefined distance (e.g., a well height that is selected for improved cell retention and washing efficiency).

In some embodiments, channel 564 is configured to introduce or provide liquid (e.g., a wash liquid, a reagent liquid, etc.) to the array plate. In some embodiments, channel 564 is configured to couple with a dispenser (e.g., with a coupler, such as a clip, configured to removably couple with a nozzle of the dispenser). In such embodiments, liquid (e.g., a sample solution or a mixture of the sample solution with another liquid) is removed by using an aspirator that is located above the array plate.

Figure 5N:
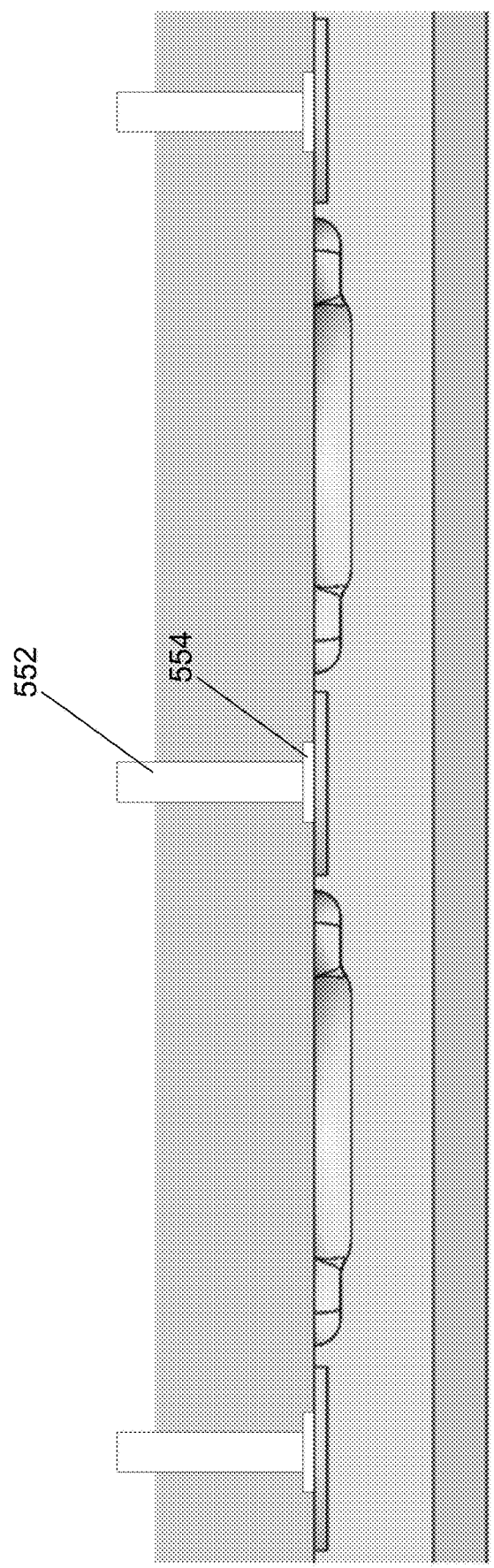
FIG. 5N illustrates a grid configured for use with an example array plate in accordance with some embodiments.

FIG. 5N illustrates grid 552 configured for use with an example array plate in accordance with some embodiments. In some embodiments, grid 552 includes polytetrafluoroethylene (PTFE). In some embodiments, grid 552 is made of polytetrafluoroethylene (PTFE). Grid 552 defines one or more walls. Gris 552 is configured for placement over the array plate to define one or more wells (e.g., a respective well for each hydrophilic region). Grid 552 increases a volume of liquid that can be placed on, or around, each hydrophilic area. In some embodiments, elastomeric layer 554 is positioned between grid 552 and the array plate. This, in some cases, reduces wicking of the liquid into the gap between grid 552 and the array plate. In some embodiments, the hydrophobic area of the array plate is coated with a hydrophobic liquid immiscible so that wicking of a hydrophilic liquid (e.g., water) is reduced or prevented.

Figure 6A:
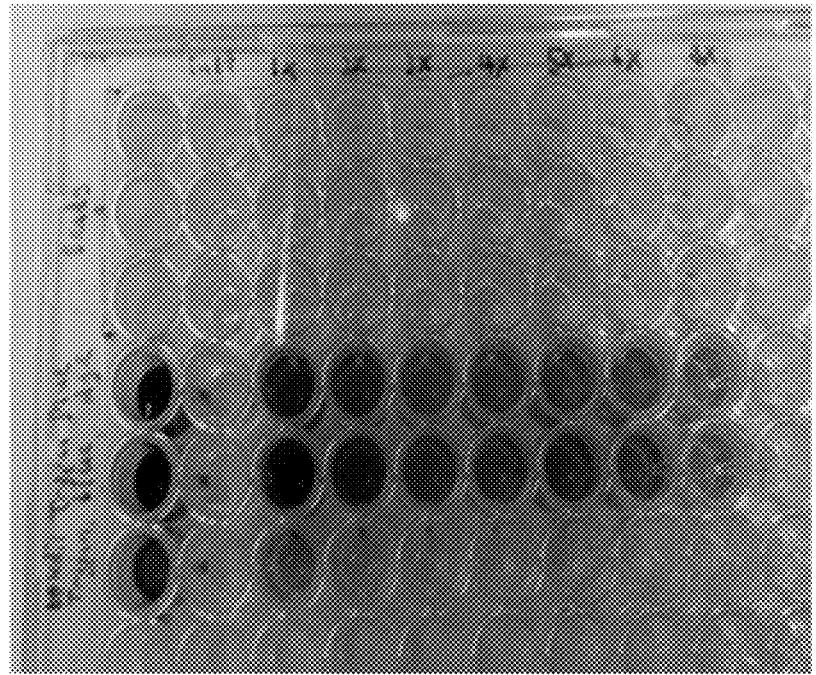
FIG. 6A shows results of washing operations performed with a conventional micro-titer plate in accordance with some embodiments.

FIG. 6A shows results of washing operations performed with a conventional micro-titer plate in accordance with some embodiments. Each sample was washed with a four-fold dilution in each step, by leaving 25 µl of the mixture and adding 75 µl of a fresh wash buffer.

The first three rows of the micro-titer plate show results of a bead retention test. A solution containing micro beads was washed six times. As shown in the image, the beads in the micro-titer plate tend to cluster along the edge of the well, which can reduce the assay performance.

The next three rows (e.g., the fourth, fifth, and sixth rows) of the micro-titer plate show results of a wash efficiency test. A solution containing a predefined concentration of an ink was washed multiple times. The third column represents solutions after the first wash, the fourth column represents solutions after the second wash, the fifth column represents solutions after the third wash, the sixth column represents solutions after the fourth wash, the seventh column represents solutions after the fifth wash, and the eighth column represents solutions after the sixth wash. With the conventional micro-titer plate, the color of the ink is still visible even after six washes. This may be due to a remaining mixture clinging onto the edge by capillary force. In addition, the variation in the color indicates the variation in the wash efficiency from well to well. Such variation in the color will lead to variations and errors in assay results.

Figure 6B:
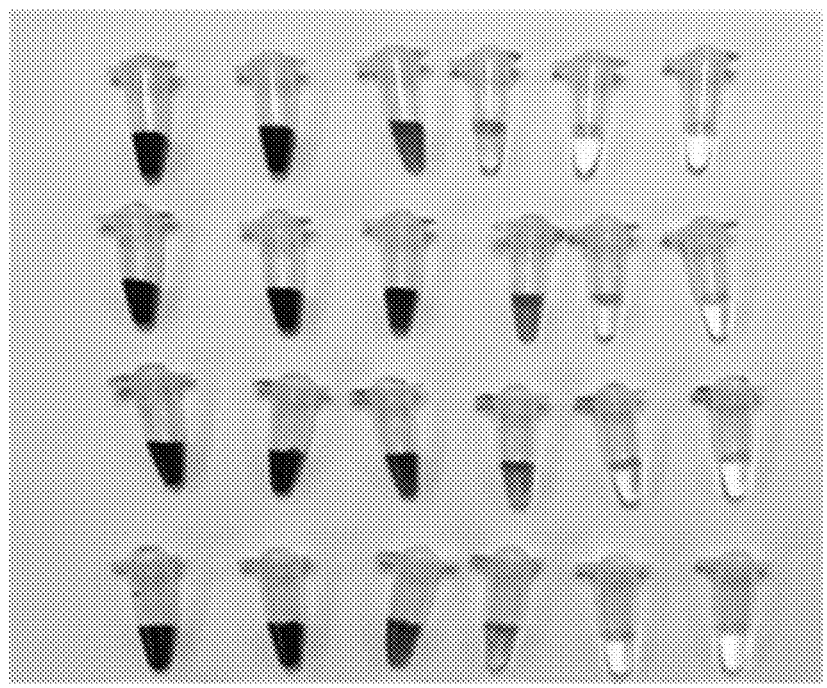
FIG. 6B shows results of washing operations performed with an example method described herein.

FIG. 6B shows results of washing operations performed with the method described herein. Again, each sample was washed with a four-fold dilution in each step, by leaving 25 µl of the mixture and adding 75 µl of a fresh wash buffer.

Each row represents sample washing performed at different nozzle depths. The first column represents solutions after the first wash, the second column represents solutions after the second wash, the third column represents solutions after the third wash, the fourth column represents solutions after the fourth wash, the fifth column represents solutions after the fifth wash, and the sixth column represents solutions after the sixth wash. As shown in FIG. 6B, each solution has turned clear after the sixth wash. Compared to the wash results shown in FIG. 6A, FIG. 6B shows that the washing efficiency of the method described herein is far superior. In addition, the variation from sample to sample is reduced compared to the variation observed in FIG. 6A.

Figure 6C:
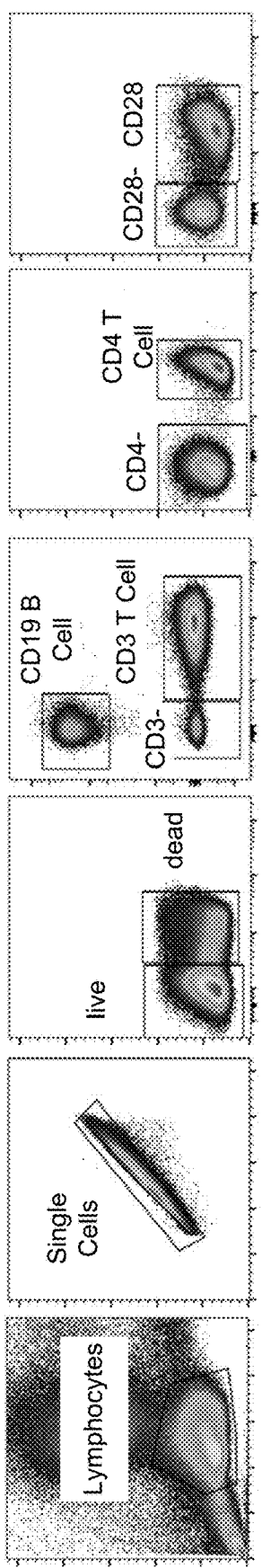
FIG. 6C illustrates the results of fluorescence-activated cell sorting of lymphocytes washed using a conventional method in accordance with some embodiments.
Figure 6D:
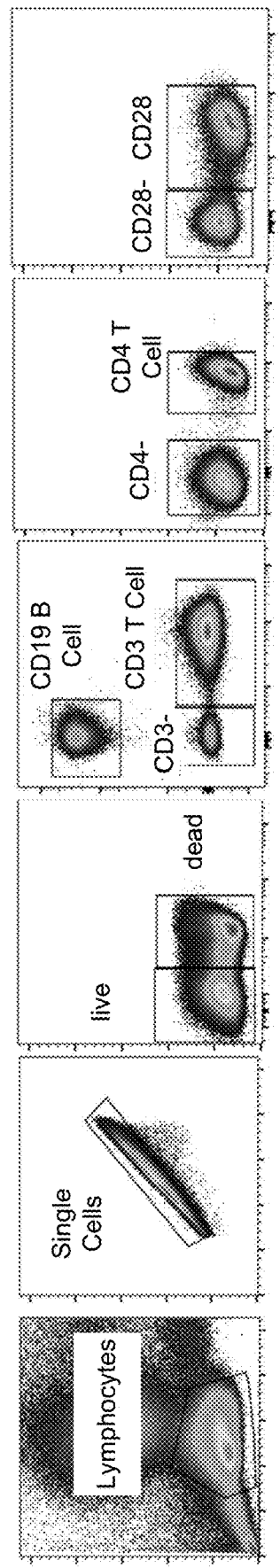
FIG. 6D illustrates the results of fluorescence-activated cell sorting of lymphocytes washed using the method described herein in accordance with some embodiments.

In addition, FIGS. 6C and 6D show that the method described herein facilitates cell sorting. FIG. 6C illustrates the results of fluorescence-activated cell sorting of lymphocytes washed using a conventional method. FIG. 6D illustrates the results of fluorescence-activated cell sorting of lymphocytes washed using the method described herein. As shown in FIGS. 6C and 6D, the resolution of fluorescence-activated cell sorting and the data quality have been improved by using the washing method described herein. Furthermore, by utilizing the array plates described herein, less time was required for preparing a sample for flow cytometry analysis (as compared to using conventional methods).

Figure 7A:
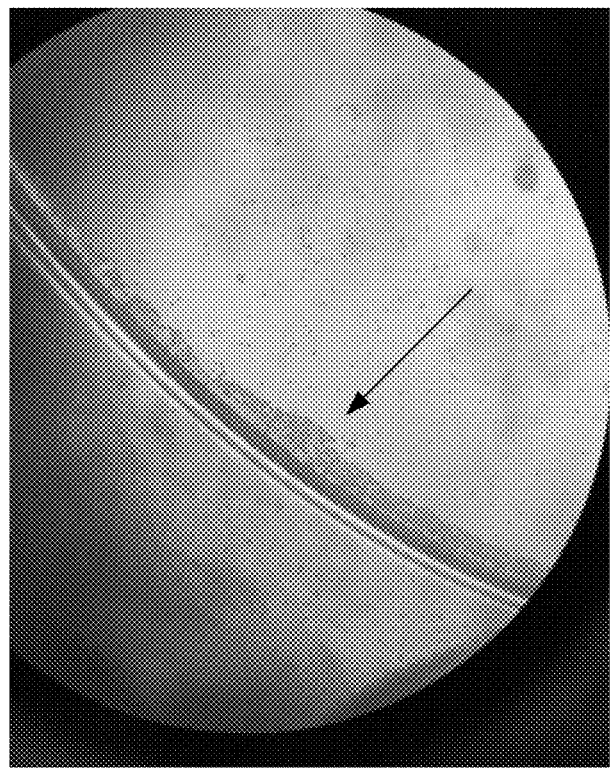
FIG. 7A shows results of washing operations performed with an array plate without filleted corners in accordance with some embodiments.
Figure 7B:
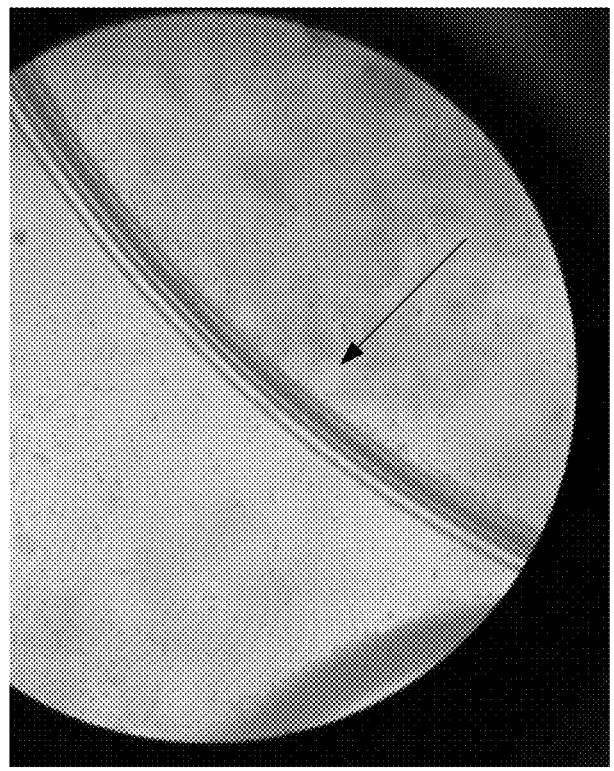
FIG. 7B shows results of washing operations performed with an array plate with filleted corners in accordance with some embodiments.

FIGS. 7A and 7B are microscope images of beads on array plates in accordance with some embodiments. FIG. 7A shows results of washing operations performed with an array plate without filleted corners (e.g., array plates with sharp corners) in accordance with some embodiments, and FIG. 7B shows results of washing operations performed with an array plate with filleted corners (e.g., FIGS. 5F-5K) in accordance with some embodiments. For each array plate, we dispensed a solution containing 7 µm diameter polystyrene beads (in order to simulate retention of cells) over a secondary area, shook the array plate with the solution using a shaker, and left the array plate to allow the polystyrene beads to settle. Subsequently, the solution was aspirated slowly to remove the solution while maintaining most of the polystyrene beads on the array plate. Thereafter, we washed the array plate by adding a flow cytometry (FACS) buffer, shaking the array plate, and aspirating the FACS buffer. We repeated these washing steps (e.g., repeat once, repeat twice, repeat thrice, etc.). Finally, we dispensed a phosphate buffered saline (PBS) solution, shook the array plate, and observed the array plate (e.g., around the primary areas) using a microscope.

As shown in FIG. 7A, washing operations performed with an array plate without filleted corners leave a large number of beads adjacent to the corners (e.g., a periphery of the primary area). As shown in FIG. 7B, washing operations performed with an array plate with filleted corners reduce the number of beads remaining adjacent to the corners, which improves the washing efficiency. In addition, fewer washing steps are required with the array plate with filleted corners than with the array plate without filleted corners.

Similarly, FIGS. 7C and 7D show that washing operations performed with an array plate without filleted corners (e.g., array plates having sharp corners) have a large number of cells adjacent to the corners (FIG. 7C) and washing operations performed with an array plate with filleted corners reduce the number of cells remaining adjacent to the corners (FIG. 7D).

In light of these principles, we turn to certain embodiments.

In accordance with some embodiments, an apparatus for washing an array plate includes one or more dispensers (e.g., dispenser 230 in FIG. 3A). A respective dispenser of the one or more dispensers is configured to dispense a first liquid on the array plate (e.g., dispenser 230 is configured to dispense wash liquid 106 on the array plate). The respective dispenser includes a first piston configured to slide at least partially within a first channel (e.g., piston 236 is configured to slide within channel 234); and a first valve (e.g., valve 212) configured to allow the first liquid in the first channel to be dispensed from the first channel through the first valve and prevent a liquid from entering into the first channel through the first valve.

In some embodiments, the respective dispenser includes a first tube defining the first channel and configured for holding the first liquid (e.g., tube 235 defining channel 234). The first piston is slidably coupled with the first tube (e.g., piston 236 is configured to slide within tube 235 while piston 236 remains in contact with tube 235). The first valve is coupled with the first tube and configured to allow the first liquid in the first tube to be dispensed from the first tube through the first valve and prevent a liquid from entering into the first tube through the first valve.

In some embodiments, the first piston defines a second channel (e.g., channel 238) that is distinct from the first channel. The respective dispenser also includes a second valve (e.g., valve 252) that is distinct from the first valve. The second valve is configured to allow the first liquid in the second channel to be dispensed from the second channel through the second valve and prevent a liquid from entering into the second channel through the second valve.

In some embodiments, the first piston comprises a second tube (e.g., the shell of piston 236) that defines the second channel. In some embodiments, the second tube is distinct from the first tube. The second tube is configured for holding the first liquid. The second valve is coupled with the second tube and configured to allow the first liquid in the second tube to be dispensed from the second tube through the second valve and prevent a liquid from entering into the second tube through the second valve.

In some embodiments, the apparatus further includes one or more aspirators (e.g., aspirator 240). A respective aspirator of the one or more aspirators is configured to aspirate a liquid on the array plate. The respective aspirator includes a second piston (e.g., piston 246) configured to slide at least partially within a third channel (e.g., channel 244); and a third valve (e.g., valve 222) configured to allow the liquid on the array plate to be aspirated into the third channel through the third valve and prevent a liquid in the third channel from exiting from the third channel through the third valve.

In some embodiments, the respective aspirator includes a third tube (e.g., tube 245) defining the third channel. The third tube is distinct from the first tube. The second piston is slidably coupled with the third channel. (e.g., piston 246 is configured to slide within channel 244). The third valve is coupled with the third tube and configured to allow the liquid on the array plate to be aspirated into the third channel through the third valve and prevent a liquid from entering into the third tube through the third valve.

In some embodiments, the second piston defines a fourth channel (e.g., channel 248) that is distinct from the third channel. The respective aspirator also includes a fourth valve (e.g., valve 262) that is distinct from the third valve. The fourth valve is configured to allow the liquid in the third channel to enter into the fourth channel and prevent a liquid in the fourth channel from exiting from the fourth channel through the fourth valve.

In some embodiments, the second piston comprises a fourth tube (e.g., the shell of piston 246) that defines the fourth channel. In some embodiments, the fourth tube is distinct from the third tube. The fourth valve is coupled with the fourth tube and configured to allow the liquid in the third tube to enter into the fourth tube through the fourth valve and prevent a liquid in the fourth tube from exiting from the fourth tube through the fourth valve.

In some embodiments, the one or more dispensers comprise a plurality of dispensers, which is arranged in a first array (e.g., dispensers 210 in FIG. 4F). In some embodiments, the one or more dispensers comprise a plurality of aspirators, which is arranged in a second array (e.g., aspirators 220 in FIG. 4F).

In some embodiments, the plurality of dispensers is arranged in a two-dimensional array having multiple rows and multiple columns of dispensers (e.g., FIG. 4G). In some embodiments, the plurality of aspirators is arranged in a two-dimensional array having multiple rows and multiple columns of aspirators (e.g., FIG. 4G).

In some embodiments, two or more first channels of the plurality of dispensers are defined in a first block (e.g., the cylinder block in FIG. 3H).

In some embodiments, two or more second channels of the plurality of dispensers are defined in a second block (e.g., the dispenser piston block in FIG. 3H). In some embodiments, the first pistons are integrated with the second block. In some embodiments, the second block is distinct from the first block.

In some embodiments, two or more third channels of the plurality of aspirators are defined in a first block (e.g., the cylinder block in FIG. 3H).

In some embodiments, two or more fourth channels of the plurality of aspirators are defined in a third block (e.g., the aspirator piston block in FIG. 3H). In some embodiments, the second pistons are integrated with the third block. In some embodiments, the third block is distinct from the first block. In some embodiments, the third block is distinct from the second block.

In accordance with some embodiments, an apparatus for washing an array plate includes one or more dispensers, a respective dispenser of the one or more dispensers configured to dispense a first liquid on the array plate; and one or more aspirators that are distinct from the one or more dispensers. A respective aspirator of the one or more aspirators includes a positive displacement pump configured to aspirate liquid on the array plate. In some embodiments, the positive displacement pump is configured to aspirate a predefined or preselected volume of the liquid on the array plate.

In accordance with some embodiments, an apparatus is configured for washing an array plate having a primary area and at least two secondary areas. The apparatus includes a first set of one or more pipettes configured to dispense a first liquid at a first time on a first secondary area of the array plate and a second set of one or more pipettes that is distinct from (and mutually exclusive to) the first set of one or more pipettes, the second set of one or more pipettes configured to aspirate liquid on the array plate from a second secondary area of the array plate at either the first time or a second time that is distinct from the first time (e.g., the second time is subsequent to the first time). The first set of one or more pipettes is also configured to aspirate at either the second time or a third time that is distinct from the second time (e.g., the third time is subsequent to the second time) the liquid on the array plate from the first secondary area. For example, in some cases, the first set of one or more pipettes (e.g., one or more dispensers) are used to dispense the first liquid at a first time at a location adjacent to the first secondary area of the array plate, and thereafter, the second set of one or more pipettes (e.g., one or more aspirators) are used to aspirate a first portion of liquid on the array plate from the second secondary area of the array plate. Subsequently, the first set of one or more pipettes are used to aspirate a second portion of the liquid on the array plate from the first secondary area of the array plate. Dispensing the first liquid at a location adjacent to the first secondary area pushes away any cells located, before dispensing the first liquid, on the first secondary area of the array plate from the first secondary area of the array plate (e.g., toward the primary area), and thus, reduces a number of cells that can be aspirated (and thus, gets lost) in a subsequent aspiration from a location adjacent to the first secondary area. This allows a larger portion of the liquid to be aspirated without loss (or with reduced loss) of cells through aspiration.

In accordance with some embodiments, a method for washing an array plate having a primary area and at least two secondary areas includes dispensing, with a first set of one or more pipettes, a first liquid at a first time on a first secondary area of the array plate. The method also includes aspirating, with a second set of one or more pipettes that is distinct from (and mutually exclusive to) the first set of one or more pipettes, liquid on the array plate from a second secondary area of the array plate at either the first time or a second time that is distinct from the first time (e.g., the second time is subsequent to the first time). The method further includes aspirating, with the first set of one or more pipettes (or a third set of one or more pipettes that is distinct from, and mutually exclusive to, the first set of one or more pipettes and the second set of one or more pipettes) at either the second time or a third time that is distinct from the second time (e.g., the third time is subsequent to the second time) the liquid on the array plate from the first secondary area.

In accordance with some embodiments, a method for washing a sample includes obtaining an array plate that includes an array of hydrophilic areas surrounded by one or more hydrophobic areas. A respective solution containing a sample is located on a respective hydrophilic area of the array of hydrophilic areas. The respective hydrophilic area includes one or more indentations from a respective surrounding hydrophobic area of the one or more hydrophobic areas. The respective hydrophilic area includes a first indented surface (e.g., secondary area 514 and/or secondary area 516) that is offset from a reference surface defined by the respective surrounding hydrophobic area. The method also includes placing an aspirator nozzle above the respective hydrophilic area at least 100 μm from the first indented surface; and aspirating the solution with the aspirator nozzle while the aspirator nozzle is located at least 100 μm from the first indented surface (e.g., FIG. 2A).

In some embodiments, the solution is aspirated with the aspirator nozzle while the aspirator nozzle is located at least 200 μm from the first indented surface. In some embodiments, the solution is aspirated with the aspirator nozzle while the aspirator nozzle is located at least 300 μm from the first indented surface.

In some embodiments, the first indented surface is offset from the reference surface by a first distance; and the respective hydrophilic area includes a second indented surface that is offset from the reference surface by a second distance.

In some embodiments, the second distance is distinct from the first distance (e.g., FIG. 5B). In some embodiments, the second distance is greater than the first distance. In some embodiments, the first distance is greater than the second distance.

In some embodiments, the second distance is equal to the first distance.

In some embodiments, the second distance is less than 3000 μm. In some embodiments, the second distance is 2000 μm or less. In some embodiments, the second distance is 1750 μm or less. In some embodiments, the second distance is 1500 μm or less. In some embodiments, the second distance is 1250 μm or less. In some embodiments, the second distance is 1000 μm or less. In some embodiments, the second distance is 750 μm or less. In some embodiments, the second distance is 500 μm or less.

In some embodiments, the first distance is 1000 μm or less. In some embodiments, the first distance is 750 μm or less. In some embodiments, the first distance is 500 μm or less. In some embodiments, the first distance is 250 μm or less.

In some embodiments, the method includes placing the aspirator nozzle above the respective hydrophilic area at least 100 µm from the first indented surface. In some embodiments, the method includes placing the aspirator nozzle above the respective hydrophilic area at least 200 µm from the first indented surface. In some embodiments, the method includes placing the aspirator nozzle above the respective hydrophilic area at least 300 µm from the first indented surface.

In some embodiments, the solution is aspirated at a rate between 1 and 50 µl/sec. In some embodiments, the solution is aspirated at a rate between 2 and 20 µl/sec. In some embodiments, the solution is aspirated at a rate of 20 µl/sec or less. In some embodiments, the solution is aspirated at a rate of 10 µl/sec or less. In some embodiments, the solution is aspirated at a rate of 5 µl/sec or less.

In some embodiments, the method includes, prior to aspirating the respective solution with the aspirator nozzle, shaking the array plate. Shaking the array plate facilitates mixing of the wash liquid and the sample solution. In some cases, shaking the array plate also facilitates releasing chemical and/or biological reagents from the surface, thereby improving removal of such chemical and/or biological reagents.

In some embodiments, the method includes, subsequent to shaking the array plate and prior to aspirating the respective solution with the aspirator nozzle, settling the sample in the respective solution by more than 10 minutes. In some embodiments, the method includes, subsequent to shaking the array plate and prior to aspirating the respective solution with the aspirator nozzle, settling the sample in the respective solution by more than 15 minutes.

In some embodiments, the method includes, subsequent to shaking the array plate and prior to aspirating the respective solution with the aspirator nozzle, settling the sample in the respective solution by less than 90 minutes. In some embodiments, the method includes, subsequent to shaking the array plate and prior to aspirating the respective solution with the aspirator nozzle, settling the sample in the respective solution by less than 60 minutes.

In some embodiments, the respective solution has a volume less than 200 µL. In some embodiments, the respective solution has a volume less than 70 µL.

In some embodiments, the method includes introducing a liquid (e.g., a wash liquid, a reagent liquid, etc.) to the solution (e.g., dispensing the liquid onto the solution). In some embodiments, the liquid is introduced at a rate between 1 and 50 µl/sec. In some embodiments, the liquid is introduced at a rate between 2 and 20 µl/sec. In some embodiments, the liquid is introduced at a rate of 20 µl/sec or less. In some embodiments, the liquid is introduced at a rate of 10 µl/sec or less. In some embodiments, the liquid is introduced at a rate of 5 µl/sec or less.

In some embodiments, the operation of introducing the liquid and the operation of aspirating the solution are repeated at least three times. In some embodiments, the operation of introducing the liquid and the operation of aspirating the solution are repeated no more than nine times.

In accordance with some embodiments, a method for washing a sample includes obtaining an array plate that includes an array of hydrophilic areas surrounded by one or more hydrophobic areas. A respective solution containing a sample is located on a respective hydrophilic area of the array of hydrophilic areas. The respective hydrophilic area includes one or more indentations from a respective surrounding hydrophobic area of the one or more hydrophobic areas. The respective hydrophilic area includes at least two indented surfaces (e.g., secondary area 514 and secondary area 516) that are offset from a reference surface defined by the respective surrounding hydrophobic area. The method also includes dispensing a first liquid (e.g., a wash liquid) onto a first indented surface of the array plate with a first set of one or more pipettes at a first time and aspirating liquid on the array plate from a second indented surface of the array plate with a second set of one or more pipettes distinct from the first set of one or more pipettes at the first time or a second time that is distinct from the first time. In some embodiments, the method further includes aspirating the liquid on the array plate from the first indented surface of the array plate with the first set of one or more pipettes at the second time.

In accordance with some embodiments, an apparatus is configured for performing any method described herein.

In some embodiments, the apparatus includes one or more dispensers, a respective dispenser of the one or more dispensers configured to dispense a first liquid on an array plate. The respective dispenser includes a first piston configured to slide at least partially within a first channel; and a first valve configured to allow the first liquid in the first channel to be dispensed from the first channel through the first valve and prevent a liquid from entering into the first channel through the first valve.

In accordance with some embodiments, a device for washing a sample includes a plate having an array of hydrophilic areas; and one or more hydrophobic areas surrounding the array of hydrophilic areas. A respective hydrophilic area of the array of hydrophilic areas is offset from a surrounding hydrophobic area of the one or more hydrophobic areas. The respective hydrophilic area includes a primary area and two or more secondary areas that extend from the primary area on a plane defined by the primary area.

In some embodiments, the surrounding hydrophobic area is coated with hydrophobic oil.

In some embodiments, the primary area has a shape of a circle and each secondary area of the two or more secondary areas has a shape of a partial circle.

In some embodiments, the primary area is located on a first plane, a first secondary area of the two or more secondary areas is located on a second plane that is offset from the first plane, and a second secondary area of the two or more secondary areas is located on a third plane that is offset from the first plane. In some embodiments, the second plane and the third plane overlap each other. In some embodiments, the second plane is offset from the third plane.

In some embodiments, the device defines a first channel (e.g., channel 562, FIG. 5L) with a through-hole extending from a first secondary area of the two or more secondary areas to a bottom of the device so that liquid can be transported through the first channel between the bottom of the device and the first secondary area.

In some embodiments, the device defines a second channel (e.g., channel 564, FIG. 5L) that is distinct from the first channel and includes a through-hole extending from a first secondary area of the two or more secondary areas to a bottom of the device so that liquid can be transported through the first channel between the bottom of the device and the second secondary area. In some embodiments, the device defines the first channel without defining the second channel (e.g., FIG. 5M).

In some embodiments, a plurality of structures is defined on the primary area (e.g., FIG. 5H).

In some embodiments, a plurality of structures is located on the primary area (e.g., FIG. 5I).

In some embodiments, the plurality of structures includes a magnetic material so that the plurality of structures can be held with a magnetic force.

Various aspects and characteristics of the methods of using the array plates described above are applicable to array slides (e.g., adding one or more solutions to one or more liquid droplets of the respective liquid droplets, performing an immunoassay, and washing a respective liquid droplets), and vice versa. Because these aspects and characteristics are described above, they are not repeated herein for brevity.

It is well known to a person having ordinary skill in the art that array slides and plates can be used in many other biological and chemical reactions. Therefore, such details and specific examples are omitted for brevity.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An apparatus, comprising:
   one or more dispensers, a respective dispenser of the one or more dispensers configured to dispense a first liquid on an array plate, the respective dispenser including:
   a first tube defining at least a portion of a first channel in an interior of the first tube and configured for holding the first liquid;
   a first piston located and slidable at least partially within the first channel;
   a first valve coupled to the first tube and configured to allow the first liquid in the first channel to be dispensed from the first channel through the first valve and prevent a liquid from entering into the first channel through the first valve; and a
   second valve that is distinct from the first valve, wherein the second valve is coupled to the first piston and configured to allow the first liquid to enter the first channel through the second valve and prevent a liquid in the first channel from exiting from the first channel through the second valve.

2. The apparatus of claim 1, wherein the first valve is a first check valve and the second valve is a second check valve.

3. The apparatus of claim 1, wherein:
   the first piston defines a second channel that is distinct from the first channel so that the second valve allows the first liquid to enter the first channel from the second channel through the second valve and prevents a liquid in the first channel from existing from the first channel to the second channel through the second valve.

4. The apparatus of claim 1, further comprising:
   one or more aspirators that are distinct from the one or more dispensers, a respective aspirator of the one or more aspirators configured to aspirate liquid on the array plate, wherein:
   the respective aspirator includes:
      a second tube defining at least a portion of a second channel in an interior of the second tube;
      a second piston located and slidable at least partially within the second channel;
      a third valve coupled to the second tube and configured to allow the liquid on the array plate to be aspirated into the second channel through the third valve and prevent the aspirated liquid in the second channel from exiting from the second channel through the third valve; and
      a fourth valve that is distinct from the third valve, wherein the fourth valve is coupled to the second piston and configured to allow the aspirated liquid in the second channel to exit from the second channel through the fourth valve and prevent a liquid from entering the second channel through the fourth valve; and
   the one or more aspirators are coupled to the one or more dispensers.

5. The apparatus of claim 4, wherein:
   the first piston defines a third channel that is distinct from the first channel so that the second valve allows the first liquid to enter the first channel from the third channel through the second valve and prevents a liquid in the first channel from existing from the first channel to the third channel through the second valve.

6. The apparatus of claim 5, wherein:
   the first piston comprises a third tube that defines the third channel.

7. The apparatus of claim 5, wherein:
   the second piston defines a fourth channel that is distinct from the second channel so that the fourth valve allows the aspirated liquid in the second channel to exit from the second channel to the fourth channel through the fourth valve and prevents a liquid in the fourth channel from entering the second channel through the fourth valve.

8. The apparatus of claim 7, wherein:
   the second piston comprises a fourth tube that defines the fourth channel.

9. The apparatus of claim 7, further comprising:
   a first block; and
   a second block that is distinct and separate from the first block, wherein:
   the one or more dispensers comprise a plurality of dispensers;
   the one or more aspirators comprise a plurality of aspirators;
   first tubes of the plurality of dispensers are integrated with the first block; and
   second tubes of the plurality of aspirators are integrated with the second block.

10. The apparatus of claim 9, further comprising:
    a third block that is distinct and separate from the first block and the second block, wherein second pistons of the plurality of aspirators are integrated with the third block.

11. An apparatus, comprising:
    one or more dispensers, a respective dispenser of the one or more dispensers configured to dispense a first liquid on an array plate, the respective dispenser including:
    a first tube defining at least a portion of a first channel in an interior of the first tube and configured for holding the first liquid;
    a first piston located and slidable at least partially within the first channel; and
    a first valve coupled to the first tube and configured to allow the first liquid in the first channel to be dispensed from the first channel through the first valve and prevent a liquid from entering into the first channel through the first valve; and one or more aspirators that are distinct from the one or more dispensers, a respective aspirator of the one or more aspirators configured to aspirate liquid on the array plate, wherein:

the respective aspirator includes:
- a second tube defining at least a portion of a second channel in an interior of the second tube;
- a second piston located and slidable at least partially within the second channel; and
- a second valve coupled to the second tube and configured to allow the liquid on the array plate to be aspirated into the second channel through the second valve and prevent a liquid in the second channel from exiting from the second channel through the second valve; and the one or more aspirators are coupled to the one or more dispensers.

12. The apparatus of claim 11, wherein:
the respective aspirator also includes a third valve that is distinct from the second valve, wherein the third valve is coupled to the second piston and configured to allow the liquid in the second channel to exit from the second channel through the third valve and prevent a liquid from entering the second channel through the third valve.

13. The apparatus of claim 11, wherein:
the one or more dispensers comprise a plurality of dispensers, which is arranged in a first array; and/or
the one or more aspirators comprise a plurality of aspirators, which is arranged in a second array.

14. The apparatus of claim 13, wherein:
the plurality of dispensers is arranged parallelly to one another in a two-dimensional array having multiple rows and multiple columns of dispensers; and/or
the plurality of aspirators is arranged parallelly to one another in a two-dimensional array having multiple rows and multiple columns of aspirators.

15. The apparatus of claim 13, further comprising a first block, wherein:
two or more first channels of the plurality of dispensers are defined in the first block.

16. The apparatus of claim 15, wherein:
two or more second channels of the plurality of aspirators are defined in the first block.

17. The apparatus of claim 11, further comprising:
a filter located at a tip of the respective aspirator for preventing aspiration of cells.

18. The apparatus of claim 17, further comprising:
a vibrator coupled to the filter to provide vibration to the filter for preventing or reducing accumulation of cells on the filter.

19. A method for washing a sample, the method comprising:
obtaining an array plate that includes an array of hydrophilic areas surrounded by one or more hydrophobic areas, wherein:
- a respective solution containing a sample is located on a respective hydrophilic area of the array of hydrophilic areas;
- the respective hydrophilic area includes one or more indentations having a non-zero depth relative to a respective surrounding hydrophobic area of the one or more hydrophobic areas; and
- the one or more indentations include a first indented surface; and with the apparatus of claim 11:
- placing a tip of an aspirator above the respective hydrophilic area at least 100 µm from the first indented surface; and
- aspirating the respective solution on the respective hydrophilic area with the aspirator while the tip of the aspirator is located at least 100 µm from the first indented surface.

20. The apparatus of claim 11, further comprising a first block, wherein the one or more aspirators are coupled to the one or more dispensers via the first block.

* * * * *